US009638202B2

United States Patent
Ozaki et al.

(10) Patent No.: US 9,638,202 B2
(45) Date of Patent: May 2, 2017

(54) CENTRIFUGAL PUMP APPARATUS

(71) Applicant: TC1 LLC, Pleasanton, CA (US)

(72) Inventors: Takayoshi Ozaki, Iwata (JP); Hiroyuki Yamada, Iwata (JP); Ken Sugiura, Iwata (JP)

(73) Assignee: TC1 LLC, Pleasanton, CA (US)

( * ) Notice: Subject to any disclaimer, the term of this patent is extended or adjusted under 35 U.S.C. 154(b) by 0 days.

(21) Appl. No.: 15/174,639

(22) Filed: Jun. 6, 2016

(65) Prior Publication Data

US 2016/0281728 A1    Sep. 29, 2016

Related U.S. Application Data

(62) Division of application No. 13/822,220, filed as application No. PCT/JP2011/070450 on Sep. 8, 2011, now Pat. No. 9,382,908.

(30) Foreign Application Priority Data

Sep. 14, 2010  (JP) ................................. 2010-205787

(51) Int. Cl.
*H02K 5/12*       (2006.01)
*F04D 29/047*   (2006.01)
(Continued)

(52) U.S. Cl.
CPC ......... *F04D 29/0473* (2013.01); *A61M 1/101* (2013.01); *A61M 1/1015* (2014.02);
(Continued)

(58) Field of Classification Search
CPC .. A61M 1/101; A61M 1/1015; A61M 1/1017; A61M 1/1031; F04D 13/0666;
(Continued)

(56) References Cited

U.S. PATENT DOCUMENTS 1,093,868 A    4/1914   Leighty
2,684,035 A    7/1954   Kemp
(Continued)

FOREIGN PATENT DOCUMENTS

CN    1347585 A    5/2002
CN    1462344 A    12/2003
(Continued)

OTHER PUBLICATIONS

Asama, J., et al., "A Compact Highly Efficient and Low Hemolytic Centrifugal Blood Pump With a Magnetically Levitated Impeller", Artificial Organs, vol. 30, No. 3, Mar. 1, 2006 (Mar. 1, 2006), pp. 160-167.

(Continued)

*Primary Examiner* — Patrick Hamo
(74) *Attorney, Agent, or Firm* — Kilpatrick Townsend & Stockton LLP

(57) ABSTRACT

A centrifugal blood pump apparatus includes a plurality of permanent magnets (17) in an impeller (10) in a blood chamber (7), a plurality of coils (20) in a motor chamber (8), and a magnetic element (18) in each of the coils (20). The magnetic elements (18) are made shorter than the coils (20) to lower attractive force between the magnetic elements (18) and the permanent magnets (17) in the impeller (10), to set a large gap between the magnetic elements (18) and the permanent magnets (17). As a result, axial attractive force and negative rigidity can be lowered while required torque is satisfied.

15 Claims, 35 Drawing Sheets

(51) Int. Cl.

| | | |
|---|---|---|
| *A61M 1/10* | (2006.01) | |
| *F04D 13/06* | (2006.01) | |
| *F04D 1/04* | (2006.01) | |
| *F04D 29/048* | (2006.01) | |
| *H02K 21/24* | (2006.01) | |
| *H02K 7/09* | (2006.01) | |
| *F04D 7/04* | (2006.01) | |
| *F04D 29/22* | (2006.01) | |

(52) U.S. Cl.
 CPC ........ *A61M 1/1017* (2014.02); *A61M 1/1029* (2014.02); *F04D 1/04* (2013.01); *F04D 7/04* (2013.01); *F04D 13/064* (2013.01); *F04D 13/0666* (2013.01); *F04D 29/048* (2013.01); *F04D 29/22* (2013.01); *H02K 7/09* (2013.01); *H02K 21/24* (2013.01); *H02K 5/12* (2013.01); *H02K 2205/03* (2013.01); *H02K 2213/03* (2013.01)

(58) Field of Classification Search
 CPC ............... F04D 29/0413; F04D 29/048; F16C 32/0402; F16C 33/107; H02K 5/1282; H02K 7/14; H02K 21/24
 See application file for complete search history.

(56) References Cited

U.S. PATENT DOCUMENTS

| | | |
|---|---|---|
| 3,023,334 A | 2/1962 | Burr et al. |
| 3,510,229 A | 5/1970 | Smith |
| 3,620,638 A | 11/1971 | Kaye et al. |
| 3,870,382 A | 3/1975 | Reinhoudt |
| 3,932,069 A | 1/1976 | Giardini et al. |
| 3,960,468 A | 6/1976 | Boorse et al. |
| 4,149,535 A | 4/1979 | Voider |
| 4,382,199 A | 5/1983 | Isaacson |
| 4,392,836 A | 7/1983 | Sugawara |
| 4,434,389 A | 2/1984 | Langley et al. |
| 4,507,048 A | 3/1985 | Belenger et al. |
| 4,528,485 A | 7/1985 | Boyd, Jr. |
| 4,540,402 A | 9/1985 | Aigner |
| 4,549,860 A | 10/1985 | Yakich |
| 4,645,961 A | 2/1987 | Maisky |
| 4,686,982 A | 8/1987 | Nash |
| 4,688,998 A | 8/1987 | Olsen et al. |
| 4,753,221 A | 6/1988 | Kensey et al. |
| 4,769,006 A | 9/1988 | Papatonakos |
| 4,779,614 A | 10/1988 | Moise |
| 4,790,843 A | 12/1988 | Carpentier et al. |
| 4,806,080 A | 2/1989 | Mizobuchi et al. |
| 4,817,586 A | 4/1989 | Wampler |
| 4,846,152 A | 7/1989 | Wampler et al. |
| 4,857,781 A | 8/1989 | Shih |
| 4,888,011 A | 12/1989 | Kung et al. |
| 4,895,557 A | 1/1990 | Moise et al. |
| 4,900,227 A | 2/1990 | Troup lin |
| 4,902,272 A | 2/1990 | Milder et al. |
| 4,906,229 A | 3/1990 | Wampler |
| 4,908,012 A | 3/1990 | Moise et al. |
| 4,919,647 A | 4/1990 | Nash |
| 4,930,997 A | 6/1990 | Bennett |
| 4,944,722 A | 7/1990 | Carriker et al. |
| 4,957,504 A | 9/1990 | Chardack |
| 4,964,864 A | 10/1990 | Summers et al. |
| 4,969,865 A | 11/1990 | Hwang et al. |
| 4,985,014 A | 1/1991 | Orejola |
| 4,995,857 A | 2/1991 | Arnold |
| 5,021,048 A | 6/1991 | Buckholtz |
| 5,078,741 A | 1/1992 | Bramm et al. |
| 5,092,844 A | 3/1992 | Schwartz et al. |
| 5,092,879 A | 3/1992 | Jarvik |
| 5,100,374 A | 3/1992 | Kageyama |
| 5,106,263 A | 4/1992 | Irie |
| 5,106,273 A | 4/1992 | Lemarquand et al. |
| 5,106,372 A | 4/1992 | Ranford |
| 5,112,202 A | 5/1992 | Oshima et al. |
| 5,112,349 A | 5/1992 | Summers et al. |
| 5,129,883 A | 7/1992 | Black |
| 5,145,333 A | 9/1992 | Smith |
| 5,147,186 A | 9/1992 | Buckholtz |
| 5,190,528 A | 3/1993 | Fonger et al. |
| 5,201,679 A | 4/1993 | Velte et al. |
| 5,211,546 A | 5/1993 | Isaacson et al. |
| 5,229,693 A | 7/1993 | Futami et al. |
| 5,275,580 A | 1/1994 | Yamazaki |
| 5,290,227 A | 3/1994 | Pasque |
| 5,290,236 A | 3/1994 | Mathewson |
| 5,300,112 A | 4/1994 | Barr |
| 5,306,295 A | 4/1994 | Kolff et al. |
| 5,312,341 A | 5/1994 | Turi |
| 5,313,128 A | 5/1994 | Robinson et al. |
| 5,332,374 A | 7/1994 | Kricker et al. |
| 5,346,458 A | 9/1994 | Afield |
| 5,350,283 A | 9/1994 | Nakazeki et al. |
| 5,354,331 A | 10/1994 | Schachar |
| 5,360,445 A | 11/1994 | Goldowsky |
| 5,370,509 A | 12/1994 | Golding et al. |
| 5,376,114 A | 12/1994 | Jarvik |
| 5,385,581 A | 1/1995 | Bramm et al. |
| 5,405,383 A | 4/1995 | Barr |
| 5,449,342 A | 9/1995 | Hirose et al. |
| 5,478,222 A | 12/1995 | Heidelberg et al. |
| 5,504,978 A | 4/1996 | Meyer, III |
| 5,507,629 A | 4/1996 | Jarvik |
| 5,519,270 A | 5/1996 | Yamada et al. |
| 5,533,957 A | 7/1996 | Aldea |
| 5,569,111 A | 10/1996 | Cho et al. |
| 5,575,630 A | 11/1996 | Nakazawa et al. |
| 5,588,812 A | 12/1996 | Taylor et al. |
| 5,595,762 A | 1/1997 | Derrieu et al. |
| 5,611,679 A | 3/1997 | Ghosh et al. |
| 5,613,935 A | 3/1997 | Jarvik |
| 5,630,836 A | 5/1997 | Prem et al. |
| 5,643,226 A | 7/1997 | Cosgrove et al. |
| 5,678,306 A | 10/1997 | Bozeman, Jr. et al. |
| 5,692,882 A | 12/1997 | Bozeman, Jr. et al. |
| 5,695,471 A | 12/1997 | Wampler |
| 5,708,346 A | 1/1998 | Schob |
| 5,725,357 A | 3/1998 | Nakazeki et al. |
| 5,738,649 A | 4/1998 | Macoviak |
| 5,746,575 A | 5/1998 | Westphal et al. |
| 5,746,709 A | 5/1998 | Rom et al. |
| 5,749,855 A | 5/1998 | Reitan |
| 5,755,784 A | 5/1998 | Jarvik |
| 5,776,111 A | 7/1998 | Tesio |
| 5,795,074 A | 8/1998 | Rahman et al. |
| 5,800,559 A | 9/1998 | Higham et al. |
| 5,807,311 A | 9/1998 | Palestrant |
| 5,814,011 A | 9/1998 | Corace |
| 5,824,069 A | 10/1998 | Lemole |
| 5,843,129 A | 12/1998 | Larson et al. |
| 5,851,174 A | 12/1998 | Jarvik et al. |
| 5,853,394 A | 12/1998 | Tolkoff et al. |
| 5,868,702 A | 2/1999 | Stevens et al. |
| 5,868,703 A | 2/1999 | Bertolero et al. |
| 5,890,883 A | 4/1999 | Golding et al. |
| 5,911,685 A | 6/1999 | Siess et al. |
| 5,917,295 A | 6/1999 | Mongeau |
| 5,917,297 A | 6/1999 | Gerster et al. |
| 5,921,913 A | 7/1999 | Siess |
| 5,924,848 A | 7/1999 | Izraelev |
| 5,924,975 A | 7/1999 | Goldowsky |
| 5,928,131 A | 7/1999 | Prem |
| 5,938,412 A | 8/1999 | Izraelev |
| 5,941,813 A | 8/1999 | Sievers et al. |
| 5,945,753 A | 8/1999 | Maegawa et al. |
| 5,947,703 A | 9/1999 | Nojiri et al. |
| 5,951,263 A | 9/1999 | Taylor et al. |
| 5,964,694 A | 10/1999 | Siess et al. |
| 5,984,892 A | 11/1999 | Bedingham |
| 6,004,269 A | 12/1999 | Crowley et al. |
| 6,007,479 A | 12/1999 | Rottenberg et al. |
| 6,030,188 A | 2/2000 | Nojiri et al. |

(56) References Cited

U.S. PATENT DOCUMENTS

| | | | |
|---|---|---|---|
| 6,042,347 | A | 3/2000 | Scholl et al. |
| 6,053,705 | A | 4/2000 | Schob et al. |
| 6,058,593 | A | 5/2000 | Siess |
| 6,066,086 | A | 5/2000 | Antaki et al. |
| 6,071,093 | A | 6/2000 | Hart |
| 6,074,180 | A | 6/2000 | Khanwilkar et al. |
| 6,080,133 | A | 6/2000 | Wampler |
| 6,082,900 | A | 7/2000 | Takeuchi et al. |
| 6,083,260 | A | 7/2000 | Aboul-Hosn et al. |
| 6,086,527 | A | 7/2000 | Talpade |
| 6,100,618 | A | 8/2000 | Schoeb et al. |
| 6,123,659 | A | 9/2000 | leBlanc et al. |
| 6,123,726 | A | 9/2000 | Mori et al. |
| 6,139,487 | A | 10/2000 | Siess |
| 6,142,752 | A | 11/2000 | Akamatsu et al. |
| 6,143,025 | A | 11/2000 | Stobie et al. |
| 6,146,325 | A | 11/2000 | Lewis et al. |
| 6,149,683 | A | 11/2000 | Lancisi et al. |
| 6,158,984 | A | 12/2000 | Cao et al. |
| 6,171,078 | B1 | 1/2001 | Schob |
| 6,176,822 | B1 | 1/2001 | Nix et al. |
| 6,176,848 | B1 | 1/2001 | Rau et al. |
| 6,179,773 | B1 | 1/2001 | Prem et al. |
| 6,190,304 | B1 | 2/2001 | Downey et al. |
| 6,200,260 | B1 | 3/2001 | Bolling |
| 6,206,659 | B1 | 3/2001 | Izraelev |
| 6,222,290 | B1 | 4/2001 | Schob et al. |
| 6,227,797 | B1 | 5/2001 | Watterson et al. |
| 6,227,820 | B1 | 5/2001 | Jarvik |
| 6,234,772 | B1 | 5/2001 | Wampler et al. |
| 6,234,998 | B1 | 5/2001 | Wampler |
| 6,245,007 | B1 | 6/2001 | Bedingham et al. |
| 6,247,892 | B1 | 6/2001 | Kazatchkov et al. |
| 6,249,067 | B1 | 6/2001 | Schob et al. |
| 6,254,359 | B1 | 7/2001 | Aber |
| 6,264,635 | B1 | 7/2001 | Wampler et al. |
| 6,268,675 | B1 | 7/2001 | Amrhein |
| 6,276,831 | B1 | 8/2001 | Takahashi et al. |
| 6,293,901 | B1 | 9/2001 | Prem |
| 6,295,877 | B1 | 10/2001 | Aboul-Hosn et al. |
| 6,319,231 | B1 | 11/2001 | Andrulitis |
| 6,320,731 | B1 | 11/2001 | Eeaves et al. |
| 6,351,048 | B1 | 2/2002 | Schob et al. |
| 6,355,998 | B1 | 3/2002 | Schob et al. |
| 6,365,996 | B2 | 4/2002 | Schob |
| 6,375,607 | B1 | 4/2002 | Prem |
| 6,387,037 | B1 | 5/2002 | Bolling et al. |
| 6,394,769 | B1 | 5/2002 | Bearnson et al. |
| 6,422,990 | B1 | 7/2002 | Prem |
| 6,425,007 | B1 | 7/2002 | Messinger |
| 6,428,464 | B1 | 8/2002 | Bolling |
| 6,439,845 | B1 | 8/2002 | Veres |
| 6,447,266 | B2 | 9/2002 | Antaki et al. |
| 6,447,441 | B1 | 9/2002 | Yu et al. |
| 6,458,163 | B1 | 10/2002 | Slemker et al. |
| 6,508,777 | B1 | 1/2003 | Macoviak et al. |
| 6,508,787 | B2 | 1/2003 | Erbel et al. |
| 6,517,315 | B2 | 2/2003 | Belady |
| 6,522,093 | B1 | 2/2003 | Hsu et al. |
| 6,532,964 | B2 | 3/2003 | Aboul-Hosn et al. |
| 6,533,716 | B1 | 3/2003 | Schmitz-Rode et al. |
| 6,544,216 | B1 | 4/2003 | Sammler et al. |
| 6,547,519 | B2 | 4/2003 | deBlanc et al. |
| 6,547,530 | B2 | 4/2003 | Ozaki et al. |
| 6,575,717 | B2 | 6/2003 | Ozaki et al. |
| 6,589,030 | B2 | 7/2003 | Ozaki |
| 6,595,762 | B2 | 7/2003 | Khanwilkar et al. |
| 6,605,032 | B2 | 8/2003 | Benkowski et al. |
| 6,609,883 | B2 | 8/2003 | Woodard et al. |
| 6,610,004 | B2 | 8/2003 | Viole et al. |
| 6,623,420 | B2 | 9/2003 | Reich et al. |
| 6,641,378 | B2 | 11/2003 | Davis et al. |
| 6,641,558 | B1 | 11/2003 | Aboul-Hosn et al. |
| 6,688,861 | B2 | 2/2004 | Wampler |
| 6,692,318 | B2 | 2/2004 | McBride |
| 6,698,097 | B1 | 3/2004 | Miura et al. |
| 6,709,418 | B1 | 3/2004 | Aboul-Hosn et al. |
| 6,716,157 | B2 | 4/2004 | Goldowsky |
| 6,716,189 | B1 | 4/2004 | Jarvik et al. |
| 6,732,501 | B2 | 5/2004 | Yu et al. |
| 6,749,598 | B1 | 6/2004 | Keren et al. |
| 6,776,578 | B2 | 8/2004 | Belady |
| 6,790,171 | B1 | 9/2004 | Griindeman et al. |
| 6,794,789 | B2 | 9/2004 | Siess et al. |
| 6,808,371 | B2 | 10/2004 | Niwatsukino et al. |
| 6,817,836 | B2 | 11/2004 | Nose et al. |
| 6,846,168 | B2 | 1/2005 | Davis et al. |
| 6,860,713 | B2 | 3/2005 | Hoover |
| 6,884,210 | B2 | 4/2005 | Nose et al. |
| 6,926,662 | B1 | 8/2005 | Aboul-Hosn et al. |
| 6,935,344 | B1 | 8/2005 | Aboul-Hosn et al. |
| 6,942,672 | B2 | 9/2005 | Heilman et al. |
| 6,949,066 | B2 | 9/2005 | Beamson et al. |
| 6,966,748 | B2 | 11/2005 | Woodard et al. |
| 6,974,436 | B1 | 12/2005 | Aboul-Hosn et al. |
| 6,991,595 | B2 | 1/2006 | Burke et al. |
| 7,010,954 | B2 | 3/2006 | Siess et al. |
| 7,011,620 | B1 | 3/2006 | Siess |
| 7,022,100 | B1 | 4/2006 | Aboul-Hosn et al. |
| 7,027,875 | B2 | 4/2006 | Siess et al. |
| 7,048,681 | B2 | 5/2006 | Tsubouchi et al. |
| 7,090,401 | B2 | 8/2006 | Rahman et al. |
| 7,112,903 | B1 | 9/2006 | Schob |
| 7,122,019 | B1 | 10/2006 | Kesten et al. |
| 7,128,538 | B2 | 10/2006 | Tsubouchi et al. |
| 7,156,802 | B2 | 1/2007 | Woodard et al. |
| 7,160,243 | B2 | 1/2007 | Medvedev |
| 7,172,551 | B2 | 2/2007 | Leasure |
| 7,175,588 | B2 | 2/2007 | Morello |
| 7,202,582 | B2 | 4/2007 | Eckert et al. |
| 7,241,257 | B1 | 7/2007 | Ainsworth et al. |
| 7,284,956 | B2 | 10/2007 | Nose et al. |
| 7,329,236 | B2 | 2/2008 | Kesten et al. |
| 7,331,921 | B2 | 2/2008 | Viole et al. |
| 7,335,192 | B2 | 2/2008 | Keren et al. |
| 7,393,181 | B2 | 7/2008 | McBride et al. |
| 7,431,688 | B2 | 10/2008 | Wampler et al. |
| 7,462,019 | B1 | 12/2008 | Allarie et al. |
| 7,467,930 | B2 | 12/2008 | Ozaki et al. |
| 7,470,246 | B2 | 12/2008 | Mori et al. |
| 7,476,077 | B2 | 1/2009 | Woodard et al. |
| 7,491,163 | B2 | 2/2009 | Viole et al. |
| 7,575,423 | B2 | 8/2009 | Wampler |
| 7,645,225 | B2 | 1/2010 | Medvedev et al. |
| 7,660,635 | B1 | 2/2010 | Verness et al. |
| 7,699,586 | B2 | 4/2010 | LaRose et al. |
| 7,731,675 | B2 | 6/2010 | Aboul-Hosn et al. |
| 7,748,964 | B2 | 7/2010 | Yaegashi et al. |
| 7,802,966 | B2 | 9/2010 | Wampler et al. |
| 7,841,976 | B2 | 11/2010 | McBride et al. |
| 7,888,242 | B2 | 2/2011 | Tanaka et al. |
| 7,934,909 | B2 | 5/2011 | Nuesser et al. |
| 7,972,122 | B2 | 7/2011 | LaRose et al. |
| 7,976,271 | B2 | 7/2011 | LaRose et al. |
| 7,997,854 | B2 | 8/2011 | LaRose et al. |
| 8,007,254 | B2 | 8/2011 | LaRose et al. |
| 8,096,935 | B2 | 1/2012 | Sutton et al. |
| 8,123,669 | B2 | 2/2012 | Siess et al. |
| 8,152,493 | B2 | 4/2012 | LaRose et al. |
| 8,177,703 | B2 | 5/2012 | Smith et al. |
| 8,226,373 | B2 | 7/2012 | Yaehashi |
| 8,282,359 | B2 | 10/2012 | Ayre et al. |
| 8,283,829 | B2 | 10/2012 | Yamamoto et al. |
| 8,366,381 | B2 | 2/2013 | Woodard et al. |
| 8,403,823 | B2 | 3/2013 | Yu et al. |
| 8,512,012 | B2 | 8/2013 | Akdis et al. |
| 8,535,211 | B2 | 9/2013 | Campbell et al. |
| 8,585,290 | B2 | 11/2013 | Bauer |
| 8,652,024 | B1 | 2/2014 | Yanai et al. |
| 8,686,674 | B2 | 4/2014 | Bi et al. |
| 8,770,945 | B2 | 7/2014 | Ozaki et al. |
| 8,821,365 | B2 | 9/2014 | Ozaki et al. |
| 8,827,661 | B2 | 9/2014 | Mori |
| 8,864,644 | B2 | 10/2014 | Yomtov |

(56) References Cited

U.S. PATENT DOCUMENTS

| | | |
|---|---|---|
| 8,968,174 B2 | 3/2015 | Yanai et al. |
| 9,067,005 B2 | 6/2015 | Ozaki et al. |
| 9,068,572 B2 | 6/2015 | Ozaki et al. |
| 9,109,601 B2 | 8/2015 | Mori |
| 9,132,215 B2 | 9/2015 | Ozaki et al. |
| 9,133,854 B2 | 9/2015 | Okawa et al. |
| 9,371,826 B2 | 6/2016 | Yanai et al. |
| 9,381,285 B2 | 7/2016 | Ozaki et al. |
| 9,382,908 B2 | 7/2016 | Ozaki et al. |
| 9,410,549 B2 | 8/2016 | Ozaki et al. |
| 2001/0039369 A1 | 11/2001 | Terentiev |
| 2002/0051711 A1 | 5/2002 | Ozaki |
| 2002/0058994 A1 | 5/2002 | Hill et al. |
| 2002/0094281 A1 | 7/2002 | Khanwilkar et al. |
| 2002/0095210 A1 | 7/2002 | Finnegan et al. |
| 2003/0023302 A1 | 1/2003 | Moe et al. |
| 2003/0045772 A1 | 3/2003 | Reich et al. |
| 2003/0072656 A1 | 4/2003 | Niwatsukino et al. |
| 2003/0144574 A1 | 7/2003 | Heilman et al. |
| 2003/0199727 A1 | 10/2003 | Burke |
| 2003/0236488 A1 | 12/2003 | Novak |
| 2003/0236490 A1 | 12/2003 | Novak |
| 2004/0007515 A1 | 1/2004 | Geyer |
| 2004/0015232 A1 | 1/2004 | Shu et al. |
| 2004/0024285 A1 | 2/2004 | Muckter |
| 2004/0030381 A1 | 2/2004 | Shu |
| 2004/0143151 A1 | 7/2004 | Mori et al. |
| 2004/0145337 A1 | 7/2004 | Morishita |
| 2004/0152944 A1 | 8/2004 | Medvedev et al. |
| 2004/0171905 A1 | 9/2004 | Yu et al. |
| 2004/0210305 A1 | 10/2004 | Shu et al. |
| 2004/0215050 A1 | 10/2004 | Morello |
| 2004/0263341 A1 | 12/2004 | Enzinna |
| 2005/0004418 A1 | 1/2005 | Morello |
| 2005/0008496 A1 | 1/2005 | Tsubouchi et al. |
| 2005/0025630 A1 | 2/2005 | Ayre et al. |
| 2005/0043665 A1 | 2/2005 | Vinci et al. |
| 2005/0073273 A1 | 4/2005 | Maslov et al. |
| 2005/0089422 A1 | 4/2005 | Ozaki et al. |
| 2005/0131271 A1 | 6/2005 | Benkowski et al. |
| 2005/0141887 A1 | 6/2005 | Lelkes |
| 2005/0194851 A1 | 9/2005 | Eckert et al. |
| 2005/0261543 A1 | 11/2005 | Abe et al. |
| 2005/0287022 A1 | 12/2005 | Yaegashi et al. |
| 2006/0024182 A1 | 2/2006 | Akdis et al. |
| 2006/0055274 A1 | 3/2006 | Kim |
| 2006/0127227 A1 | 6/2006 | Mehlhorn et al. |
| 2007/0073393 A1 | 3/2007 | Kung et al. |
| 2007/0078293 A1 | 4/2007 | Shambaugh, Jr. |
| 2007/0114961 A1 | 5/2007 | Schwarzkopf |
| 2007/0134993 A1 | 6/2007 | Tamez et al. |
| 2007/0189648 A1 | 8/2007 | Kita et al. |
| 2007/0213690 A1 | 9/2007 | Phillips et al. |
| 2007/0231135 A1 | 10/2007 | Wampler et al. |
| 2007/0282298 A1 | 12/2007 | Mason |
| 2007/0297923 A1 | 12/2007 | Tada |
| 2008/0007196 A1 | 1/2008 | Tan et al. |
| 2008/0021394 A1 | 1/2008 | LaRose et al. |
| 2008/0030895 A1 | 2/2008 | Obara et al. |
| 2008/0095648 A1 | 4/2008 | Wampler et al. |
| 2008/0119777 A1 | 5/2008 | Vinci et al. |
| 2008/0124231 A1 | 5/2008 | Yaegashi |
| 2008/0183287 A1 | 7/2008 | Ayre |
| 2008/0211439 A1 | 9/2008 | Yokota et al. |
| 2008/0281146 A1 | 11/2008 | Morello |
| 2009/0041595 A1 | 2/2009 | Garzaniti et al. |
| 2009/0060743 A1 | 3/2009 | McBride et al. |
| 2009/0074336 A1 | 3/2009 | Engesser et al. |
| 2009/0099406 A1 | 4/2009 | Salmonsen et al. |
| 2009/0171136 A1 | 7/2009 | Shambaugh, Jr. |
| 2009/0257693 A1 | 10/2009 | Aiello |
| 2009/0318834 A1 | 12/2009 | Fujiwara et al. |
| 2010/0168534 A1 | 7/2010 | Matsumoto et al. |
| 2010/0185280 A1 | 7/2010 | Ayre et al. |
| 2010/0222634 A1 | 9/2010 | Poirier |
| 2010/0234835 A1 | 9/2010 | Horikawa et al. |
| 2010/0256440 A1 | 10/2010 | Maher |
| 2010/0262039 A1 | 10/2010 | Fujiwara et al. |
| 2010/0266423 A1 | 10/2010 | Gohean et al. |
| 2010/0305692 A1 | 12/2010 | Thomas et al. |
| 2010/0324465 A1 | 12/2010 | Vinci et al. |
| 2011/0015732 A1 | 1/2011 | Kanebako |
| 2011/0112354 A1 | 5/2011 | Nishimura et al. |
| 2011/0118766 A1 | 5/2011 | Reichenbach et al. |
| 2011/0118829 A1 | 5/2011 | Hoarau et al. |
| 2011/0118833 A1 | 5/2011 | Reichenbach et al. |
| 2011/0129373 A1 | 6/2011 | Mori |
| 2011/0160519 A1 | 6/2011 | Arndt et al. |
| 2011/0218383 A1 | 9/2011 | Broen et al. |
| 2011/0218384 A1 | 9/2011 | Bachman et al. |
| 2011/0218385 A1 | 9/2011 | Bolyare et al. |
| 2011/0237978 A1 | 9/2011 | Fujiwara et al. |
| 2011/0243759 A1 | 10/2011 | Ozaki et al. |
| 2011/0318203 A1 | 12/2011 | Ozaki et al. |
| 2012/0003108 A1 | 1/2012 | Ozaki et al. |
| 2012/0016178 A1 | 1/2012 | Woodard et al. |
| 2012/0022645 A1 | 1/2012 | Burke |
| 2012/0035411 A1 | 2/2012 | LaRose et al. |
| 2012/0078030 A1 | 3/2012 | Bourque |
| 2012/0078031 A1 | 3/2012 | Burke et al. |
| 2012/0095281 A1 | 4/2012 | Reichenbach et al. |
| 2012/0130152 A1 | 5/2012 | Ozaki et al. |
| 2012/0226350 A1 | 9/2012 | Ruder et al. |
| 2012/0243759 A1 | 9/2012 | Fujisawa |
| 2012/0245681 A1 | 9/2012 | Casas et al. |
| 2012/0253103 A1 | 10/2012 | Robert |
| 2012/0308363 A1 | 12/2012 | Ozaki et al. |
| 2013/0030240 A1 | 1/2013 | Schima et al. |
| 2013/0121821 A1 | 5/2013 | Ozaki et al. |
| 2013/0158521 A1 | 6/2013 | Sobue |
| 2013/0170970 A1 | 7/2013 | Ozaki et al. |
| 2013/0178694 A1 | 7/2013 | Jeffery et al. |
| 2013/0225909 A1 | 8/2013 | Dormanen et al. |
| 2013/0243623 A1 | 9/2013 | Okawa et al. |
| 2013/0289334 A1 | 10/2013 | Badstibner et al. |
| 2014/0030122 A1 | 1/2014 | Ozaki et al. |
| 2014/0066690 A1 | 3/2014 | Siebenhaar et al. |
| 2014/0066691 A1 | 3/2014 | Siebenhaar |
| 2014/0100413 A1 | 4/2014 | Casas et al. |
| 2014/0107399 A1 | 4/2014 | Spence |
| 2014/0142367 A1 | 5/2014 | Ayre et al. |
| 2014/0155682 A1 | 6/2014 | Jeffery et al. |
| 2014/0200389 A1 | 7/2014 | Yanai et al. |
| 2014/0205467 A1 | 7/2014 | Yanai et al. |
| 2014/0241904 A1 | 8/2014 | Yanai et al. |
| 2014/0275721 A1 | 9/2014 | Yanai et al. |
| 2014/0275727 A1 | 9/2014 | Bonde et al. |
| 2014/0296615 A1 | 10/2014 | Franano |
| 2014/0309481 A1 | 10/2014 | Medvedev et al. |
| 2014/0314597 A1 | 10/2014 | Allaire et al. |
| 2014/0323796 A1 | 10/2014 | Medvedev et al. |
| 2014/0343352 A1 | 11/2014 | Ardt et al. |
| 2015/0017030 A1 | 1/2015 | Ozaki |
| 2015/0023803 A1 | 1/2015 | Fritz et al. |
| 2015/0078936 A1 | 3/2015 | Mori |
| 2015/0306290 A1 | 10/2015 | Rosenberg et al. |
| 2015/0367048 A1 | 12/2015 | Brown et al. |
| 2015/0374892 A1 | 12/2015 | Yanai et al. |
| 2016/0058929 A1 | 3/2016 | Medvedev et al. |
| 2016/0058930 A1 | 3/2016 | Medvedev et al. |
| 2016/0228628 A1 | 8/2016 | Medvedev et al. |
| 2016/0235898 A1 | 8/2016 | Yanai et al. |
| 2016/0235899 A1 | 8/2016 | Yu et al. |
| 2016/0235900 A1 | 8/2016 | Yanai et al. |
| 2016/0281720 A1 | 9/2016 | Yanai et al. |

FOREIGN PATENT DOCUMENTS

| | | |
|---|---|---|
| CN | 102239334 A | 11/2011 |
| CN | 102341600 A | 2/2012 |
| EP | 971212 A | 1/2000 |
| EP | 1113117 A2 | 7/2001 |
| EP | 1327455 A | 7/2003 |
| EP | 1430919 A1 | 6/2004 |

(56) References Cited

FOREIGN PATENT DOCUMENTS

| | | |
|---|---|---|
| EP | 1495773 A2 | 6/2004 |
| EP | 1495773 A3 | 11/2006 |
| EP | 1495773 B1 | 2/2009 |
| EP | 2298375 A1 | 3/2011 |
| EP | 2372160 A1 | 10/2011 |
| EP | 2405140 A1 | 1/2012 |
| EP | 2461465 A1 | 6/2012 |
| JP | 58/9535 | 1/1983 |
| JP | 61/293146 | 12/1986 |
| JP | H02-007780 U | 1/1990 |
| JP | H02-033590 U | 3/1990 |
| JP | 04/091396 A | 3/1992 |
| JP | 04/148094 A | 5/1992 |
| JP | 05/021197 U | 3/1993 |
| JP | 06/014538 U | 2/1994 |
| JP | 06/053790 U | 7/1994 |
| JP | 2006/070476 | 9/1994 |
| JP | 2006/245455 | 9/1994 |
| JP | 07/014220 U | 3/1995 |
| JP | 07/042869 U | 8/1995 |
| JP | 07/509156 A | 10/1995 |
| JP | 09/122228 A | 5/1997 |
| JP | 10/331841 A | 12/1998 |
| JP | 11/244377 A | 9/1999 |
| JP | 2001/309628 | 11/2001 |
| JP | 2003/135592 A | 5/2003 |
| JP | 2004/166401 A | 6/2004 |
| JP | 2004/209240 A | 7/2004 |
| JP | 2004/332566 A | 11/2004 |
| JP | 2004/346925 A | 12/2004 |
| JP | 2005/094955 | 4/2005 |
| JP | 2005/127222 A | 5/2005 |
| JP | 2005/245138 | 9/2005 |
| JP | 2005/270345 A | 10/2005 |
| JP | 2005/270415 A | 10/2005 |
| JP | 2005/287599 A | 10/2005 |
| JP | 2006/167173 A | 6/2006 |
| JP | 2007/002885 A | 1/2007 |
| JP | 2007/043821 | 2/2007 |
| JP | 2007/089972 A | 4/2007 |
| JP | 2007/089974 | 4/2007 |
| JP | 2007/215292 | 8/2007 |
| JP | 2007/247489 | 9/2007 |
| JP | 2008/011611 | 1/2008 |
| JP | 2008/104278 | 5/2008 |
| JP | 2008/132131 | 6/2008 |
| JP | 2008/99453 | 8/2008 |
| JP | 2008/193838 | 8/2008 |
| JP | 2008/297997 A | 12/2008 |
| JP | 2008/301634 | 12/2008 |
| JP | 2006/254619 | 9/2009 |
| JP | 2010/133381 A | 6/2010 |
| JP | 2010/136863 A | 6/2010 |
| JP | 2012/021413 | 2/2012 |
| WO | 93/07388 A1 | 4/1993 |
| WO | 94/14226 | 6/1994 |
| WO | 96/31934 | 10/1996 |
| WO | 97/42413 A1 | 11/1997 |
| WO | 00/64509 A1 | 11/2000 |
| WO | 2005/011087 A1 | 2/2005 |
| WO | 2005/028000 A1 | 3/2005 |
| WO | 2005/034312 A2 | 4/2005 |
| WO | 2009/157408 A1 | 12/2009 |
| WO | 2010/067682 A1 | 6/2010 |
| WO | 2010/101082 A1 | 9/2010 |
| WO | 2010/101107 A1 | 9/2010 |
| WO | 2011/013483 A1 | 2/2011 |
| WO | 2012/036059 A1 | 3/2012 |
| WO | 2012/047550 A1 | 4/2012 |

OTHER PUBLICATIONS

Asama, J., et al., "A New Design for a Compact Centrifugal Blood Pump with a Magnetically Levitated Rotor", Asaio Jopurnal, vol. 50, No. 6, Nov. 1, 2004 (Nov. 1, 2004), pp. 550-556.

Asama, et al., "Suspension Performance of a Two-Axis Actively Regulated Consequent-Pole Bearingless Motor," IEEE Transactions On Energy Conversion, vol. 28, No. 4, Dec. 2013, 8 pages.

European Search report Issued in European Patent Application No. 10748702.7, mailed Apr. 2, 2013.

Extended European Search Report issued in European Patent Application No. EP 10748677.1, mailed Nov. 19, 2012.

Extended European Search Report issued in European Patent Application No. EP 11825062.0, mailed Jun. 18, 2015, all pages.

Extended European Search Report issued in European Patent Application No. EP 11806627.3, mailed Oct. 8, 2014, all pages.

Extended European Search Report issued on Mar. 26, 2015 in European Patent Application No. EP 09770118.9 filed Jun. 22, 2009, all pages.

International Search Report (PCT/ISA/210) issued on Jul. 14, 2009, by Japanese Patent Office as the International Searching Authority for International Application No. PCT/JP2009/061318.

International Search Report and Written Opinion issued in PCT/JP2011/050925, mailed Apr. 12, 2011.

International Search Report and Written Opinion issued in PCT/JP2011/054134, mailed Apr. 12, 2011.

International Search Report and Written Opinion issued in PCT/JP2011/064768, mailed Sep. 13, 2011.

International Search Report and Written Opinion issued in PCT/JP2011/070450, mailed Dec. 13, 2011.

International Search Report and Written Opinion of PCT/US2014/012448 mailed on Feb. 19, 2014, all pages.

International Search Report and Written Opinion of PCT/US2014/011786 mailed on May 5, 2014, all pages.

International Search Report and Written Opinion of PCT/US2014/012502 dated May 9, 2014, all pages.

International Search Report and Written Opinion of PCT/US2014/012511 mailed on May 14, 2014, all pages.

International Search Report and Written Opinion of PCT/US2014/017932 mailed on Jun. 16, 2014, all pages.

International Preliminary Report on Patentability mailed on Aug. 6, 2015 for International Patent Application No. PCT/US2014/012511 filed on Jan. 22, 2014; all pages.

International Preliminary Report on Patentability mailed on Feb. 25, 2016 for International Patent Application No. PCT/US2014/035798 filed on Apr. 29, 2014, all pages.

Kosaka, et al., "Operating Point Control System for a Continuous Flow Artificial Heart: In Vitro Study," ASAIO Journal 2003, all pages.

Neethu, S., et al., "Novel design, optimization and realization of axial flux motor for implantable blood pump", Power Electronics, Drives and Energy Systems (PEDES) & 2010 Power Indian, 2010 Joint International Conference on, IEEE, Dec. 20, 2010 (Dec. 20, 2010), pp. 1-6.

Sandtner, J., et al., "Electrodynamic Passive Magnetic Bearing with Planar Halbach Arrays", Aug. 6, 2004 (Aug. 6, 2004), retrieved from the internet: <http://www.silphenix.ch/lexington.pdf>, all pages.

Supplementary European Search Report issued in European Application No. 09831788.6, dated Jan. 7, 2013, all pages.

Terumo Heart, Inc., "Handled With Care—Significantly Reduce the Risk of Cell Damage," Terumo brochure, Apr. 2010, all pages.

Yarnazaki, et al., "Development of a Miniature Intraventricular Axial Flow Blood Pump," ASAIO Journal, 1993, all pages.

European office action mailed on Jul. 22, 2016 for European Patent Application No. EP 09770118.9, all pages.

European office action mailed on Jan. 27, 2016 for EP 10804230.0, all pages.

European office action mailed Sep. 8, 2016 for EP 14741174, all pages.

Extended European Search Report mailed on Feb. 4, 2016 in European Patent Application No. EP 12764433.4, filed Mar. 12, 2012, all pages.

Extended European Search Report for EP 14 74 3371 dated Sep. 29, 2016, all pages.

(56) References Cited

OTHER PUBLICATIONS

International Preliminary Report on Patentability mailed on Jul. 30, 2015 for International Patent Application No. PCT/US2014/011786, filed on Jan. 16, 2014, all pages.
International Preliminary Report on Patentability mailed on Aug. 6, 2015 for International Patent Application No. PCT/US2014/012511, filed on Jan. 22, 2014, all pages.
International Preliminary Report on Patentability mailed on Aug. 6, 2015 for International Patent Application No. PCT/US2014/012502, filed on Jan. 22, 2014, all pages.
International Preliminary Report on Patentability mailed on Sep. 11, 2015 for International Patent Application No. PCT/US2014/017932, filed on Feb. 24, 2014, all pages.
International Search Report and Written Opinion of PCT/US2014/035798, mailed on Feb. 11, 2016, all pages.
International Search Report and Written Opinion of PCT/US2016/017611, mailed on May 16, 2016, all pages.
International Search Report and Written Opinion of PCT/US2016/017791, mailed on May 16, 2016, all pages.
International Search Report and Written Opinion of PCT/US2016/017812, mailed on Jun. 7, 2016, all pages.
International Search Report and Written Opinion of PCT/US2016/017864, mailed Jun. 8, 2016, all pages.
International Search Report and Written Opinion of PCT/US2015/046844, mailed Oct. 27, 2015, all pages.
International Search Report and Written Opinion of PCT/US2015/046846, mailed Oct. 27, 2015, all pages.
Japanese office action mailed on Dec. 8, 2015 JP 2013-507344, all pages.
Decision to Grant for JP 2013-507344 issued Jun. 14, 2016, all pages.

CENTRIFUGAL PUMP APPARATUS

CROSS-REFERENCE TO RELATED APPLICATION

This application is a divisional of U.S. application Ser. No. 13/822,220, filed on Mar. 11, 2013, which is the U.S. National Phase Application under 35 U.S.C. §371 of International Application No. PCT/JP2011/070450, filed on Sep. 8, 2011, which in turn claims the benefit of Japanese Application No. 2010-205787, filed on Sep. 14, 2010, the disclosures of which are incorporated herein by reference in their entireties.

TECHNICAL FIELD

The present invention relates to a centrifugal pump apparatus, and particularly to a centrifugal pump apparatus including an impeller for delivering fluid by centrifugal force during rotation.

BACKGROUND ART

In recent years, canned motors having a structure including a motor drive chamber and a rotor chamber separated from each other by a dividing wall have been widely used. Such motor is used for a pump for transporting pure water in a semiconductor manufacturing line used in an environment that avoids dust, and a pump for transporting a biological solution, for example. Pumps for transporting a biological solution include a centrifugal blood pump apparatus using a direct drive motor for directly transmitting torque to an impeller in a blood chamber. This centrifugal blood pump apparatus can eliminate physical contact between the blood chamber and the outside to prevent invasion of bacteria and the like into blood, and is thus used as an artificial heart. Since an artificial heart is driven by electric power from a battery, enhancement of motor efficiency is critical.

A centrifugal blood pump in Japanese Patent Laying-Open No. 2004-209240 (PTL 1) includes a housing having first to third chambers partitioned from one another by first and second dividing walls, an impeller rotatably provided in the second chamber (blood chamber), a magnetic element provided in one surface of the impeller, an electromagnet provided in the first chamber to face the one surface of the impeller, a permanent magnet provided in the other surface of the impeller, a rotor and a motor provided in the third chamber, and a permanent magnet provided in the rotor to face the other surface of the impeller. A groove for hydrodynamic bearing is formed in a surface of the second dividing wall facing the other surface of the impeller. Owing to attractive force acting on the one surface of the impeller from the electromagnet, attractive force acting on the other surface of the impeller from the permanent magnet in the rotor, and a hydrodynamic bearing effect of the groove for hydrodynamic bearing, the impeller moves away from an inner surface of the second chamber and rotates without contacting.

A centrifugal blood pump in Japanese Patent Laying-Open No. 2006-167173 (PTL 2) includes a housing having first to third chambers partitioned from one another by first and second dividing walls, an impeller rotatably provided in the second chamber (blood chamber), a magnetic element provided in one surface of the impeller, a first permanent magnet provided in the first chamber to face the one surface of the impeller, a second permanent magnet provided in the other surface of the impeller, a rotor and a motor provided in the third chamber, and a third permanent magnet provided in the rotor to face the other surface of the impeller. A first groove for hydrodynamic bearing is formed in a surface of the first dividing wall facing the one surface of the impeller, and a second groove for hydrodynamic bearing is formed in a surface of the second dividing wall facing the other surface of the impeller. Owing to attractive force acting on the one surface of the impeller from the first permanent magnet, attractive force acting on the other surface of the impeller from the third permanent magnet in the rotor, and a hydrodynamic bearing effect of the first and second grooves for hydrodynamic bearing, the impeller moves away from an inner surface of the second chamber and rotates without contacting.

A turbo-type pump in FIGS. 8 and 9 of Japanese Patent Laying-Open No. 4-91396 (PTL 3) includes a housing, an impeller rotatably provided in the housing, a first permanent magnet provided in one surface of the impeller, a rotor provided outside the housing, a second permanent magnet provided in the rotor to face the one surface of the impeller, a third permanent magnet provided in the other surface of the impeller, and a magnetic element provided in the housing to face the other surface of the impeller. A first groove for hydrodynamic bearing is formed in the one surface of the impeller, and a second groove for hydrodynamic bearing is formed in the other surface of the impeller. Owing to attractive force acting on the one surface of the impeller from the second permanent magnet in the rotor, attractive force acting on the other surface of the impeller from the magnetic element in the housing, and a hydrodynamic bearing effect of the first and second grooves for hydrodynamic bearing, the impeller moves away from an inner surface of the housing and rotates without contacting.

A clean pump in Japanese Utility Model Laying-Open No. 6-53790 (PTL 4) includes a casing, an impeller rotatably provided in the casing, a first permanent magnet provided in one surface of the impeller, a rotor provided outside the casing, a second permanent magnet provided in the rotor to face the one surface of the impeller, a magnetic element provided in the other surface of the impeller, and an electromagnet provided outside the housing to face the other surface of the impeller. A groove for hydrodynamic bearing is formed in the one surface of the impeller. The electromagnet is actuated when a rotation speed of the impeller is lower than a prescribed rotation speed, and power supply to the electromagnet is stopped when the rotation speed of the impeller becomes higher than the prescribed rotation speed. Owing to attractive force acting on the one surface of the impeller from the second permanent magnet in the rotor and a hydrodynamic bearing effect of the groove for hydrodynamic bearing, the impeller moves away from an inner surface of the housing and rotates without contacting.

CITATION LIST

Patent Literature

PTL 1: Japanese Patent Laying-Open No. 2004-209240
PTL 2: Japanese Patent Laying-Open No. 2006-167173
PTL 3: Japanese Patent Laying-Open No. 4-91396
PTL 4: Japanese Utility Model Laying-Open No. 6-53790

SUMMARY OF INVENTION

Technical Problem

Unfortunately, in a canned motor having a dividing wall provided between a stator and a rotor, there is a large gap between the stator and the rotor, resulting in difficulty in increasing torque and enhancing efficiency. Particularly, it is difficult to enhance efficiency of a small motor due to its low degree of design flexibility by dimensional restrictions and the like, and its susceptibility to local magnetic saturation. For this reason, in order to enhance efficiency, a structure including stacked silicon steel plate is used for a magnetic path to reduce iron loss. The efficiency can also be improved by varying the shape of a core to increase an occupancy rate of a coil.

The pumps in PTLs 1 to 4 described above are common in the feature of axially supporting the impeller by the grooves for hydrodynamic bearing formed in a portion where the impeller and the housing face each other, and radially supporting the impeller by the attractive force between the permanent magnet provided in the impeller and the permanent magnet provided outside the housing.

Supporting rigidity of a groove for hydrodynamic bearing is proportionate to a rotation speed of an impeller. Thus, in order for an impeller to stably rotate without contacting a housing even when a disturbance is applied to a pump, axial rigidity for the impeller needs to be enhanced by increasing a normal rotation speed range of the pump. In the pumps of PTLs 1 to 4 described above, however, the impeller is radially supported by utilizing the attractive force of the permanent magnets, and so the supporting rigidity is low, resulting in inability to rotate the impeller at high speed.

One way to increase the radial rigidity is to increase the attractive force between the permanent magnet in the impeller and the permanent magnet or a stator provided outside the housing. As the attractive force is increased, however, a negative axial rigidity value of the impeller increases (namely, as the impeller moves axially, the attractive force increases correspondingly). Thus, supporting performance on the impeller by hydrodynamic force and the attractive force acting between the impeller and the housing increase, resulting in difficulty in smoothly driving the impeller to rotate.

Furthermore, if the negative axial rigidity value of the impeller is higher than positive rigidity resulting from hydrodynamic force, stable rotation cannot be obtained. If radial support is provided by a passive magnetic bearing with a permanent magnet, radial rigidity is determined by a negative axial rigidity value. It is thus difficult to improve the radial rigidity under conditions for realizing stable rotation, while the mass of the impeller must not be increased in order for the impeller to rotate without contacting the housing.

In particular, when an impeller is rotated by magnetic interaction between an outside motor coil and a permanent magnet provided in the impeller as shown in FIG. 39 of PTL 2, starting torque is smaller than in an example where an impeller is driven to rotate through magnetic coupling between permanent magnets as shown in FIG. 3 of PTL 2. It is thus difficult to smoothly drive the impeller to rotate. This is because this centrifugal blood pump has a canned motor structure in which the impeller rotatably provided in the second chamber (blood chamber) is rotated by the motor with respect to the housing including the first to third chambers partitioned from one another by the first and second dividing walls, and thus has a wide motor gap. Thus, a large current is required to generate starting torque. Improvement in motor efficiency is necessary to reduce a current during activation and to reduce power consumption during rated rotation, and is critical particularly in driving a battery.

One way to further reduce the size of a motor is to minimize a motor gap to increase a torque constant. If the size of this pump structure is reduced, however, increase in axial attractive force and increase in negative rigidity value due to the reduced motor gap makes it difficult to stably rotate an impeller. Furthermore, the area of a hydrodynamic bearing becomes smaller due to the size reduction of the pump, causing a generated hydrodynamic force (positive rigidity) to become extremely small. Therefore, as the size of this pump structure is reduced, the axial attractive force and the negative rigidity value need to be lowered.

In other words, when reducing the size of this pump, it is difficult to lower the axial attractive force and the negative rigidity value while securing required motor torque.

In view of the above, a main object of the present invention is to provide a small centrifugal pump capable of lowering axial attractive force while securing required motor torque.

Solution to Problem

A centrifugal pump according to the present invention is a centrifugal pump apparatus including a housing having first and second chambers partitioned from each other by a dividing wall, an impeller rotatably provided in the first chamber along the dividing wall, for delivering fluid by centrifugal force during rotation, and a drive unit provided in the second chamber for driving the impeller to rotate with the dividing wall being interposed, and includes a first magnetic element provided in one surface of the impeller, a second magnetic element provided in an inner wall of the first chamber facing the one surface of the impeller, for attracting the first magnetic element, and a plurality of third magnetic elements provided in the other surface of the impeller, arranged in a direction of rotation of the impeller, and attracted by the drive unit. The drive unit includes a plurality of coils provided to face the plurality of third magnetic elements, for generating rotating magnetic field, and a plurality of fourth magnetic elements provided in correspondence with the plurality of coils respectively and each inserted in the corresponding coil, and each fourth magnetic element is shorter than the corresponding coil in a direction of a central axis of the impeller. During rotation of the impeller, first attractive force between the first and second magnetic elements and second attractive force between the plurality of third magnetic elements and the plurality of fourth magnetic elements are balanced with each other substantially in a center of a movable range of the impeller in the first chamber. A first groove for hydrodynamic bearing is formed in one surface of the impeller or in the inner wall of the first chamber facing the one surface, and a second groove for hydrodynamic bearing is formed in the other surface of the impeller or in the dividing wall facing the other surface.

As a result, the impeller can be rotated at high speed by rotational torque obtained through magnetic coupling between the fourth magnetic elements of the drive unit and the third magnetic elements of the impeller, and rotational torque obtained through magnetic coupling between the coils longer than the fourth magnetic elements and the third magnetic elements. In addition, required rotational torque can be generated while the size of the pump is reduced.

Moreover, since the fourth magnetic elements are made shorter than the coils, a large gap can be set between the third and fourth magnetic elements, to lower the attractive force between the third and fourth magnetic elements.

Therefore, axial attractive force and negative rigidity can be lowered while required torque is satisfied.

Preferably, the drive unit further includes a disc-shaped fifth magnetic element. The plurality of coils are provided between the dividing wall and the fifth magnetic element, and the plurality of fourth magnetic elements are joined to the fifth magnetic element.

Preferably, surfaces facing each other of every two adjacent fourth magnetic elements are provided substantially in parallel to each other. In this case, a large space for the coils can be secured and turns of the coils can be increased. In addition, a radial length of the coils can be increased to increase the Lorentz force.

Preferably, each fourth magnetic element is formed in a cylindrical shape. In this case, a large space for the coils can be secured and turns of the coils can be increased. Thus, copper loss that occurs in the motor coils can be reduced, thereby enhancing energy efficiency when the impeller is driven to rotate.

Preferably, each fourth magnetic element includes a plurality of steel plates stacked in the direction of rotation of the impeller. In this case, eddy current loss that occurs in the fourth magnetic elements can be reduced, thereby enhancing energy efficiency when the impeller is driven to rotate.

Preferably, each fourth magnetic element includes a plurality of steel plates stacked in a radial direction of the impeller. In this case, eddy current loss that occurs in the fourth magnetic elements can be reduced, thereby enhancing energy efficiency when the impeller is driven to rotate.

Preferably, each fourth magnetic element is made of pure iron, soft iron, or ferrosilicon. In this case, iron loss in the fourth magnetic elements can be reduced, thereby enhancing energy efficiency when the impeller is driven to rotate.

Preferably, each fourth magnetic element is made of powders of pure iron, soft iron, or ferrosilicon. In this case, iron loss in the fourth magnetic elements can further be reduced, thereby enhancing energy efficiency when the impeller is driven to rotate.

Preferably, each fourth magnetic element includes a strip-shaped magnetic steel plate wound a plurality of times around a center line. In this case, iron loss in the fourth magnetic elements can be reduced, thereby enhancing energy efficiency when the impeller is driven to rotate.

Another centrifugal pump according to the present invention is a centrifugal pump apparatus including a housing having first and second chambers partitioned from each other by a dividing wall, an impeller rotatably provided in the first chamber along the dividing wall, for delivering fluid by centrifugal force during rotation, and a drive unit provided in the second chamber for driving the impeller to rotate with the dividing wall being interposed, and includes a plurality of first magnetic elements provided in the impeller, arranged in a direction of rotation of the impeller, and attracted by the drive unit. The drive unit includes a plurality of coils provided to face the plurality of first magnetic elements, for generating rotating magnetic field, and a plurality of second magnetic elements provided in correspondence with the plurality of coils respectively and each inserted in the corresponding coil, and each second magnetic element is shorter than the corresponding coil in a direction of a central axis of the impeller. A first groove for hydrodynamic bearing is formed in one surface of the impeller or in the inner wall of the first chamber facing the one surface, and a second groove for hydrodynamic bearing is formed in the other surface of the impeller or in the dividing wall facing the other surface. During rotation of the impeller, force which is the sum of hydrodynamic force during rated rotation generated by the first groove for hydrodynamic bearing and attractive force between the plurality of first magnetic elements and the plurality of second magnetic elements, and hydrodynamic force during rated rotation generated by the second groove for hydrodynamic bearing are balanced with each other substantially in a center of a movable range of the impeller in the first chamber.

Preferably, the drive unit further includes a disc-shaped third magnetic element. The plurality of coils are provided between the dividing wall and the third magnetic element, and the plurality of second magnetic elements are joined to the third magnetic element.

Preferably, a third groove for hydrodynamic bearing is formed in an outer circumferential surface of the impeller or in an inner circumferential surface of the first chamber facing the outer circumferential surface.

Yet another centrifugal pump apparatus according to the present invention is a centrifugal pump apparatus including a housing having first and second dividing walls and a fluid chamber therebetween, an impeller rotatably provided in the fluid chamber along the first and second dividing walls, for delivering fluid by centrifugal force during rotation, and first and second drive units provided outside the fluid chamber, for driving the impeller to rotate with the first and second dividing walls being interposed, respectively, and includes a plurality of first magnetic elements provided in the impeller, arranged in a direction of rotation of the impeller, and attracted by the first and second drive units. Each of the first and second drive units includes a plurality of coils provided to face the plurality of first magnetic elements, for generating rotating magnetic field, and a plurality of second magnetic elements provided in correspondence with the plurality of coils respectively and each inserted in the corresponding coil, and each second magnetic element is shorter than the corresponding coil in a direction of a central axis of the impeller. During rotation of the impeller, first attractive force between the plurality of first magnetic elements and the plurality of second magnetic elements of the first drive unit and second attractive force between the plurality of first magnetic elements and the plurality of second magnetic elements of the second drive unit are balanced with each other substantially in a center of a movable range of the impeller in the fluid chamber. A first groove for hydrodynamic bearing is formed in one surface of the impeller or in the first dividing wall facing the one surface, and a second groove for hydrodynamic bearing is formed in the other surface of the impeller or in the second dividing wall facing the other surface.

Preferably, each of the first and second drive units further includes a disc-shaped third magnetic element. The plurality of coils of the first drive unit are provided between the first dividing wall and the third magnetic element of the first drive unit. The plurality of coils of the second drive unit are provided between the second dividing wall and the third magnetic element of the second drive unit. In each of the first and second drive units, the plurality of second magnetic elements are joined to the third magnetic element.

Preferably, a third groove for hydrodynamic bearing is formed in an outer circumferential surface of the impeller or in an inner circumferential surface of the fluid chamber facing the outer circumferential surface.

Preferably, the fluid is blood, and the centrifugal pump apparatus is used for circulating the blood. In this case, the impeller is smoothly activated to rotate to secure a distance between the impeller and the housing, thus preventing occurrence of hemolysis.

Advantageous Effects of Invention

As described above, according to the present invention, an impeller can be rotated at high speed while the size of a pump is reduced, to increase force in activating the impeller to rotate. Moreover, axial attractive force acting on the impeller can be suppressed while torque for driving the impeller to rotate is maintained. Furthermore, energy efficiency can be enhanced when the impeller is driven to rotate.

DESCRIPTION OF EMBODIMENTS

First Embodiment

Figure 1:
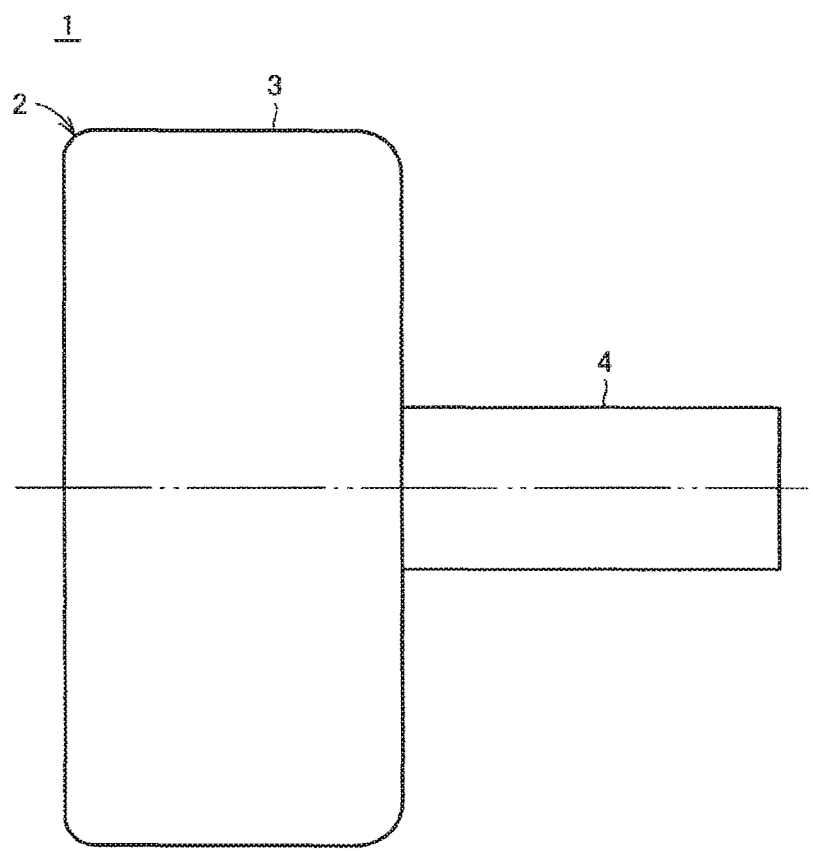
FIG. 1 is a front view showing the appearance of a pump unit of a centrifugal blood pump apparatus according to a first embodiment of the present invention.
Figure 2:
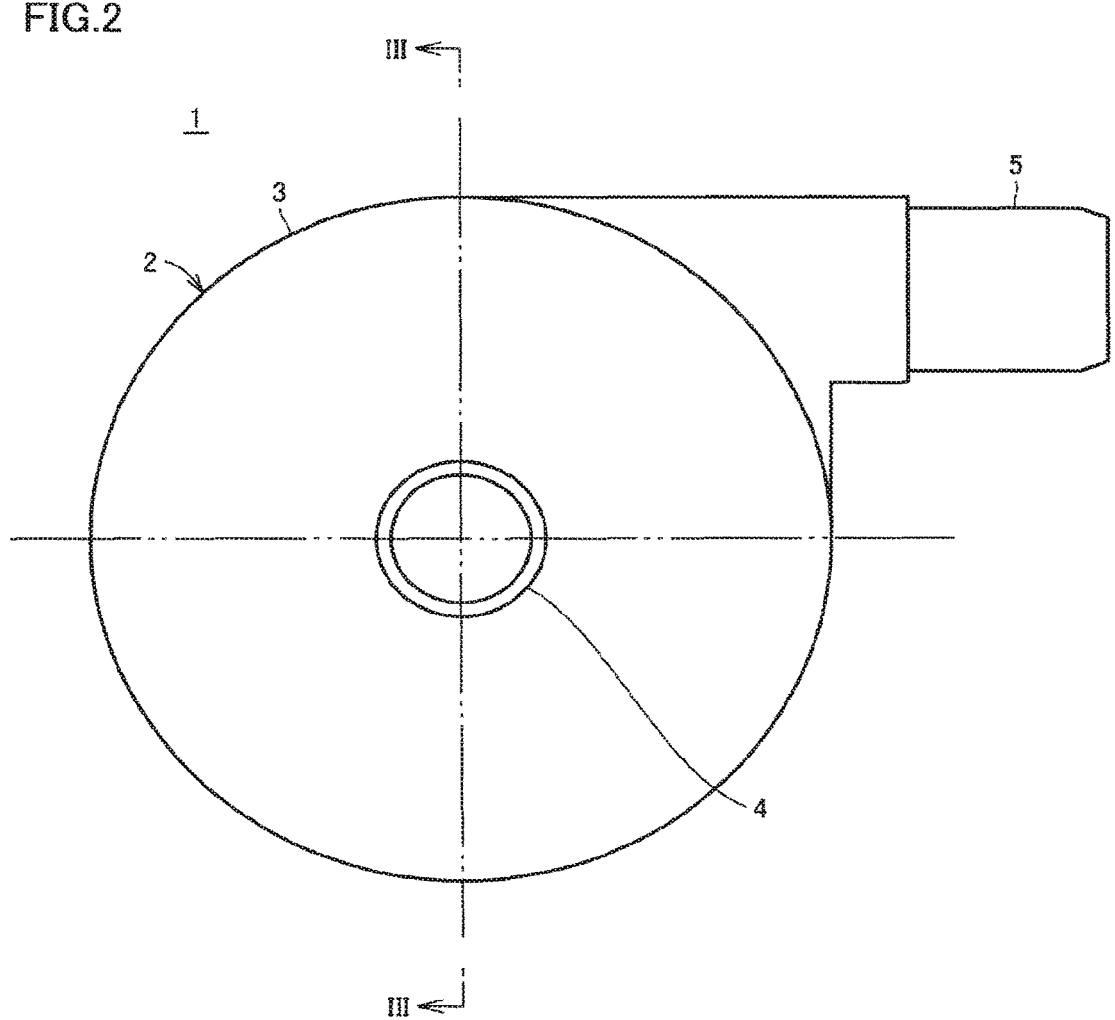
FIG. 2 is a side view of the pump unit shown in FIG. 1.

In FIGS. 1 to 7, a pump unit 1 of this centrifugal blood pump apparatus includes a housing 2 made of a nonmagnetic material. Housing 2 includes a cylindrical body portion 3, a cylindrical blood inlet port 4 provided to stand at a center of one end surface of body portion 3, and a cylindrical blood outlet port 5 provided on an outer circumferential surface of body portion 3. Blood outlet port 5 extends in a tangential direction of the outer circumferential surface of body portion 3.

Figure 3:
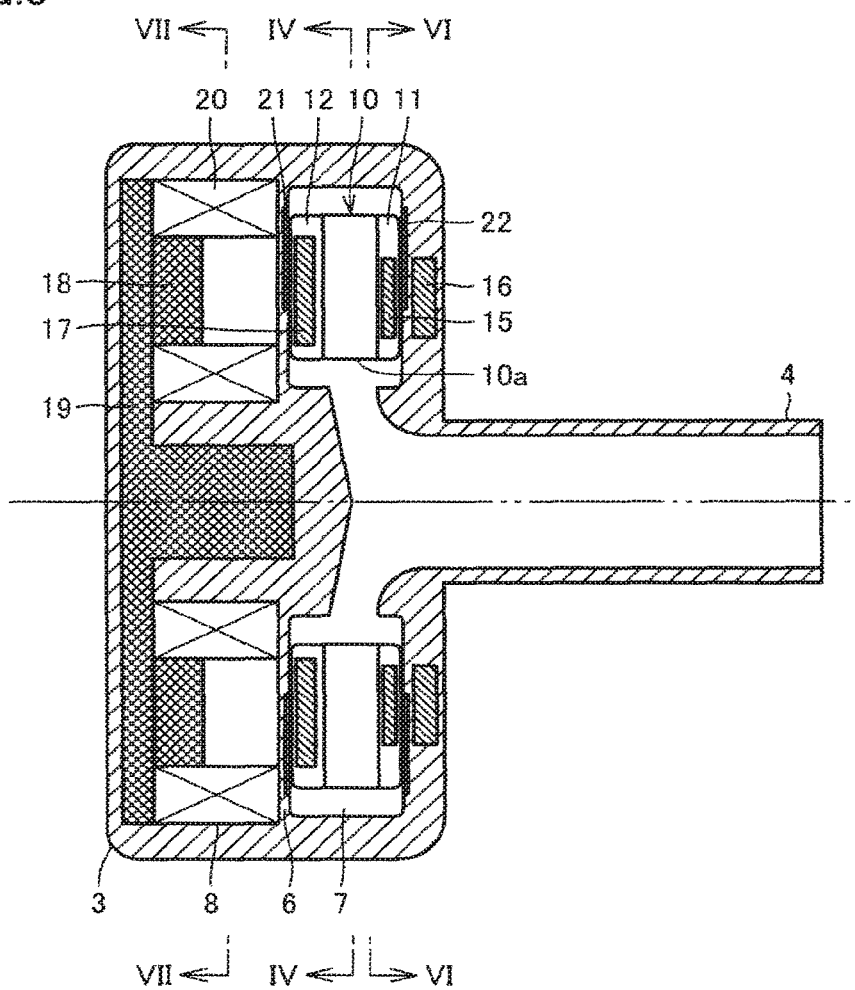
FIG. 3 is a cross-sectional view along the line in FIG. 2.
Figure 4:
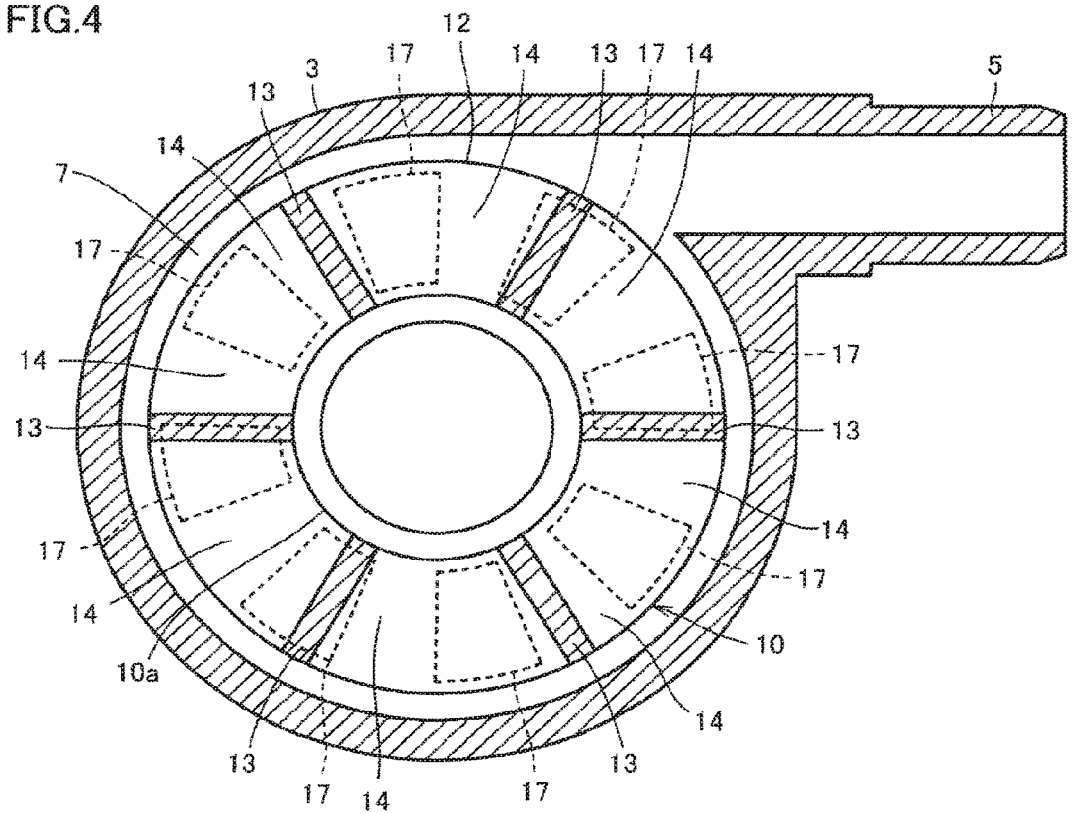
FIG. 4 is a cross-sectional view along the line IV-IV in FIG. 3.

In housing 2, as shown in FIG. 3, a blood chamber 7 and a motor chamber 8 partitioned from each other by a dividing wall 6 are provided. In blood chamber 7, as shown in FIGS. 3 and 4, a disc-shaped impeller 10 having a through hole 10a in a center thereof is rotatably provided. Impeller 10 includes two shrouds 11, 12 in a doughnut plate shape, and a plurality of (e.g., six) vanes 13 formed between two shrouds 11 and 12. Shroud 11 is arranged on the blood inlet port 4 side, and shroud 12 is arranged on the dividing wall 6 side. Shrouds 11, 12 and vanes 13 are made of a nonmagnetic material.

A plurality of (six in this case) blood passages 14 partitioned from one another by the plurality of vanes 13 are formed between two shrouds 11 and 12. As shown in FIG. 4, blood passage 14 is in communication with through hole 10a at the center of impeller 10, and extends with through hole 10a of impeller 10 as a starting point to an outer circumference such that blood passage 14 gradually increases in width. In other words, vane 13 is formed between two adjacent blood passages 14. In the first embodiment, the plurality of vanes 13 are provided at regular angular intervals, and they have the same shape. Thus, the plurality of blood passages 14 are provided at regular angular intervals, and they have the same shape.

When impeller 10 is driven to rotate, blood that has flowed in through blood inlet port 4 is delivered by centrifugal force from through hole 10a to an outer circumferential portion of impeller 10 via blood passages 14, and flows out through blood outlet port 5.

A permanent magnet 15 is embedded in shroud 11, and a permanent magnet 16 for attracting permanent magnet 15 is embedded in an inner wall of blood chamber 7 facing shroud 11. Permanent magnets 15, 16 are provided to attract (in other words, bias) impeller 10 to the side opposite to motor chamber 8, that is, toward blood inlet port 4.

Instead of providing permanent magnets 15, 16 in shroud 11 and in the inner wall of blood chamber 7, respectively, a permanent magnet may be provided in one of shroud 11 and the inner wall of blood chamber 7, and a magnetic element may be provided in the other. Alternatively, shroud 11 itself may be formed of permanent magnet 15 or a magnetic element. Either a soft magnetic element or a hard magnetic element may be used as the magnetic element.

A single permanent magnet 16 or a plurality of permanent magnets 16 may be provided. If a single permanent magnet 16 is provided, permanent magnet 16 is formed in a ring shape. If a plurality of permanent magnets 16 are provided, the plurality of permanent magnets 16 are arranged at regular angular intervals along the same circle. As with permanent magnet 16, a single permanent magnet 15 or a plurality of permanent magnets 15 may be provided.

As shown in FIG. 4, a plurality of (e.g., nine) permanent magnets 17 are embedded in shroud 12. The plurality of permanent magnets 17 are arranged with a gap therebetween at regular angular intervals along the same circle such that adjacent magnetic polarities thereof are different from each other. In other words, permanent magnet 17 having the N-pole toward motor chamber 8 and permanent magnet 17 having the S-pole toward motor chamber 8 are alternately arranged with a gap therebetween at regular angular intervals along the same circle.

Figure 7:
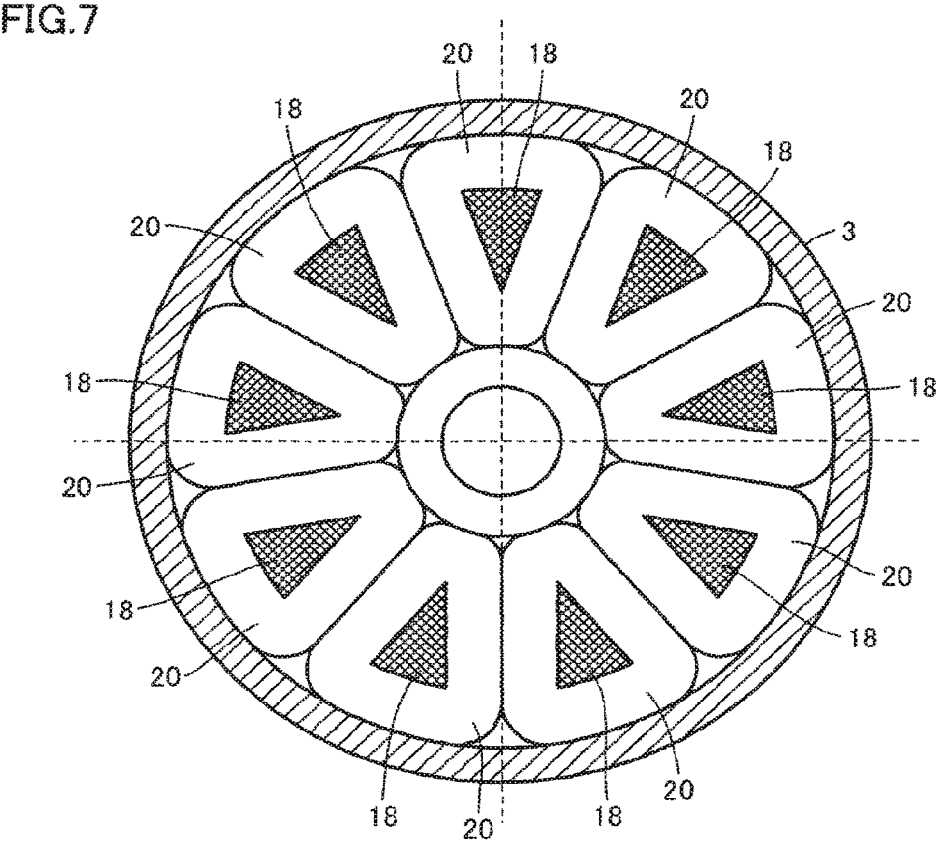
FIG. 7 is a cross-sectional view along the line VII-VII in FIG. 3.
Figure 8:
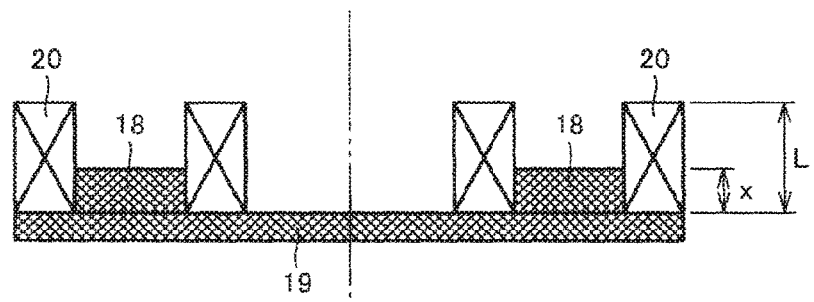
FIG. 8 is a diagram showing a structure of a magnetic element and a coil shown in FIG. 7.

As shown in FIGS. 3 and 7, a plurality of (e.g., nine) magnetic elements 18 are provided in motor chamber 8. The plurality of magnetic elements 18 are arranged at regular angular intervals along the same circle to face the plurality of permanent magnets 17 in impeller 10. A base end of each of the plurality of magnetic elements 18 is joined to one disc-shaped magnetic element 19. A coil 20 is wound around each magnetic element 18. In the direction of a central axis of impeller 10, the length of magnetic element 18 is shorter than that of coil 20. That is, as shown in FIG. 8, when an axial length of magnetic element 18 is expressed as x and an axial length of coil 20 is expressed as L relative to the surface of disc-shaped magnetic element 19, relation of $0<x<L$ is satisfied.

Figure 9:
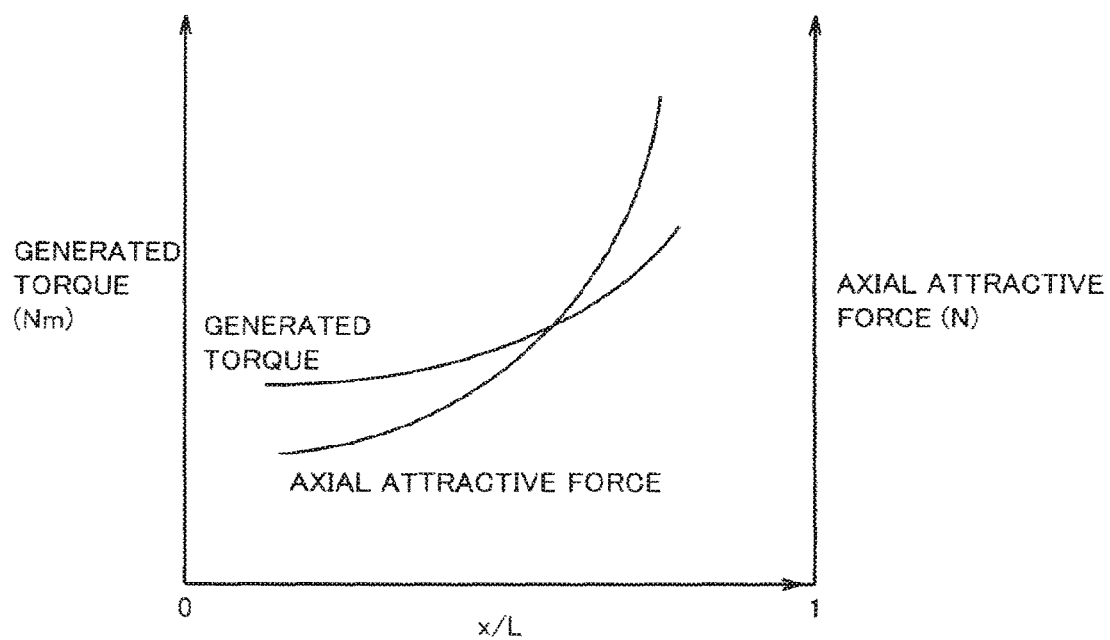
FIG. 9 is a diagram showing relation between x/L shown in FIG. 8, and generated torque and axial attractive force.

A horizontal axis of FIG. 9 represents a ratio x/L of the height x of magnetic element 18 to the height L of coil 20, a left vertical axis represents generated torque (Nm), and a right vertical axis represents axial attractive force (N). As can be seen in FIG. 9, as x/L is increased from 0 to 1, both of the generated torque and axial attractive force increase exponentially. A rate of increase in generated torque is smaller than a rate of increase in axial attractive force. FIG. 9 shows that, when the value of x/L is within a certain range, an amount of variation in axial attractive force is greater than an amount of variation in generated torque. That is, it is important in the centrifugal blood pump apparatus to lower the axial attractive force while satisfying required torque, and the conditions for that can be satisfied by setting and L to their optimal values. As a result, efficiency enhancement and stable rotation of the impeller can both be attained in the centrifugal blood pump apparatus.

Referring back to FIG. 7, space for winding coil 20 is equally secured around the plurality of magnetic elements 18, and surfaces facing each other of every two adjacent magnetic elements 18 are provided substantially in parallel to each other. Thus, a large space for coils 20 can be secured and turns of coils 20 can be increased. As a result, large torque for driving impeller 10 to rotate can be generated. Further, copper loss that occurs in coils 20 can be reduced, thereby enhancing energy efficiency when impeller 10 is driven to rotate. The plurality of magnetic elements 18 may be formed in a cylindrical shape. In this case, a circumferential length of coils 20 can be minimized to reduce copper loss that occurs in coils 20, thereby enhancing energy efficiency when impeller 10 is driven to rotate.

An outline surface surrounding the plurality of magnetic elements 18 (a circle surrounding the peripheries of the plurality of magnetic elements 18 in FIG. 7) may correspond to an outline surface surrounding the plurality of permanent magnets 17 (a circle surrounding the peripheries of the plurality of magnetic elements 18 in FIG. 4), or the outline surface surrounding the plurality of magnetic elements 18 may be larger than the outline surface surrounding the plurality of permanent magnets 17. Further, it is preferable that magnetic element 18 be designed not to be magnetically saturated at maximum rating of pump 1 (a condition where torque for driving impeller 10 to rotate becomes maximum).

Figure 10:
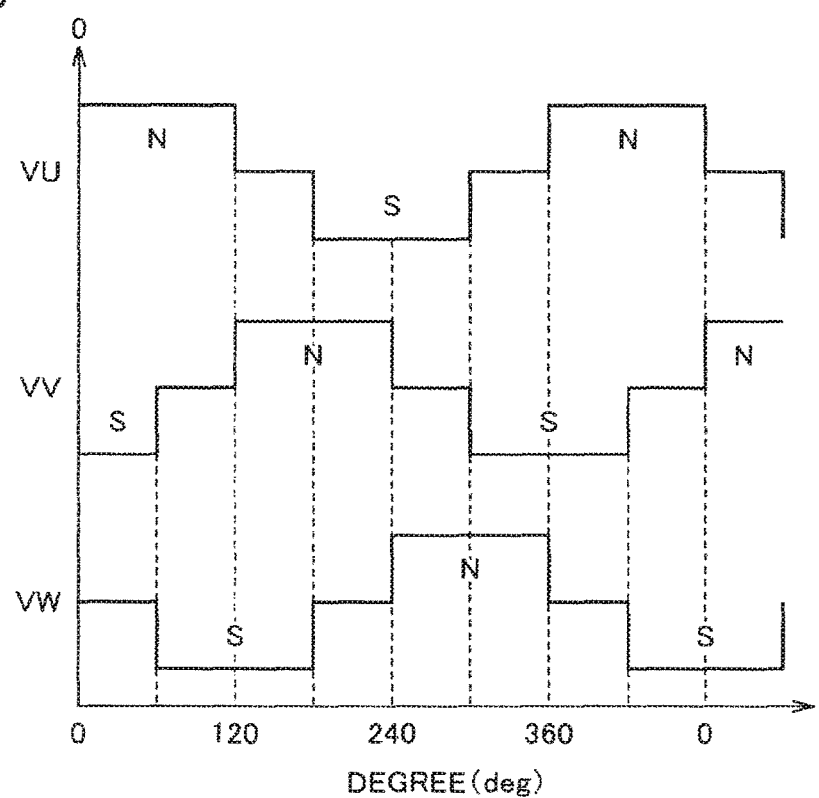
FIG. 10 is a time chart illustrating voltages applied to the plurality of coils shown in FIG. 7.

Voltages are applied to nine coils 20 in a power distribution system shifted by 120 degrees, for example. That is, nine coils 20 are divided into groups each including three coils. Voltages VU, VV, VW as shown in FIG. 10 are applied to first to third coils 20 of each group, respectively. To first coil 20, a positive voltage is applied during a period of 0 to 120 degrees, 0 V is applied during a period of 120 to 180 degrees, a negative voltage is applied during a period of 180 to 300 degrees, and 0 V is applied during a period of 300 to 360 degrees. Accordingly, a tip surface of magnetic element 18 having first coil 20 wound therearound (end surface on the impeller 10 side) becomes the N-pole during the period of 0 to 120 degrees, and becomes the S-pole during the period of 180 to 300 degrees. Voltage VV is delayed in phase from voltage VU by 120 degrees, and voltage VW is delayed in phase from voltage VV by 120 degrees. Thus, rotating magnetic field can be formed by applying voltages VU, VV, VW to first to third coils 20, respectively, so that impeller 10 can be rotated by attractive force and repulsion force between the plurality of magnetic elements 18 and the plurality of permanent magnets 17 in impeller 10.

When impeller 10 is rotating at a rated rotation speed, attractive force between permanent magnets 15 and 16 and attractive force between the plurality of permanent magnets 17 and the plurality of magnetic elements 18 are set to be balanced with each other substantially around a center of a movable range of impeller 10 in blood chamber 7. Thus, force acting on impeller 10 due to the attractive force is very small throughout the movable range of impeller 10. Consequently, frictional resistance during relative slide between impeller 10 and housing 2 which occurs when impeller 10 is activated to rotate can be reduced. In addition, a surface of impeller 10 and a surface of an inner wall of housing 2 are not damaged (no projections and recesses in the surfaces) during the relative slide, and moreover, impeller 10 is readily levitated from housing 2 without contacting even when hydrodynamic force is small during low-speed rotation. Accordingly, occurrence of hemolysis/thrombus due to the relative slide between impeller 10 and housing 2, or occurrence of thrombus due to small damage (projections and recesses) to the surfaces which occurs during the relative slide is avoided.

A plurality of grooves for hydrodynamic bearing 21 are formed in a surface of dividing wall 6 facing shroud 12 of impeller 10, and a plurality of grooves for hydrodynamic bearing 22 are formed in the inner wall of blood chamber 7 facing shroud 11. When a rotation speed of impeller 10 becomes higher than a prescribed rotation speed, a hydrodynamic bearing effect is produced between each of grooves for hydrodynamic bearing 21, 22 and impeller 10. As a result, drag is generated on impeller 10 from each of grooves for hydrodynamic bearing 21, 22, causing impeller 10 to rotate without contacting in blood chamber 7.

Figure 5:
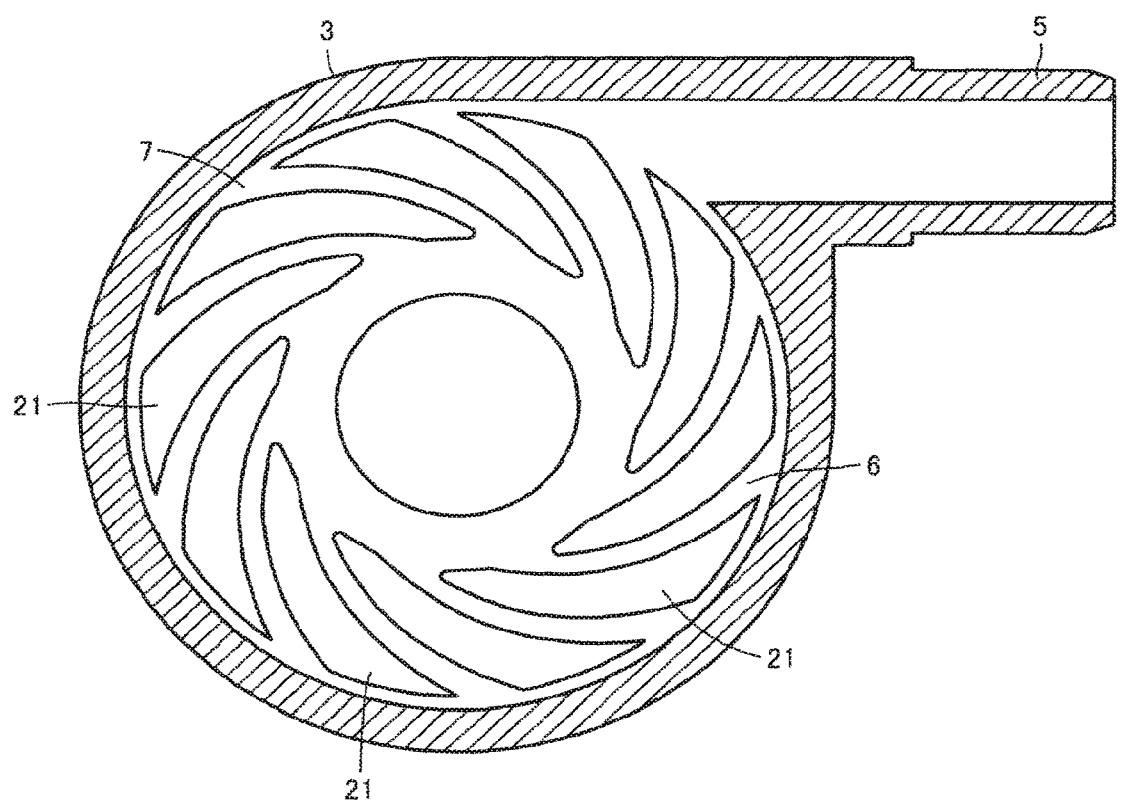
FIG. 5 is a cross-sectional view showing a state where an impeller has been removed from the cross-sectional view along the line IV-IV in FIG. 3.

Specifically, as shown in FIG. 5, the plurality of grooves for hydrodynamic bearing 21 are each formed with a size corresponding to shroud 12 of impeller 10. Each groove for hydrodynamic bearing 21 has one end on an edge (circumference) of a circular portion slightly distant from a center of dividing wall 6, and extends spirally (in other words, in a curved manner) toward a portion near an outer edge of dividing wall 6 such that groove for hydrodynamic bearing 21 gradually increases in width. The plurality of grooves for hydrodynamic bearing 21 have substantially the same shape, and they are arranged at substantially regular intervals. Groove for hydrodynamic bearing 21 is a concave portion, and it preferably has a depth of about 0.005 to 0.4 mm. It is preferable that about 6 to 36 grooves for hydrodynamic bearing 21 be provided.

In FIG. 5, ten grooves for hydrodynamic bearing 21 are equiangularly arranged with respect to the central axis of impeller 10. Since grooves for hydrodynamic hearing 21 have a so-called inward spiral groove shape, clockwise rotation of impeller 10 causes increase in fluid pressure from an outer diameter portion toward an inner diameter portion of grooves for hydrodynamic bearing 21. As a result, repulsion force is generated between impeller 10 and dividing wall 6 and it acts as hydrodynamic force.

Instead of providing grooves for hydrodynamic bearing 21 in dividing wall 6, grooves for hydrodynamic hearing 21 may be provided in a surface of shroud 12 of impeller 10.

In this manner, owing to the hydrodynamic bearing effect produced between impeller 10 and the plurality of grooves for hydrodynamic bearing 21, impeller 10 moves away from dividing wall 6 and rotates without contacting. Accordingly, a blood flow path is secured between impeller 10 and dividing wall 6, thus preventing occurrence of blood accumulation therebetween and the resultant thrombus. Further, in a normal state, grooves for hydrodynamic bearing 21 perform a stirring function between impeller 10 and dividing wall 6, thus preventing occurrence of partial blood accumulation therebetween.

It is preferable that a corner portion of each of grooves for hydrodynamic bearing 21 be rounded to have R of at least 0.05 mm. As a result, occurrence of hemolysis can further be reduced.

Figure 6:
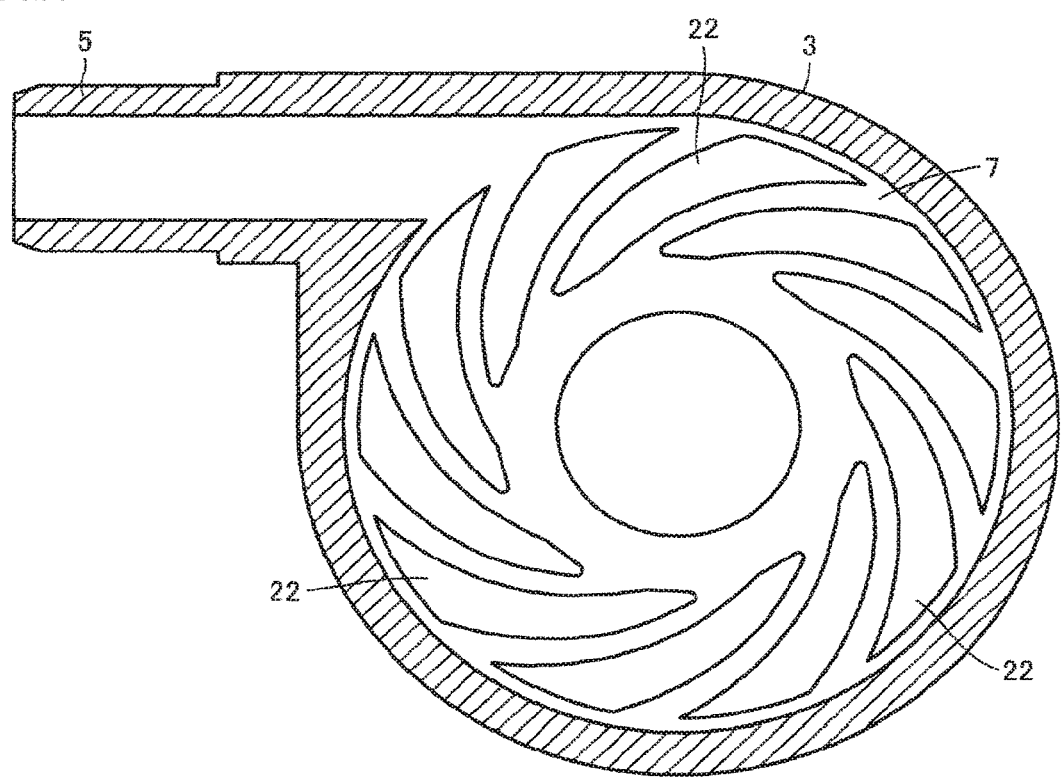
FIG. 6 is a cross-sectional view showing the state where the impeller has been removed from a cross-sectional view along the line VI-VI in FIG. 3.

As with the plurality of grooves for hydrodynamic bearing 21, as shown in FIG. 6, the plurality of grooves for hydrodynamic bearing 22 are each formed with a size corresponding to shroud 11 of impeller 10. Each groove for hydrodynamic bearing 22 has one end on an edge (circumference) of a circular portion slightly distant from a center of the inner wall of blood chamber 7, and extends spirally (in other words, in a curved manner) toward a portion near an outer edge of the inner wall of blood chamber 7 such that groove for hydrodynamic bearing 22 gradually increases in width. The plurality of grooves for hydrodynamic bearing 22 have substantially the same shape, and they are arranged at substantially regular intervals. Groove for hydrodynamic bearing 22 is a concave portion, and it preferably has a depth of about 0.005 to 0.4 mm. It is preferable that about 6 to 36 grooves for hydrodynamic bearing 22 be provided. In FIG. 6, ten grooves for hydrodynamic bearing 22 are equiangularly arranged with respect to the central axis of impeller 10.

Instead of providing grooves for hydrodynamic bearing 22 in the inner wall of blood chamber 7, grooves for hydrodynamic bearing 22 may be provided in a surface of shroud 11 of impeller 10. It is preferable that a corner portion of each of grooves for hydrodynamic bearing 22 be rounded to have R of at least 0.05 mm. As a result, occurrence of hemolysis can further be reduced.

In this manner, owing to the hydrodynamic bearing effect produced between impeller 10 and the plurality of grooves for hydrodynamic bearing 22, impeller 10 moves away from the inner wall of blood chamber 7 and rotates without contacting. In addition, when pump unit 1 is subjected to external impact or when the hydrodynamic force generated by grooves for hydrodynamic bearing 21 becomes excessive, impeller 10 can be prevented from being in close contact with the inner wall of blood chamber 7. The hydrodynamic force generated by grooves for hydrodynamic bearing 21 may be different from the hydrodynamic force generated by grooves for hydrodynamic bearing 22.

It is preferable that impeller 10 rotate in a state where a gap between shroud 12 of impeller 10 and dividing wall 6 is substantially equal to a gap between shroud 11 of impeller 10 and the inner wall of blood chamber 7. If one of the gaps becomes narrower due to serious disturbance such as fluid force acting on impeller 10, it is preferable that grooves for hydrodynamic bearing 21 and 22 have different shapes so that the hydrodynamic force generated by the grooves for hydrodynamic bearing on the narrower side becomes higher than the hydrodynamic force generated by the other grooves for hydrodynamic bearing to make the gaps substantially equal to each other.

While each of grooves for hydrodynamic bearing 21, 22 has the inward spiral groove shape in FIGS. 5 and 6, grooves for hydrodynamic bearing 21, 22 having another shape may be used. Nevertheless, for blood circulation, it is preferable to employ grooves for hydrodynamic bearing 21, 22 having the inward spiral groove shape that allows a smooth flow of blood.

Figure 11:
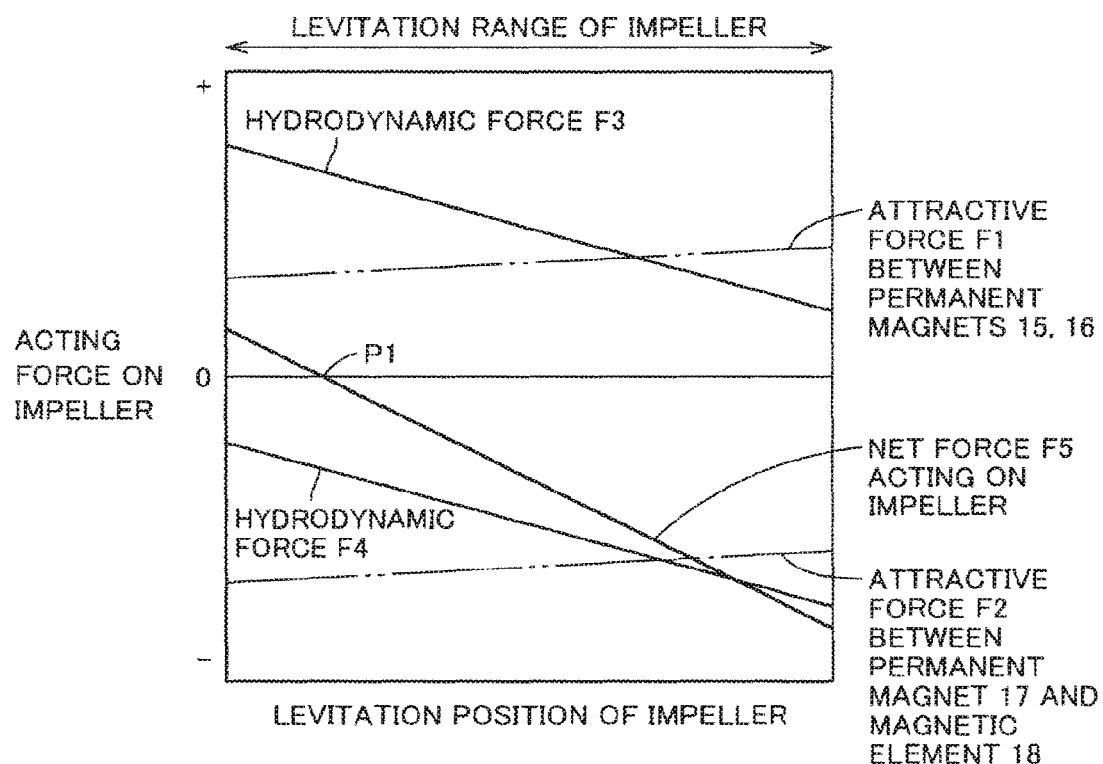
FIG. 11 is a diagram for explaining a levitation position of the impeller shown in FIG. 3.

FIG. 11 is a diagram illustrating forces acting on impeller 10 when magnitude of a resultant force of an attractive force F1 between permanent magnets 15 and 16 and an attractive force F2 between permanent magnet 17 and magnetic element 18 is adjusted to zero at a position P1 other than a central position of the movable range of impeller 10 in blood chamber 7. The rotation speed of impeller 10 is kept at a rated value.

That is, it is assumed that attractive force F1 between permanent magnets 15 and 16 is set to be smaller than attractive force F2 between permanent magnet 17 and magnetic element 18, and a levitation position of impeller 10 where their resultant force becomes zero is on the dividing wall 6 side relative to the center of the movable range of the impeller. Grooves for hydrodynamic bearing 21, 22 have the same shape.

A horizontal axis of FIG. 11 represents a position of impeller 10 (the left side in the figure being the dividing wall 6 side), and a vertical axis represents forces acting on impeller 10. Force acting on impeller 10 toward the dividing wall 6 side is expressed as a negative acting force. As the forces acting on impeller 10, attractive force F1 between permanent magnets 15 and 16, attractive force F2 between permanent magnet 17 and magnetic element 18, a hydrodynamic force F3 generated by grooves for hydrodynamic bearing 21, a hydrodynamic force F4 generated by grooves for hydrodynamic bearing 22, and a "net force F5 acting on impeller" which is their resultant force are illustrated.

As can be seen in FIG. 11, at a position where net force F5 acting on impeller 10 becomes zero, the levitation position of impeller 10 is significantly deviated from the central position of the movable range of impeller 10. As a result, a distance between rotating impeller 10 and dividing wall 6 becomes narrower, and impeller 10 is brought into contact with dividing wall 6 even by the action of a small disturbance force on impeller 10.

Figure 12:
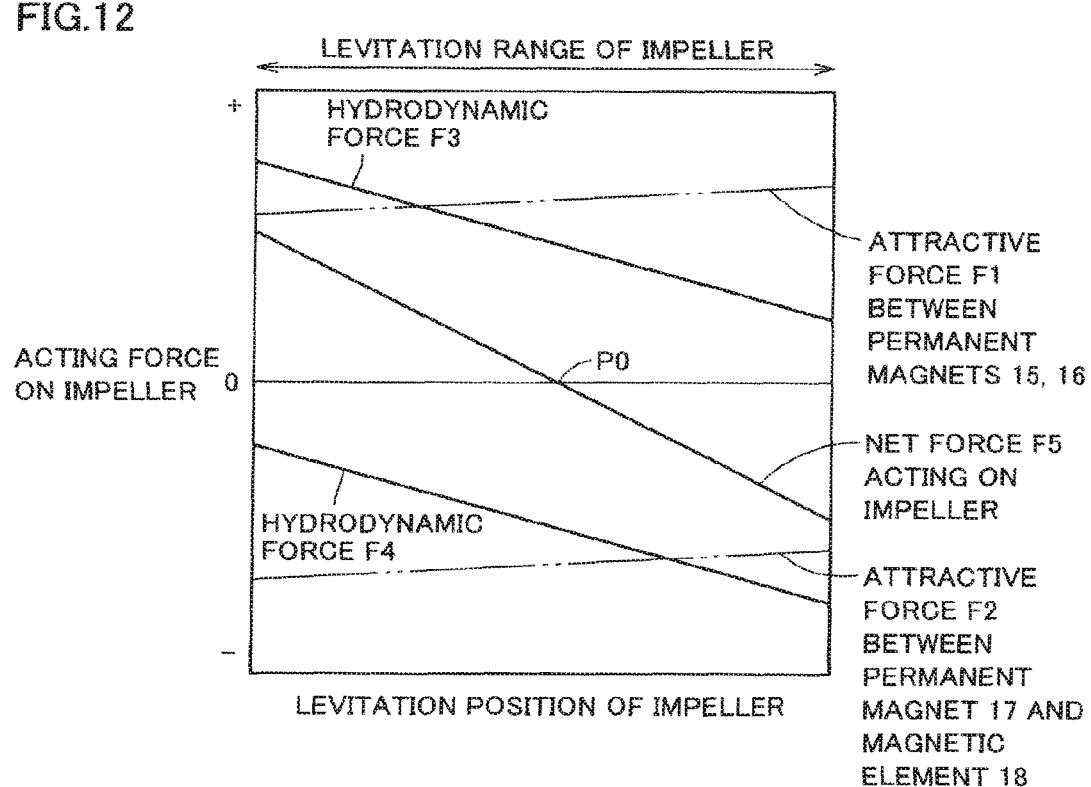
FIG. 12 is another diagram for explaining a levitation position of the impeller shown in FIG. 3.

In contrast, FIG. 12 illustrates forces acting on impeller 10 when a magnitude of the resultant force of attractive force F1 between permanent magnets 15 and 16 and attractive force F2 between permanent magnet 17 and magnetic element 18 is adjusted to zero at a central position P0 of the movable range of impeller 10 in blood chamber 7. The rotation speed of impeller 10 is kept at the rated value in this case as well.

Namely, attractive force F1 between permanent magnets 15 and 16 and attractive force F2 between permanent magnet 17 and magnetic element 18 are set to be substantially equal to each other. In addition, grooves for hydrodynamic bearing 21, 22 have the same shape. In this case, supporting rigidity for the levitation position of impeller 10 is higher than in the example shown in FIG. 11. Further, since net force F5 acting on impeller 10 is zero at the center of the movable range, impeller 10 is levitated at the central position when a disturbance force is not acting on impeller 10.

As such, a levitation position of impeller 10 is determined by balance among attractive force F1 between permanent magnets 15 and 16, attractive force F2 between permanent magnet 17 and magnetic element 18, and hydrodynamic forces F3, F4 generated by grooves for hydrodynamic bearing 21, 22 during rotation of impeller 10. By making F1 and F2 substantially equal to each other and by forming grooves for hydrodynamic bearing 21, 22 in the same shape, impeller 10 can be levitated substantially in a central portion of blood chamber 7 during rotation of impeller 10. Since impeller 10 has such a shape that vanes are formed between two discs as shown in FIGS. 3 and 4, two surfaces facing the inner wall of housing 2 can be formed to have the same shape and the same dimensions. Therefore, it is possible to provide grooves for hydrodynamic bearing 21, 22 having a function to generate substantially the same hydrodynamic force on both sides of impeller 10.

In this case, impeller 10 is levitated at the central position of blood chamber 7, and thus held at a position farthest from the inner wall of housing 2. As a result, even if the levitation position of impeller 10 is changed due to application of a disturbance force to levitated impeller 10, the possibility that impeller 10 is brought into contact with the inner wall of housing 2 is lowered, thus also lowering the possibility of occurrence of thrombus and hemolysis resulting from such contact.

While two grooves for hydrodynamic bearing 21, 22 have the same shape in the examples shown in FIGS. 11 and 12, grooves for hydrodynamic bearing 21, 22 may be different from each other in shape and hydrodynamic force generating function. For example, when disturbance acts on impeller 10 always in one direction due to fluid force or the like during pumping, performance of a groove for hydrodynamic bearing in the disturbance direction may be made higher than performance of the other groove for hydrodynamic bearing, thereby levitating and rotating impeller 10 at the central position of housing 2. As a result, the probability of contact between impeller 10 and housing 2 can be lowered, thereby attaining stable levitation performance of impeller 10.

Furthermore, when an absolute value of a negative axial supporting rigidity value of impeller 10 which is constituted of attractive force F1 between permanent magnets 15 and 16 and attractive force F2 between permanent magnet 17 and magnetic element 18 is expressed as Ka, an absolute value of a positive radial rigidity value is expressed as Kr, and an absolute value of a positive rigidity value obtained by two grooves for hydrodynamic bearing 21, 22 in a normal rotation speed range where impeller 10 rotates is expressed as Kg, it is preferable that relation of Kg>Ka+Kr be satisfied.

Specifically, when absolute value Ka of the negative axial rigidity value is 20000 N/m and absolute value Kr of the positive radial rigidity value is 10000 N/m, absolute value Kg of the positive rigidity value obtained by two grooves for hydrodynamic bearing 21, 22 in the rotation speed range where impeller 10 normally rotates is set to a value higher than 30000 N/m.

The axial supporting rigidity for impeller 10 is a value obtained by subtracting negative rigidity due to the attractive force between the magnetic elements and the like from rigidity resulting from the hydrodynamic force generated by grooves for hydrodynamic bearing 21, 22. Thus, by satisfying the relation of Kg>Ka+Kr, the axial supporting rigidity for impeller 10 can be made higher than the radial supporting rigidity. With such setting, movement of impeller 10 can be suppressed more in the axial direction than in the radial direction when a disturbance force acts on impeller 10, thereby avoiding mechanical contact between impeller 10 and housing 2 in a portion where grooves for hydrodynamic bearing 21 are formed.

In particular, since grooves for hydrodynamic bearing 21, 22 are provided as concave portions in planar surfaces as shown in FIGS. 5 and 6, mechanical contact between housing 2 and impeller 10 in these portions during rotation of impeller 10 may result in damage to one or both of a surface of impeller 10 and a surface of the inner wall of housing 2 (projections and recesses in the surfaces), and blood passage through this portion may cause occurrence of thrombus and hemolysis. In order to prevent mechanical contact at grooves for hydrodynamic bearing 21, 22 to suppress thrombus and hemolysis, it is effective to make the axial rigidity higher than the radial rigidity.

Whirl occurs in unbalanced impeller 10 during rotation, and this whirl is greatest when a natural frequency determined by the mass of impeller 10 and the supporting rigidity value of impeller 10 matches the rotation speed of impeller 10.

Since the radial supporting rigidity for impeller 10 is smaller than the axial supporting rigidity in pump unit 1, it is preferable to set a maximum rotation speed of impeller 10 to be equal to or lower than the radial natural frequency. Accordingly, in order to prevent mechanical contact between impeller 10 and housing 2, when a radial rigidity value of impeller 10 which is constituted of attractive force F1 between permanent magnets 15 and 16 and attractive force F2 between permanent magnet 17 and magnetic element 18 is expressed as Kr (N/m), the mass of impeller 10 is expressed as m (kg), and the rotation speed of the impeller is expressed as ω (rad/s), it is preferable that relation of $\omega < (Kr/m)^{0.5}$ be satisfied.

Specifically, when the mass of impeller 10 is 0.03 kg and the radial rigidity value is 2000 N/m, the maximum rotation speed of impeller 10 is set to 258 rad/s (2465 rpm) or lower. Conversely, when the maximum rotation speed of impeller 10 is set to 366 rad/s (3500 rpm), the radial rigidity is set to 4018 N/m or higher.

It is further preferable to set the maximum rotation speed of impeller 10 to 80% or lower of this ω. Specifically, when the mass of impeller 10 is 0.03 kg and the radial rigidity value is 2000 N/m, the maximum rotation speed is set to 206.4 rad/s (1971 rpm) or lower. Conversely, when it is desired to set the maximum rotation speed of impeller 10 to 366 rad/s (3500 rpm), the radial rigidity value is set to 6279 N/m or higher. By thus setting the maximum rotation speed of impeller 10, contact between rotating impeller 10 and housing 2 can be suppressed.

When the rigidity due to the hydrodynamic force generated by grooves for hydrodynamic bearing 21, 22 becomes higher than the negative axial rigidity value of impeller 10 which is constituted of attractive force F1 between permanent magnets 15 and 16 and attractive force F2 between permanent magnet 17 and magnetic element 18, impeller 10 and housing 2 are not in contact with each other. It is thus preferable to minimize this negative rigidity value. In order to minimize the negative rigidity value, it is preferable that surfaces facing each other of permanent magnets 15, 16 have different sizes. For example, by making the size of permanent magnet 16 smaller than that of permanent magnet 15, a rate of variation in attractive force that varies with a distance between the magnets, that is, the negative rigidity, can be minimized, thereby preventing lowering in supporting rigidity for the impeller.

It is also preferable to check to see that impeller 10 is in contact with dividing wall 6 before activating impeller 10 to rotate.

Namely, when impeller 10 is not rotating, impeller 10 is not supported without contacting by grooves for hydrodynamic bearing 21, 22, but is in contact with housing 2 with a high surface pressure due to attractive force F1 between permanent magnets 15 and 16 and attractive force F2 between permanent magnet 17 and magnetic element 18. Further, when impeller 10 is rotated by magnetic interaction between coil 20 and magnetic element 18 in motor chamber 8 and permanent magnet 17 in impeller 10 as in pump unit 1, starting torque is smaller than in an example where an impeller is driven to rotate through magnetic coupling between permanent magnets as shown in FIG. 3 of PTL 2. It is thus difficult to smoothly activate impeller 10 to rotate.

When shroud 12 of impeller 10 is in contact with dividing wall 6, however, permanent magnet 17 in impeller 10 and magnetic element 18 in motor chamber 8 are closer to each other than when shroud 11 of impeller 10 is in contact with the inner wall of blood chamber 7, which allows increase in rotational torque during activation of impeller 10, thereby smoothly activating impeller 10 to rotate.

As described above, however, when impeller 10 is rotating, attractive force F1 between permanent magnets 15 and 16 and attractive force F2 between permanent magnet 17 and magnetic element 18 are set to be balanced with each other around the center of the movable range of impeller 10. Thus, impeller 10 is not necessarily in contact with dividing wall 6 when impeller 10 is not rotating.

For this reason, this centrifugal blood pump apparatus is provided with means for moving impeller 10 toward dividing wall 6 before activating impeller 10 to rotate. Specifically, a current is fed through the plurality of coils 20 such that attractive force F2 between permanent magnet 17 and magnetic element 18 becomes higher, to move impeller 10 toward dividing wall 6.

Figure 13:
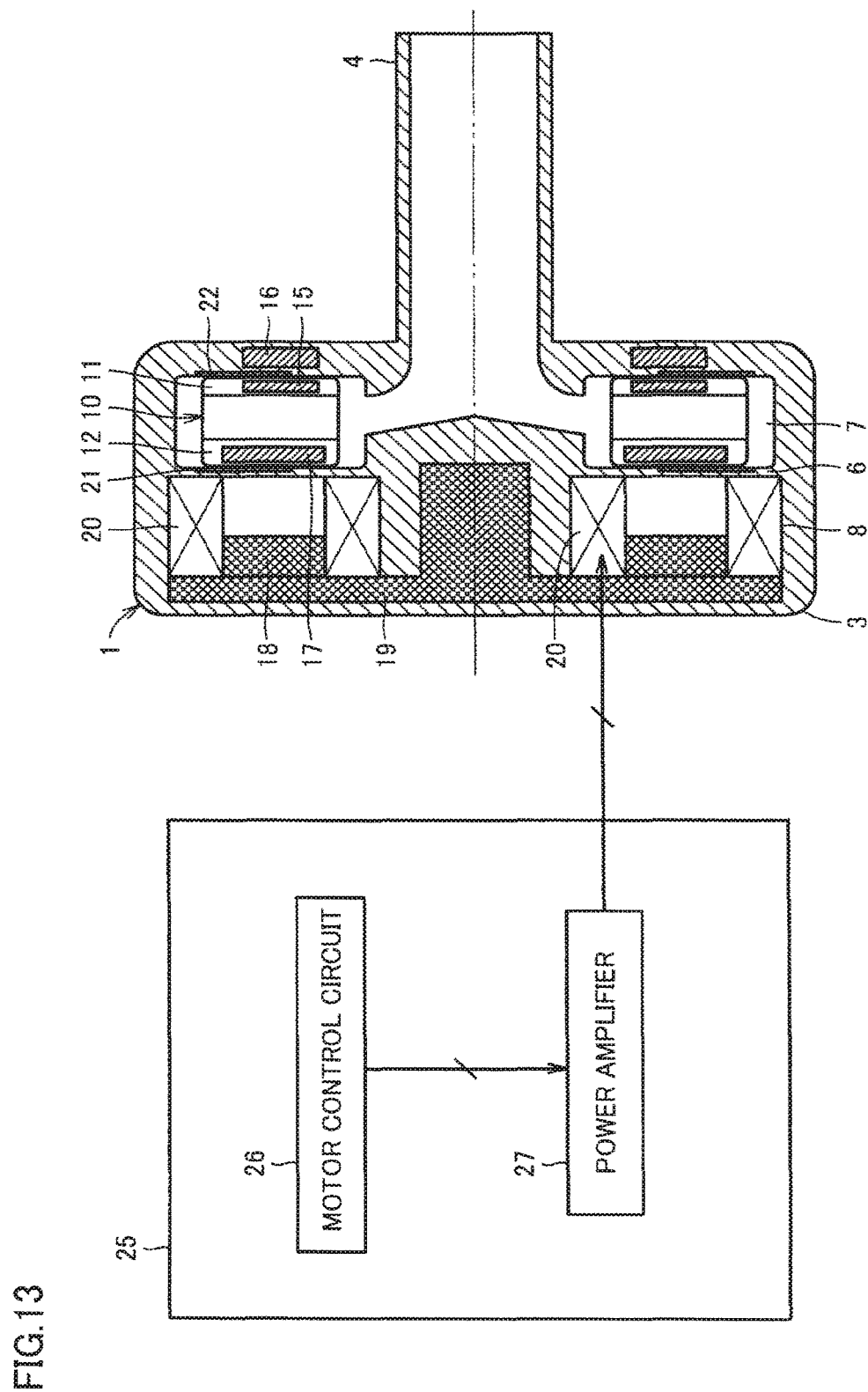
FIG. 13 is a block diagram showing a configuration of a controller for controlling the pump unit shown in FIGS. 1 to 7.

FIG. 13 is a block diagram showing a configuration of a controller 25 for controlling pump unit 1. In FIG. 13, controller 25 includes a motor control circuit 26 and a power amplifier 27. Motor control circuit 26 outputs three-phase control signals in the power distribution system shifted by 120 degrees, for example. Power amplifier 27 amplifies the three-phase control signals from motor control circuit 26, and generates three-phase voltages VU, VV, VW shown in FIG. 10. Three-phase voltages VU, VV, VW are applied to first to third coils 20 described with reference to FIGS. 7 and 10, respectively. As a result, during normal operation, impeller 10 rotates at a prescribed rotation speed at the central position of the movable range.

Figure 14:
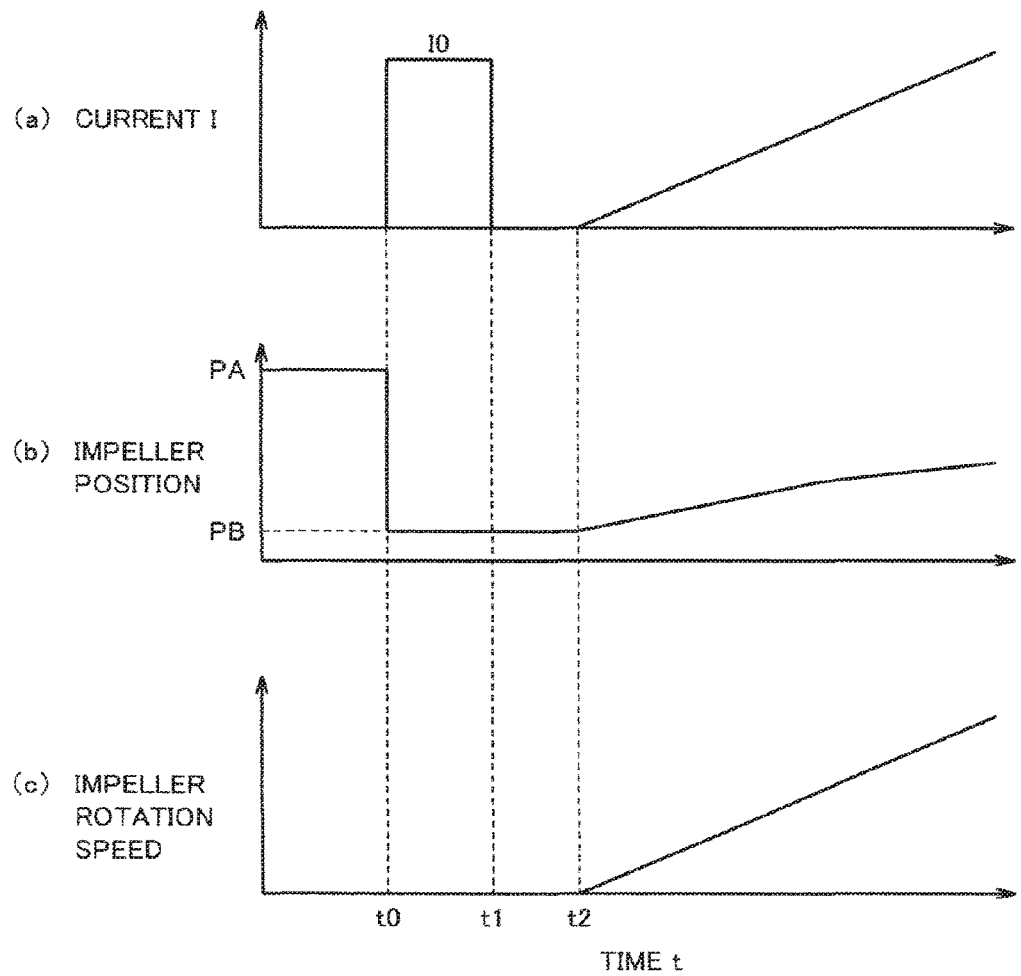
FIG. 14 is a time chart illustrating operation of the controller shown in FIG. 13.

FIGS. 14 (a) to (c) are time charts illustrating temporal variations of a coil current I when impeller 10 is activated to rotate, a position of impeller 10, and a rotation speed of impeller 10. Referring to FIGS. 14 (a) to (c), it is assumed that, in an initial state, shroud 11 of impeller 10 is in contact with the inner wall of blood chamber 7, and impeller 10 is at a position PA. At time t0, a predetermined current I0 is fed through coils 20. As a result, attractive force F2 between permanent magnet 17 and magnetic element 18 becomes higher than attractive force F1 between permanent magnets 15 and 16, so that impeller 10 moves to a position PB on the dividing wall 6 side, causing shroud 12 of impeller 10 to be in contact with dividing wall 6. When impeller 10 moved to position PB, current I0 is cut off (time t1). It is preferable to provide a sensor for detecting a position of impeller 10 in blood chamber 7, and check to see that impeller 10 is in contact with dividing wall 6 before cutting off current I0.

Then, coil current I is gradually increased to a predetermined rated value. Here, impeller 10 is in contact with dividing wall 6, and thus smoothly rotates. With the increase in coil current I, impeller 10 moves from position PB on the dividing wall 6 side to the central position of the movable range.

Since magnetic elements 18 are made shorter than coils 20 in the first embodiment as described above, the axial attractive force can be lowered while required torque is satisfied. Therefore, efficiency enhancement and stable rotation of the impeller can both be attained.

Figure 15:
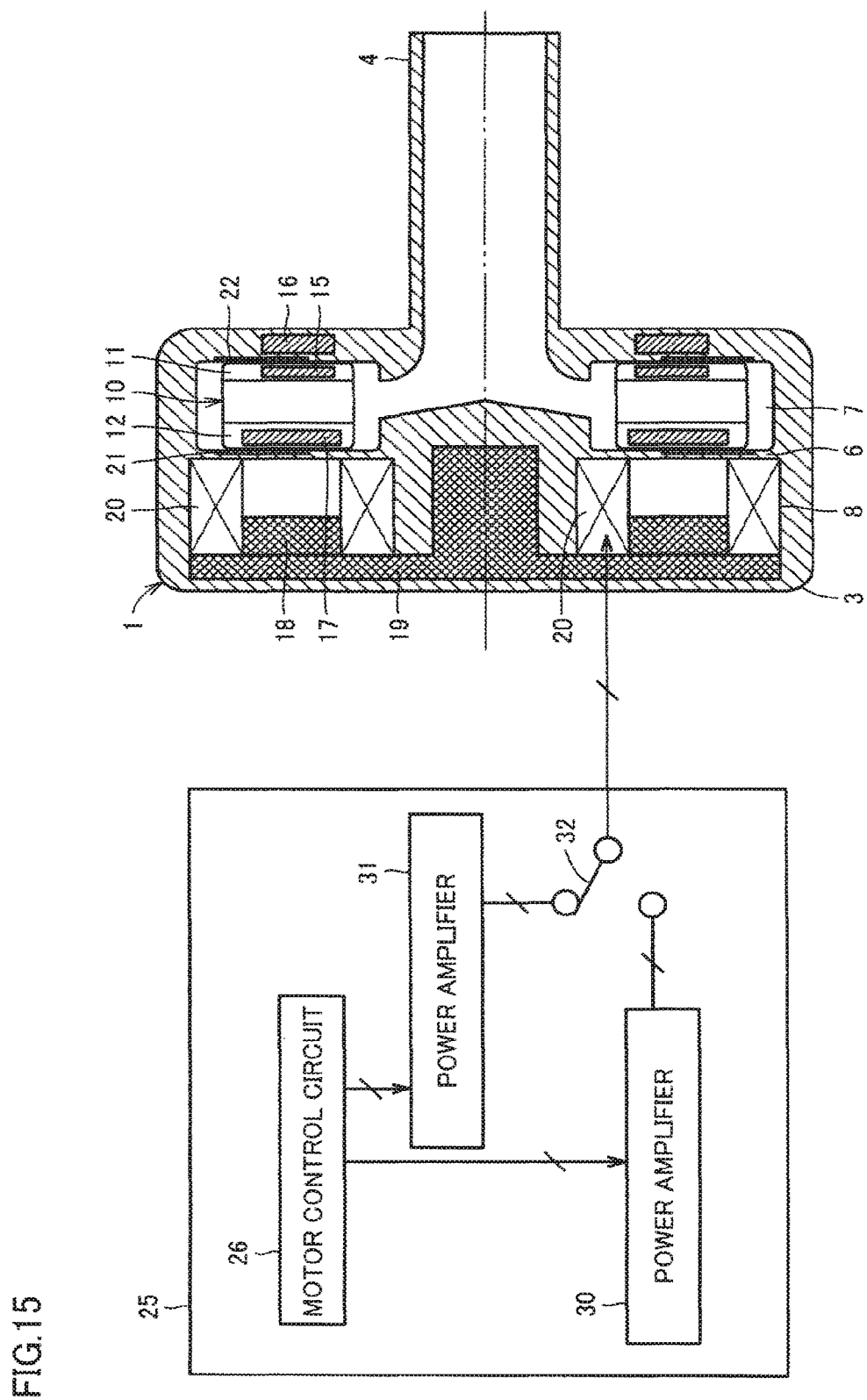
FIG. 15 is a diagram showing a modification of the first embodiment.

Various modifications of the first embodiment will be described below. FIG. 15 is a block diagram showing a modification of the first embodiment. This figure shows an example of a configuration where power source supply is switched between during activation of the impeller for rotation and the remaining period. Referring to FIG. 15, in this modification, power amplifier 27 in FIG. 13 is replaced with power amplifiers 30, 31 and a switch 32. Between times t0 and t1 in FIG. 14, an output signal from motor control circuit 26 is provided to power amplifier 30 and an output voltage from power amplifier 30 is applied to coils 20 via switch 32, causing current I0 to flow through coils 20. After time t2, an output signal from motor control circuit 26 is provided to power amplifier 31 and an output voltage from power amplifier 31 is applied to coils 20 via switch 32, causing a current to flow through coils 20.

Figure 16:
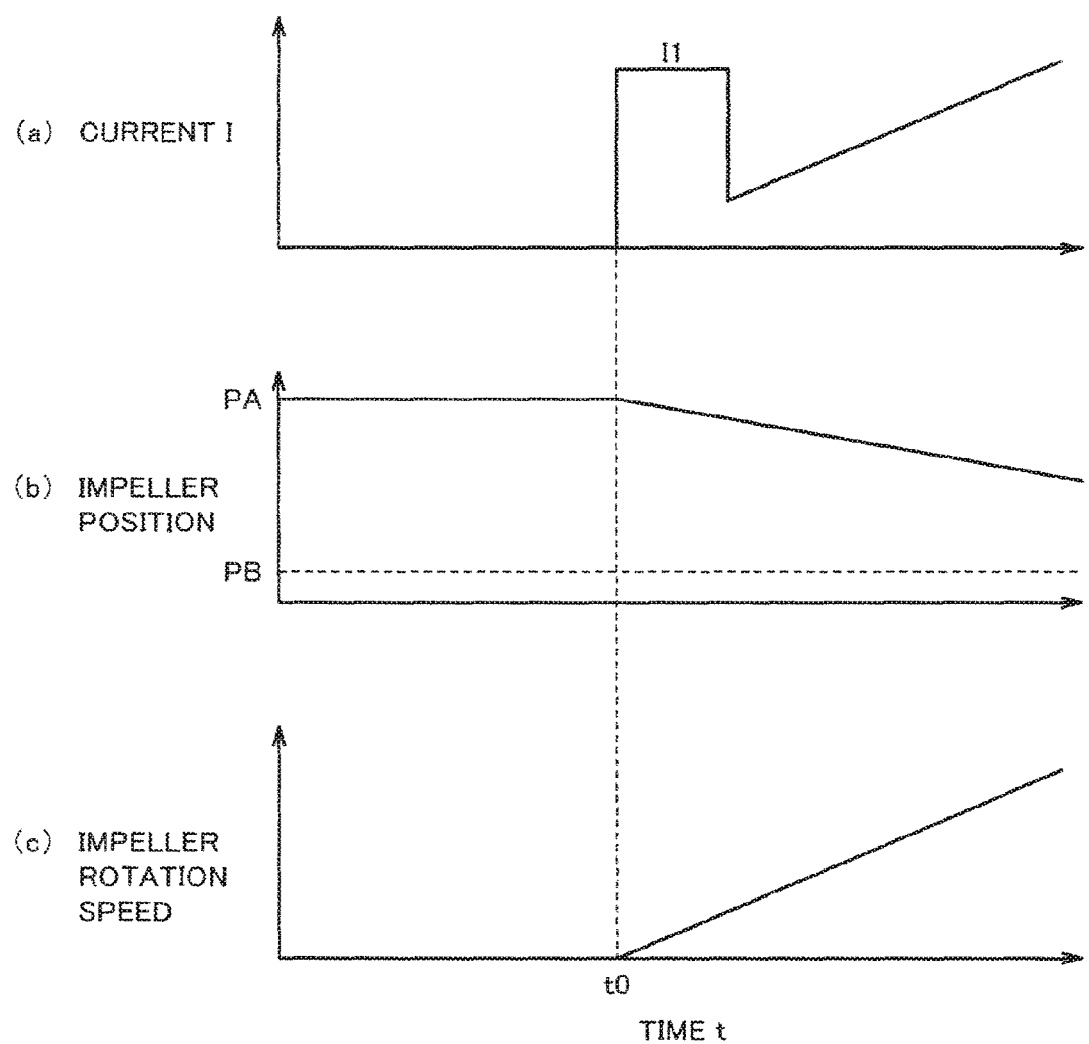
FIG. 16 is a time chart illustrating another modification of the first embodiment.

FIGS. 16 (a) to (c) are time charts illustrating another modification of the first embodiment. Referring to FIGS. 16 (a) to (c), it is assumed that, in an initial state, shroud 11 of impeller 10 is in contact with the inner wall of blood chamber 7, and impeller 10 is at position PA. At time t0, a predetermined current I1 is fed through coils 20. Motor control circuit 26 outputs three-phase control signals in the power distribution system shifted by 120 degrees, for example. Power amplifier 27 amplifies the three-phase control signals from motor control circuit 26 and generates three-phase voltages VU, VV, VW shown in FIG. 10. Three-phase voltages VU, VV, VW are applied to first to third coils 20 described with reference to FIG. 7, respectively. Accordingly, rotating magnetic field is applied to impeller 10 by current I1. Current I1 is larger than current I0 in FIG. 14 and it can activate impeller 10 to rotate even when shroud 11 of impeller 10 is in contact with the inner wall of blood chamber 7. After activation for rotation is confirmed, coil current I is reduced and gradually increased to the predetermined rated value. In this manner, even when impeller 10 is on the position PA side, an overcurrent may be fed through coils 20 only when impeller 10 is activated to rotate.

In addition, a diamond-like carbon (DLC) coating may be formed on at least one of the surface of the inner wall of blood chamber 7 and the surface of dividing wall 6, and the surface of impeller 10. As a result, frictional force between impeller 10, and the inner wall of blood chamber 7 and dividing wall 6 can be lowered to smoothly activate the impeller to rotate. A fluorine-based resin coating, a paraxylylene-based resin coating or the like may be formed instead of the diamond-like carbon coating.

Figure 17:
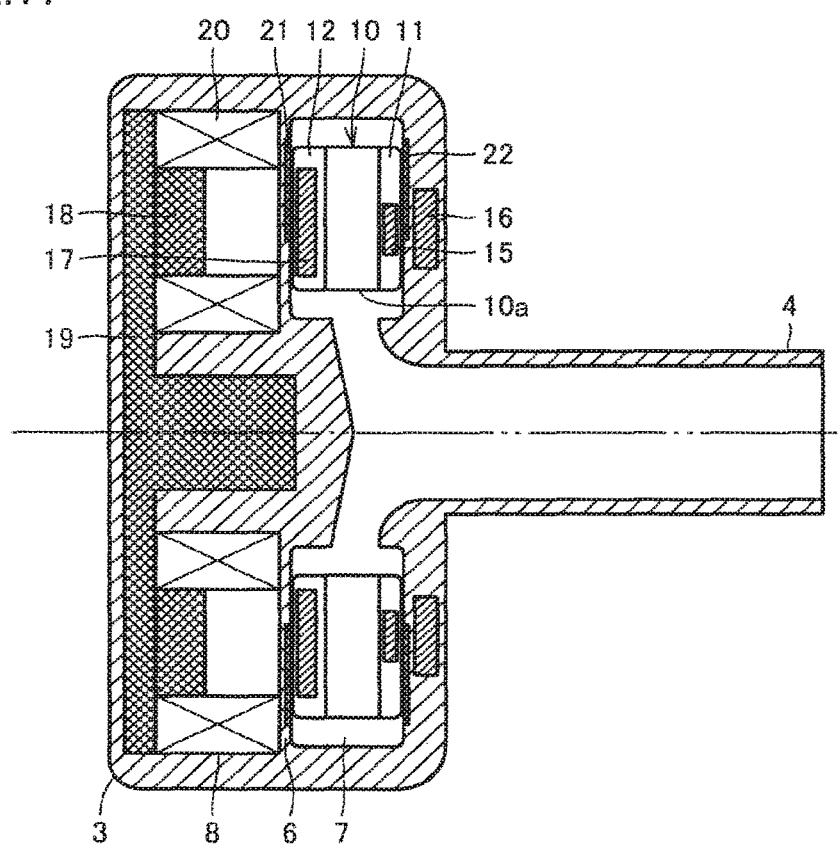
FIG. 17 is a diagram showing yet another modification of the first embodiment.

FIG. 17 is a cross-sectional view showing yet another modification of the first embodiment, which is compared to FIG. 3. Referring to FIG. 17, in this modification, the surfaces facing each other of permanent magnets 15 and 16 have different sizes. While the surfaces facing each other of permanent magnets 15 and 16 have the same size in FIG. 3, by making the surfaces facing each other of permanent magnets 15 and 16 have different sizes, the amount of variation in attractive force which varies with a distance between the magnets, namely, the negative rigidity, can be minimized, thereby preventing lowering in supporting rigidity for impeller 10.

Figure 18:
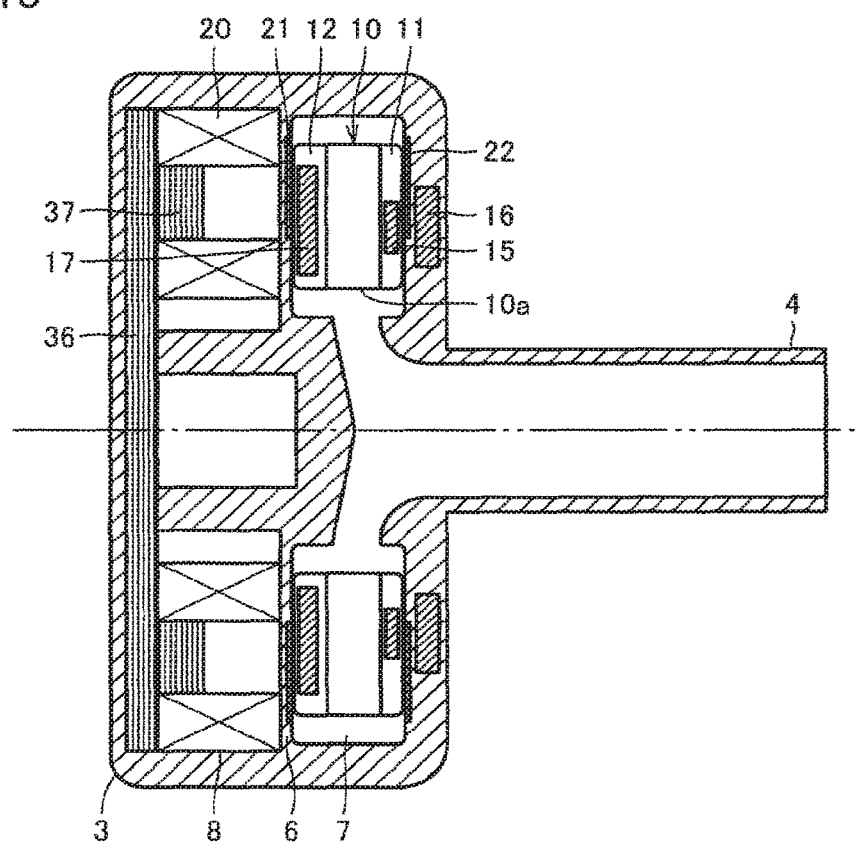
FIG. 18 is a diagram showing yet another modification of the first embodiment.

FIG. 18 is a cross-sectional view showing yet another modification of the first embodiment, which is compared to FIG. 17. Referring to FIG. 18, in this modification, yoke 19 is replaced with a yoke 36, and magnetic element 18 is replaced with a magnetic element 37. Yoke 36 and magnetic element 37 each include a plurality of steel plates stacked in a length direction of a rotation axis of impeller 10. In this modification, eddy current loss that occurs in yoke 36 and magnetic element 37 can be reduced, thereby enhancing energy efficiency when impeller 10 is driven to rotate.

Figure 19:
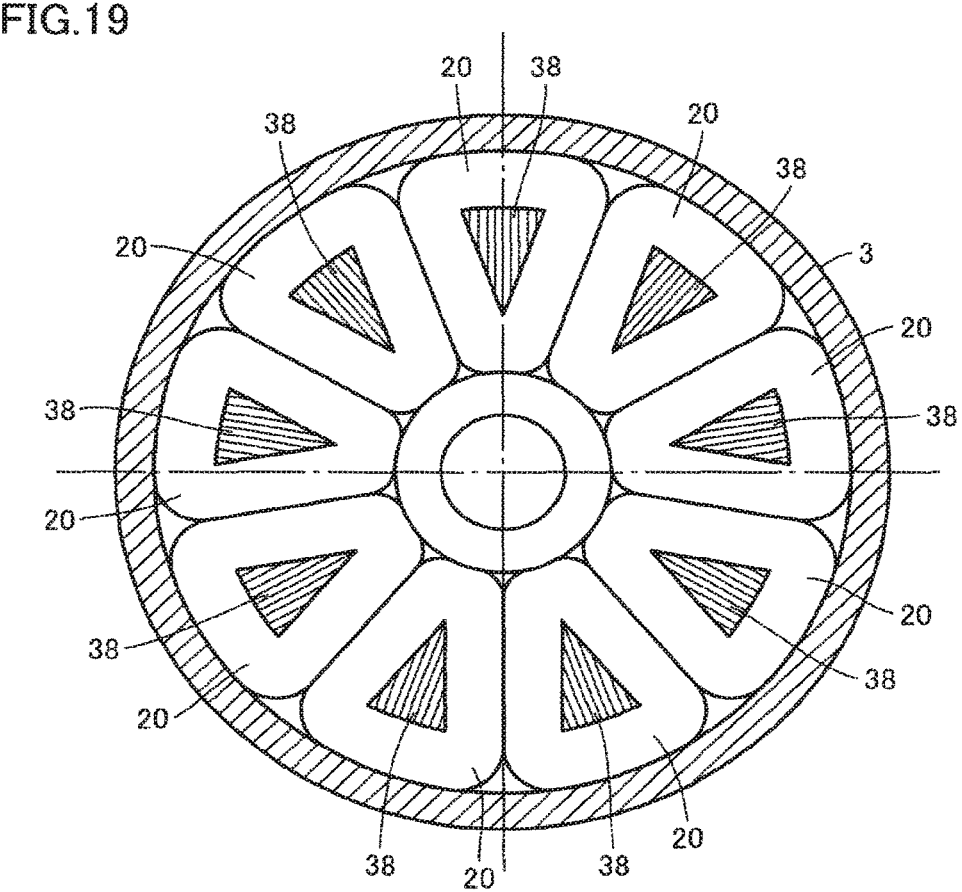
FIG. 19 is a diagram showing yet another modification of the first embodiment.
Figure 20:
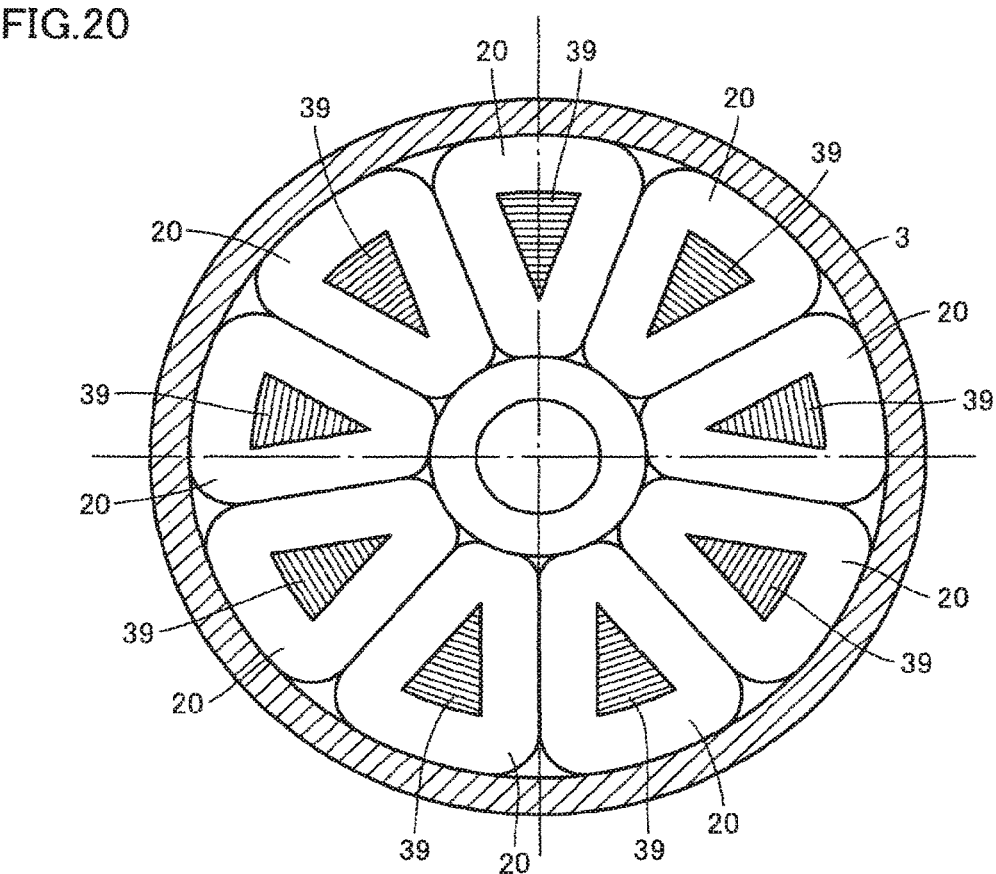
FIG. 20 is a diagram showing yet another modification of the first embodiment.

Alternatively, as shown in FIG. 19, magnetic element 37 may be replaced with a magnetic element 38 including a plurality of steel plates stacked in a rotation direction of impeller 10. Alternatively, as shown in FIG. 20, magnetic element 37 may be replaced with a magnetic element 39 including a plurality of steel plates stacked in a radial direction of impeller 10. The same effect as in the modification in FIG. 18 can be obtained in these cases as well.

Alternatively, each of yoke 19 and magnetic element 18 in FIG. 3 may be made of powders of pure iron, soft iron, or ferrosilicon. In this case, iron loss in yoke 19 and magnetic element 18 can be reduced, thereby enhancing energy efficiency when impeller 10 is driven to rotate.

Figure 21:
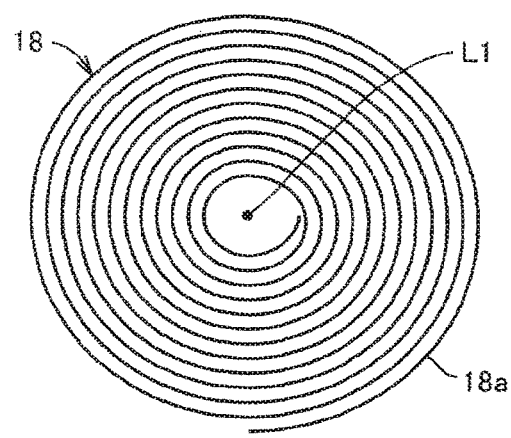
FIG. 21 is a diagram showing yet another modification of the first embodiment.

In a modification shown in FIG. 21, each magnetic element 18 includes a thin strip-shaped magnetic steel plate 18a wound a plurality of times around a center line L1 perpendicular to dividing wall 6. Strip-shaped magnetic steel plate 18a is wound in a length direction, with its width direction toward a direction perpendicular to dividing wall 6. Magnetic steel plate 18a may be an electromagnetic steel plate having a non-directional or directional magnetic property, or may be made of an amorphous metal or an amorphous alloy. Wound magnetic steel plate 18a may be fixed into a prescribed shape by welding a winding end portion of magnetic steel plate 18a to magnetic steel plate 18a itself. Alternatively, wound magnetic steel plate 18a may be fixed into a prescribed shape by immersing the entire magnetic steel plate 18a in resin and curing the resin.

By forming magnetic element 18 using wound, thin strip-shaped magnetic steel plate 18a in this manner, iron loss in magnetic element 18 can be reduced, and magnetic permeability of a magnetic flux in magnetic element 18 can be increased, thereby enhancing energy efficiency when impeller 10 is driven to rotate. Furthermore, magnetic element 18 can be readily formed, thereby attaining size and cost reductions and productivity enhancement of the apparatus.

Magnetic steel plate 18a may be wound in a cylindrical shape, or in a prism shape such as a triangular prism. FIG. 21 shows a state where magnetic steel plate 18a has been wound in a cylindrical shape around center line L1. A circular end surface of magnetic element 18 formed in a cylindrical shape (namely, magnetic steel plate 18a wound in a cylindrical shape) is arranged to face impeller 10 with dividing wall 6 being interposed. Coil 20 is wound to surround the entire outer circumferential surface (side surface) of cylindrical magnetic element 18. When magnetic steel plate 18a is wound in a cylindrical shape, a circumferential length of coil 20 can be minimized to reduce copper loss that occurs in coil 20, thereby enhancing energy efficiency when impeller 10 is driven to rotate.

Alternatively, magnetic steel plate 18a can be wound in a prism shape such as a triangular prism around center line L1. A triangular end surface of magnetic element 18 formed in a triangular prism shape (namely, magnetic steel plate 18a wound in a triangular prism shape) is arranged to face impeller 10 with dividing wall 6 being interposed. Coil 20 is wound to surround the entire side surface of magnetic element 18 in a triangular prism shape. In addition, space for winding coil 20 is equally secured around the plurality of magnetic elements 18, and surfaces facing each other of every two adjacent magnetic elements 18 are provided substantially in parallel to each other. Thus, a large space for coils 20 can be secured and turns of coils 20 can be increased. As a result, large torque for driving impeller 10 to rotate can be generated. Further, copper loss that occurs in coils 20 can be reduced, thereby enhancing energy efficiency when impeller 10 is driven to rotate. It is preferable that magnetic element 18 be designed not to be magnetically saturated at maximum rating of pump 1 (a condition where torque for driving impeller 10 to rotate becomes maximum).

Figure 22:
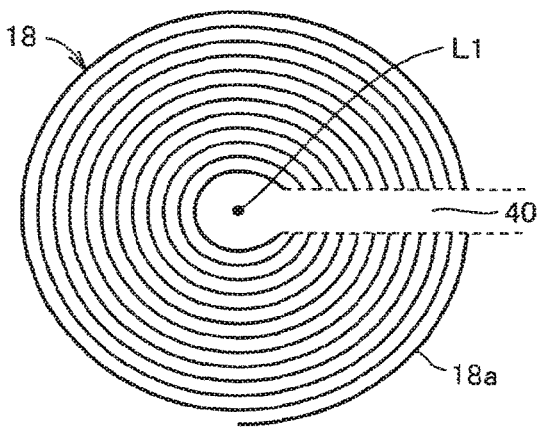
FIG. 22 is a diagram showing yet another modification of the first embodiment.

FIG. 22 is a cross-sectional view showing yet another modification of the first embodiment, which is compared to FIG. 21. Referring to FIG. 22, in this modification, a notch 40 is formed from an inner circumferential surface toward an outer circumferential surface of magnetic element 18. That is, magnetic steel plate 18a is wound a plurality of times around center line L1, and constitutes a plurality of tubular members concentrically arranged. Notch 40 cuts each of the plurality of tubular members in a direction parallel to center line L1 on one side of center line L1 (right side in FIG. 22). In this modification, iron loss in magnetic element 18 can be reduced owing to the provision of notch 40.

Figure 23:
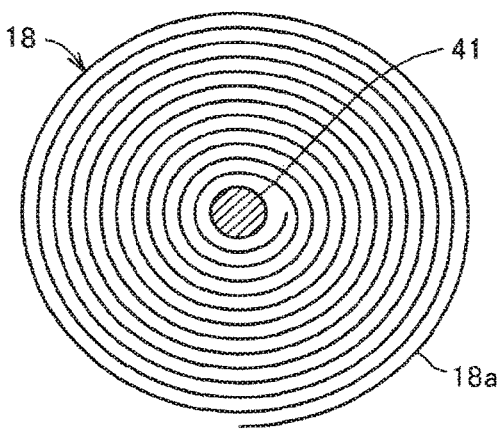
FIG. 23 is a diagram showing yet another modification of the first embodiment.

FIG. 23 is a cross-sectional view showing yet another modification of the first embodiment, which is compared to FIG. 21. Referring to FIG. 23, in this modification, a rod-like magnetic element 41 which is a soft magnetic element is used as a core member in magnetic element 18. Magnetic steel plate 18a is wound a plurality of times around magnetic element 41. Magnetic steel plate 18a may be fixed into a prescribed shape by welding one end of magnetic steel plate 18a to magnetic element 41 and the other end of magnetic steel plate 18a to magnetic steel plate 18a itself. Alternatively, magnetic steel plate 18a may be fixed into a prescribed shape by immersing the entire magnetic element 41 and magnetic steel plate 18a in resin and curing the resin.

Figure 24:
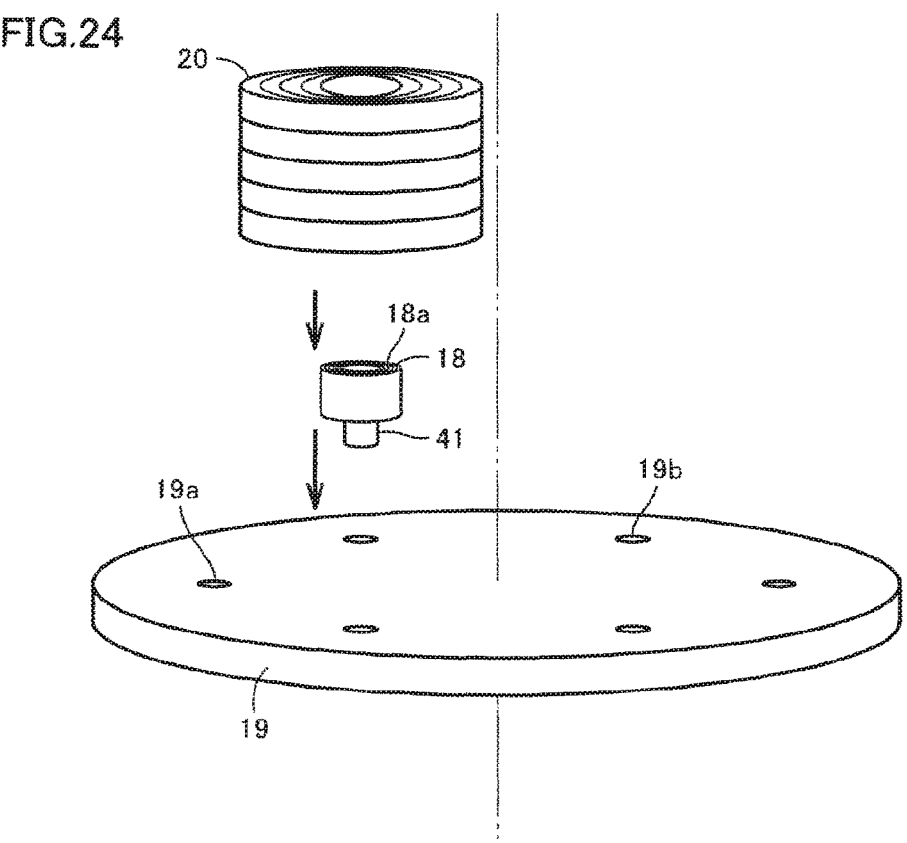
FIG. 24 is a diagram showing yet another modification of the first embodiment.

FIG. 24 is a diagram showing yet another modification of the first embodiment. Referring to FIG. 24, in this modification, each magnetic element 18 includes magnetic element 41 and magnetic steel plate 18a. The length of rod-like magnetic element 41 is longer than the width of magnetic steel plate 18a. Magnetic steel plate 18a is wound around an upper end portion of magnetic element 41, with a lower end portion of magnetic element 41 protruding from magnetic steel plate 18a wound in a cylindrical shape.

Disc-shaped magnetic element 19 has holes 19a provided in correspondence with magnetic elements 18. The lower end portion of magnetic element 41 is inserted in hole 19a of magnetic element 19. Magnetic element 41 is fixed in hole 19a by bonding, press fitting, or shrink fitting. An inner circumferential portion of cylindrical coil 20 fits with an outer circumferential portion of magnetic element 18. In this modification, magnetic element 18 can be readily assembled and fixed to magnetic element 19 without using a positioning jig and the like, thus improving workability.

Figure 25:
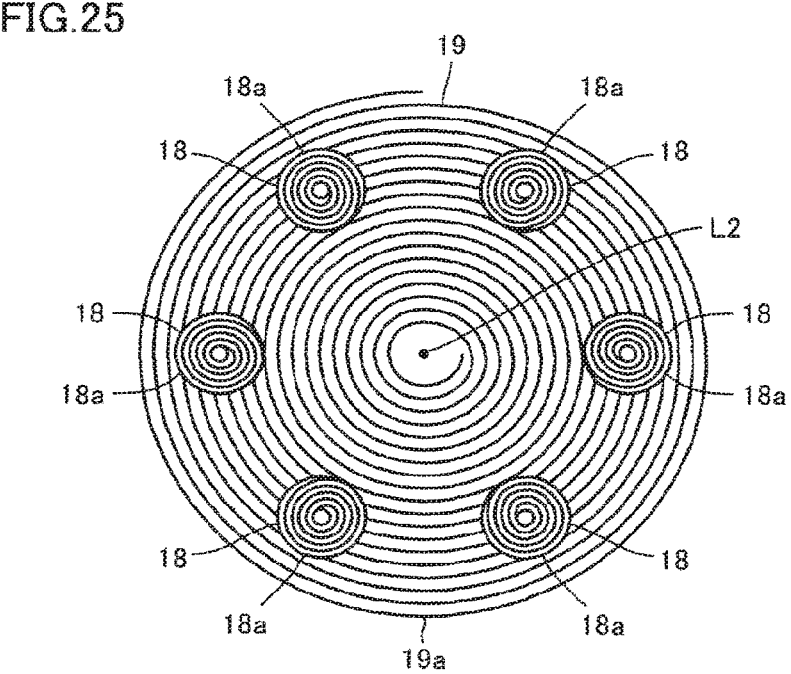
FIG. 25 is a diagram showing yet another modification of the first embodiment.

As with magnetic element 18, as shown in FIG. 25, magnetic element 19 may be formed by winding a strip-shaped magnetic steel plate 19a a plurality of times around a center line L2. In this case, iron loss in magnetic element 19 can be reduced, thereby enhancing energy efficiency when impeller 10 is driven to rotate. If magnetic steel plate 19a having a non-directional or directional magnetic property is used, magnetic permeability of a magnetic flux in magnetic element 19 can be increased, thereby enhancing energy efficiency when impeller 10 is driven to rotate.

Figure 26:
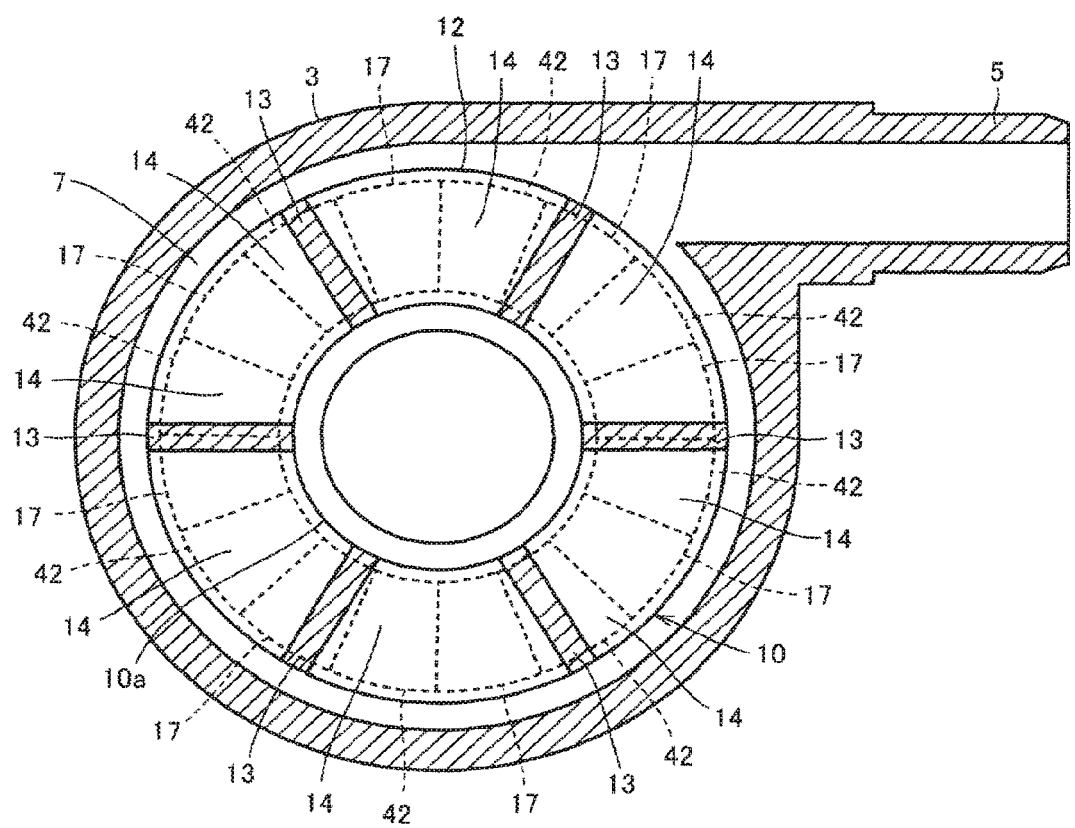
FIG. 26 is a diagram showing yet another modification of the first embodiment.

In a modification of FIG. 26, the plurality of permanent magnets 17 and a plurality of permanent magnets 42 are embedded in shroud 12. The number of permanent magnets 42 is the same as the number of permanent magnets 17. Permanent magnets 42 are magnetized in a circumferential direction (the rotation direction of impeller 10). The plurality of permanent magnets 17 and the plurality of permanent magnets 42 are alternately arranged one by one in the Halbach array at regular angular intervals along the same circle.

Figure 27:
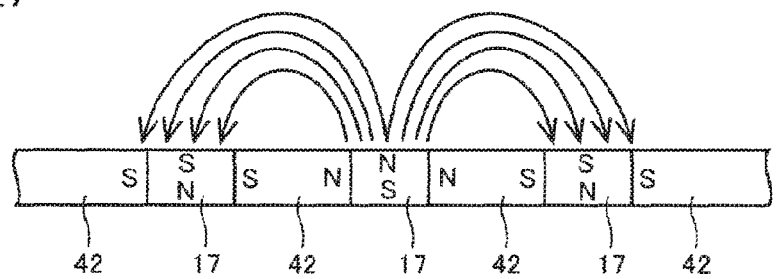
FIG. 27 is a diagram showing the polarities of permanent magnets 17, 42 shown in FIG. 26.

In other words, as shown in FIG. 27, permanent magnet 17 having the N-pole toward dividing wall 6 and permanent magnet 17 having the S-pole toward dividing wall 6 are alternately arranged with a gap therebetween at regular angular intervals along the same circle. The N-pole of each permanent magnet 42 is arranged toward permanent magnet 17 having the N-pole toward dividing wall 6, and the S-pole of each permanent magnet 42 is arranged toward permanent magnet 17 having the S-pole toward dividing wall 6. The plurality of permanent magnets 17 have the same shape, and the plurality of permanent magnets 42 have the same shape. Permanent magnets 17 may have a shape the same as or different from the shape of permanent magnets 42.

In this modification, attractive force between permanent magnets 17 and magnetic elements 18 can be suppressed and a magnetic flux that causes torque can be increased, thereby minimizing the permanent magnets. That is, the weight of impeller 10 can be minimized, and energy efficiency can be enhanced even with a wide motor gap.

Second Embodiment

Figure 28:
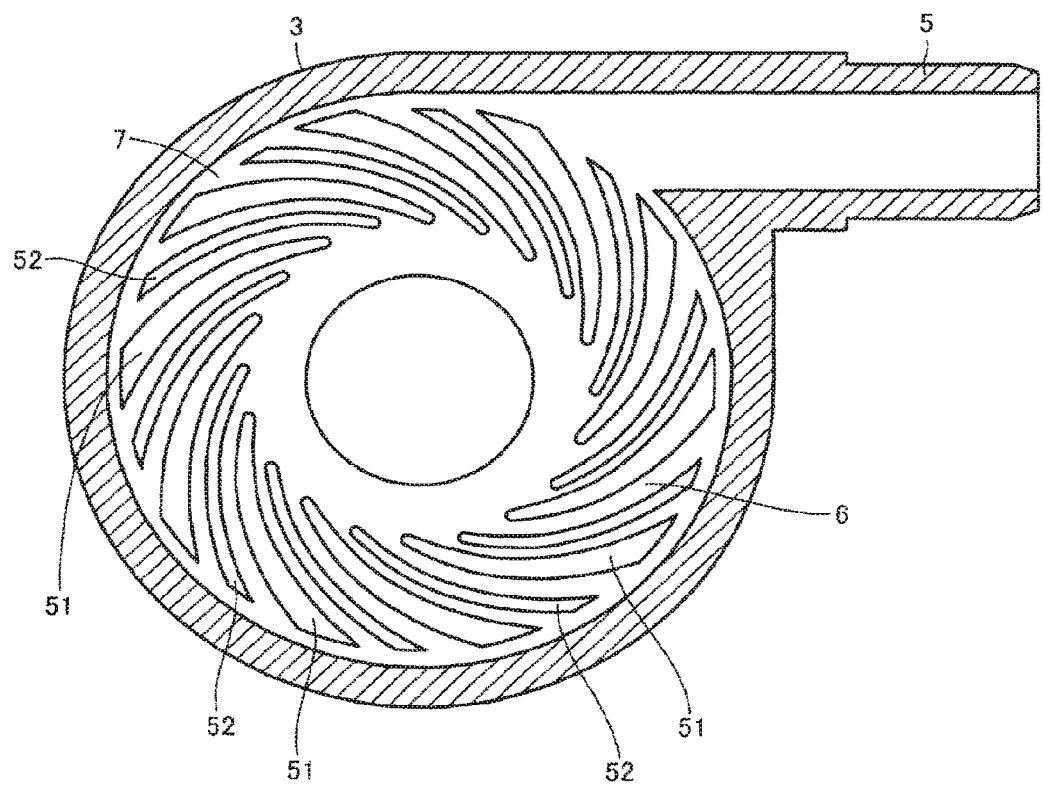
FIG. 28 is a diagram showing grooves for hydrodynamic bearing of a centrifugal blood pump apparatus according to a second embodiment of the present invention.
Figure 29:
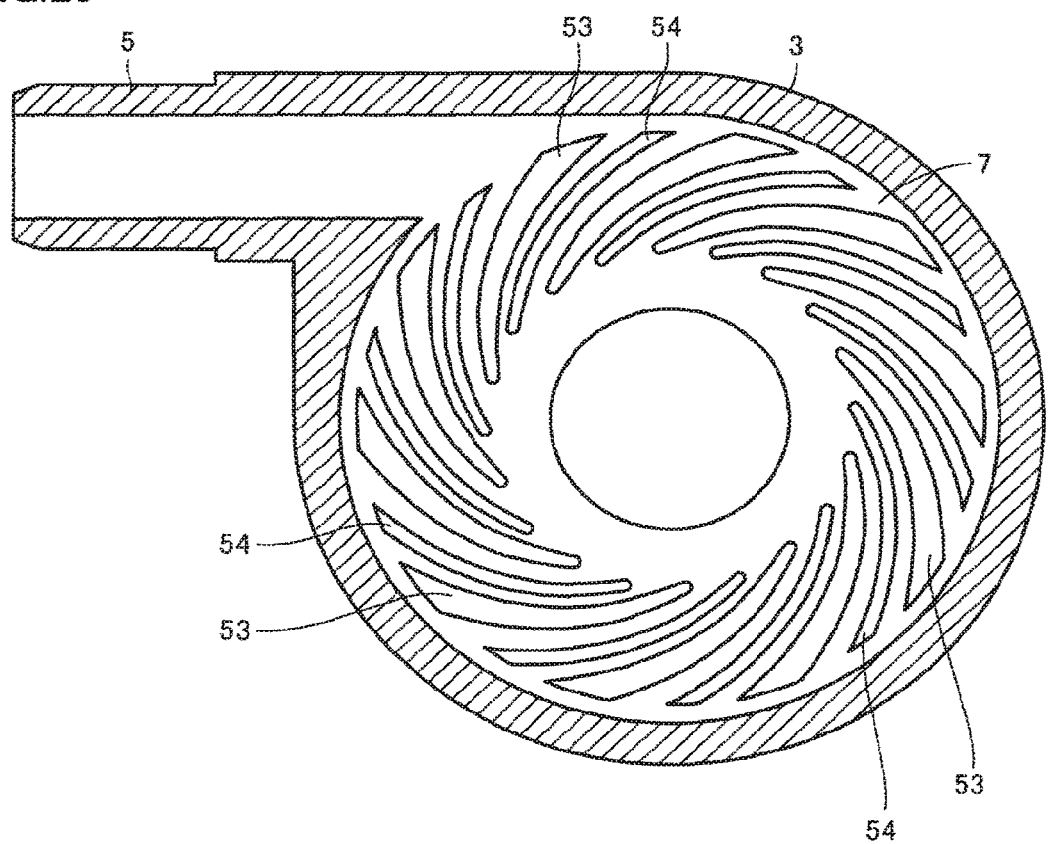
FIG. 29 is a diagram showing other grooves for hydrodynamic bearing of the centrifugal blood pump apparatus shown in FIG. 28.

FIGS. 28 and 29 are diagrams showing a substantial part of a centrifugal blood pump apparatus according to a second embodiment of the present invention, which are compared to FIGS. 5 and 6, respectively. In FIGS. 28 and 29, a plurality of grooves for hydrodynamic bearing 51 and a plurality of grooves for hydrodynamic bearing 52 are formed in a surface of dividing wall 6 facing shroud 12 of impeller 10, and a plurality of grooves for hydrodynamic bearing 53 and a plurality of grooves for hydrodynamic bearing 54 are formed in the inner wall of blood chamber 7 facing shroud 11. When a rotation speed of impeller 10 becomes higher than a prescribed rotation speed, a hydrodynamic bearing effect is produced between each of grooves for hydrodynamic bearing 51 to 54 and impeller 10. As a result, drag is generated on impeller 10 from each of grooves for hydrodynamic bearing 51 to 54, causing impeller 10 to rotate without contacting in blood chamber 7.

Specifically, as shown in FIG. 28, the plurality of grooves for hydrodynamic bearing 51 and the plurality of grooves for hydrodynamic bearing 52 are each formed with a size corresponding to shroud 12 of impeller 10. The plurality of grooves for hydrodynamic bearing 51 and the plurality of grooves for hydrodynamic bearing 52 are alternately arranged one by one, in the direction of rotation of impeller 10. Each of grooves for hydrodynamic bearing 51, 52 has one end on an edge (circumference) of a circular portion slightly distant from a center of dividing wall 6, and extends spirally (in other words, in a curved manner) toward a portion near an outer edge of dividing wall 6 such that grooves for hydrodynamic bearing 51, 52 gradually increase in width. The plurality of grooves for hydrodynamic bearing 51 have substantially the same shape, and they are arranged at regular angular intervals in the direction of rotation of impeller 10. Groove for hydrodynamic bearing 51 is a concave portion, and it preferably has a depth of about 0.005 to 0.4 mm. It is preferable that about 6 to 36 grooves for hydrodynamic bearing 51 be provided. The plurality of grooves for hydrodynamic bearing 52 have substantially the same shape, and they are arranged at regular angular intervals in the direction of rotation of impeller 10. Groove for hydrodynamic bearing 52 is a concave portion, and it preferably has a depth of about 0.005 to 0.3 mm.

Figure 30:
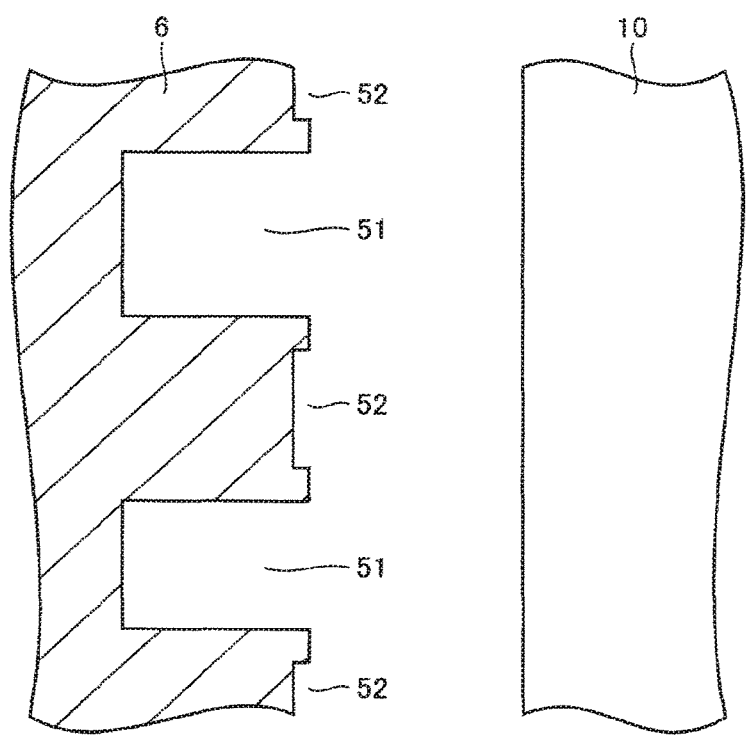
FIG. 30 is a cross-sectional view showing depths of grooves for hydrodynamic bearing 51, 52 shown in FIG. 28.

As shown in FIG. 30, groove for hydrodynamic bearing 52 is shallower than groove for hydrodynamic bearing 51. Groove for hydrodynamic bearing 52 has a depth preferably not greater than one fifth as great as a depth of groove for hydrodynamic bearing 52. In addition, groove for hydrodynamic bearing 52 has a width preferably not greater than two thirds as great as an interval between two grooves for hydrodynamic bearing 51. Further, the number of grooves for hydrodynamic bearing 52 is preferably equal to or smaller than the number of grooves for hydrodynamic bearing 51.

In FIG. 5, ten grooves for hydrodynamic bearing 51 and ten grooves for hydrodynamic bearing 52 are arranged at regular angular intervals with respect to the central axis of impeller 10. Since each of grooves for hydrodynamic bearing 51, 52 has a so-called inward spiral groove shape, clockwise rotation of impeller 10 causes increase in fluid pressure from an outer diameter portion toward an inner diameter portion of grooves for hydrodynamic bearing 51, 52. As a result, repulsion force is generated between impeller 10 and dividing wall 6 and it acts as hydrodynamic force.

Figure 31:
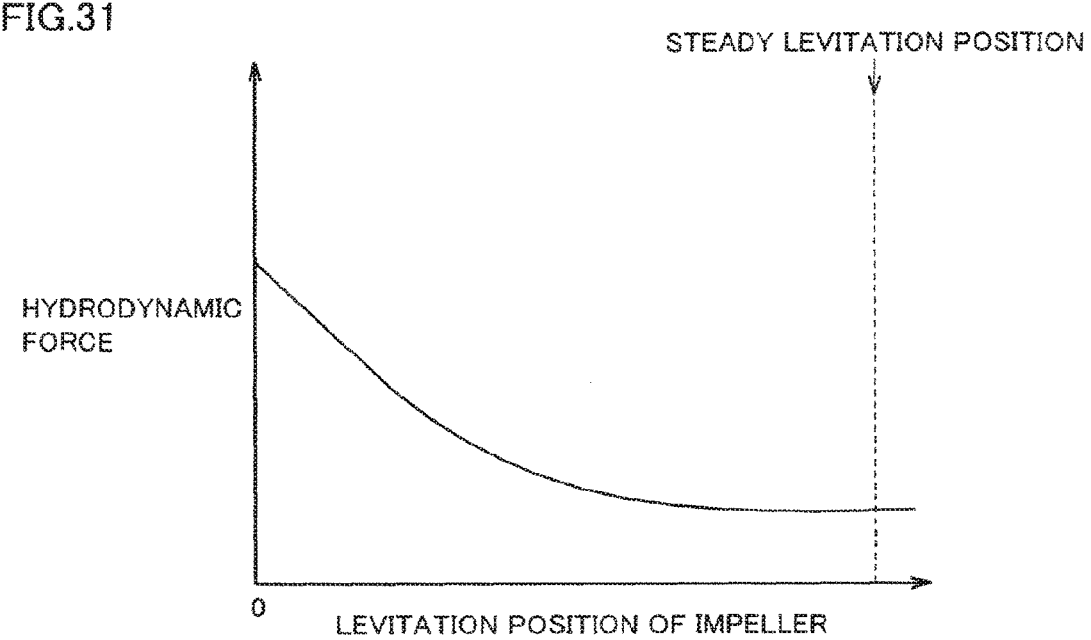
FIG. 31 is a diagram showing relation between a levitation position of the impeller and hydrodynamic force generated by groove for hydrodynamic bearing 51 shown in FIG. 30.
Figure 32:
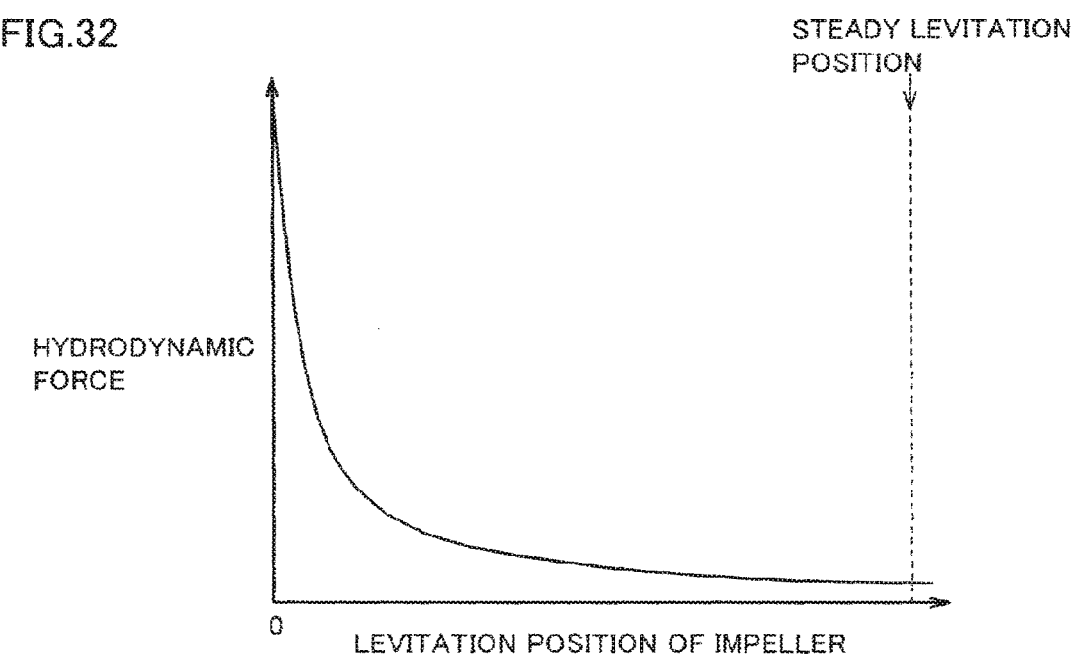
FIG. 32 is a diagram showing relation between a levitation position of the impeller and hydrodynamic force generated by groove for hydrodynamic bearing 52 shown in FIG. 30.
Figure 33:
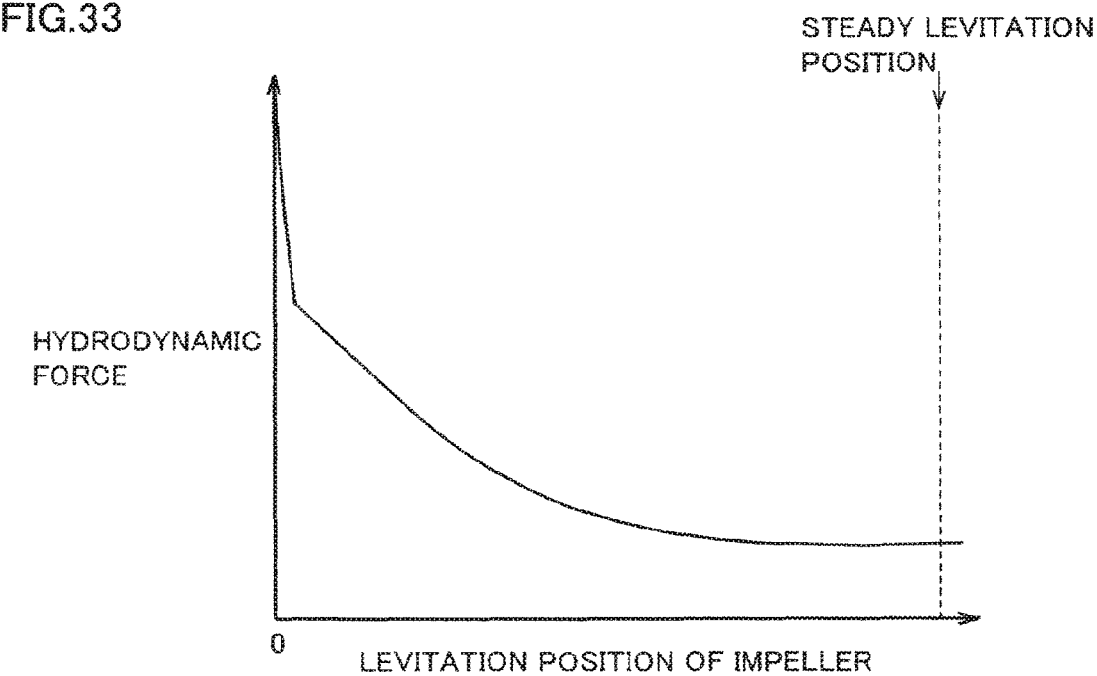
FIG. 33 is a diagram of FIGS. 31 and 32 as combined.

FIG. 31 is a diagram showing relation between a levitation position of impeller 10 when viewed from the surface of dividing wall 6 and hydrodynamic force received by impeller 10 from groove for hydrodynamic bearing 51 when impeller 10 is rotated at a prescribed rotation speed. FIG. 32 is a diagram showing relation between a distance between impeller 10 and dividing wall 6 and hydrodynamic force received by impeller 10 from groove for hydrodynamic bearing 52 when impeller 10 is rotated at a prescribed rotation speed. FIG. 33 is a diagram of FIGS. 31 and 32 as combined.

As can be seen in FIGS. 31 to 33, groove for hydrodynamic bearing 51 generates hydrodynamic force higher than that generated by groove for hydrodynamic bearing 52 when a distance between impeller 10 and dividing wall 6 is long. Meanwhile, groove for hydrodynamic bearing 52 generates hydrodynamic force higher than that generated by groove for hydrodynamic bearing 51 when a distance between impeller 10 and dividing wall 6 is short. Therefore, in the second embodiment, since both of grooves for hydrodynamic bearing 51, 52 are provided, high hydrodynamic force can be obtained in both cases of activation for rotation and steady rotation.

In this manner, owing to the hydrodynamic bearing effect produced between impeller 10 and grooves for hydrodynamic bearing 51, 52, impeller 10 moves away from dividing wall 6 and rotates without contacting. Accordingly, impeller 10 is smoothly activated to rotate and a blood flow path is secured between impeller 10 and dividing wall 6, thus preventing occurrence of blood accumulation therebetween and the resultant thrombus. Further, in a normal state, grooves for hydrodynamic bearing 51, 52 perform a stirring function between impeller 10 and dividing wall 6, thus preventing occurrence of partial blood accumulation therebetween.

Instead of providing grooves for hydrodynamic bearing 51, 52 in dividing wall 6, grooves for hydrodynamic bearing 51, 52 may be provided in a surface of shroud 12 of impeller 10.

It is preferable that a corner portion of each of grooves for hydrodynamic bearing 51, 52 be rounded to have R of at least 0.05 mm. As a result, occurrence of hemolysis can further be reduced.

Figure 34:
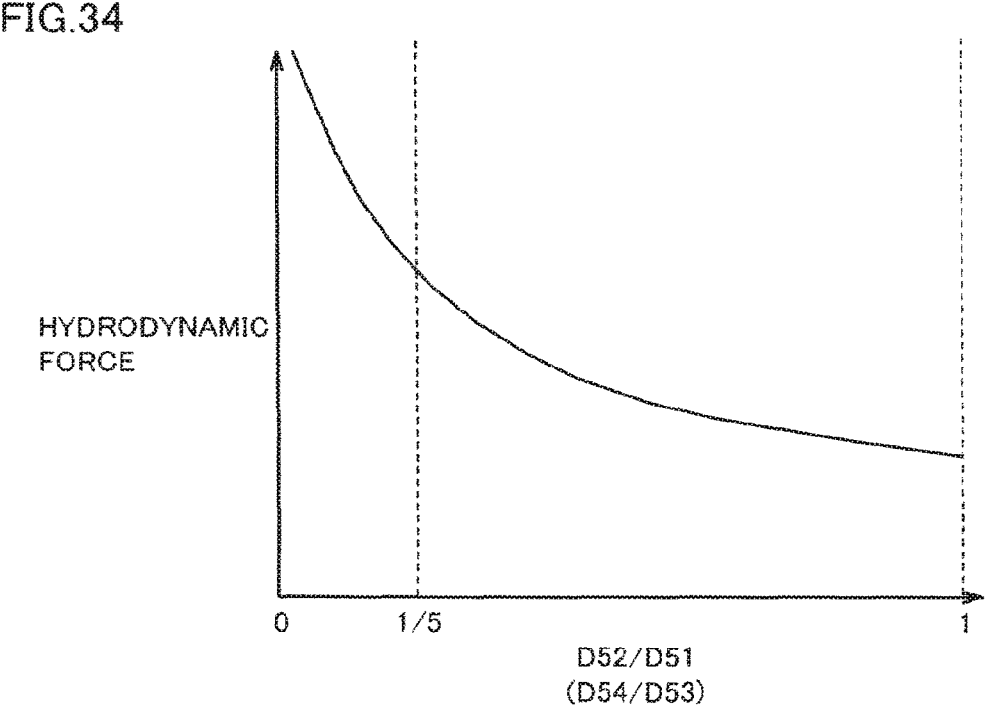
FIG. 34 is a diagram showing relation between a ratio between the depths of grooves for hydrodynamic bearing 52, 51 (or grooves for hydrodynamic bearing 54, 53) and hydrodynamic force.

FIG. 34 is a diagram showing relation between a ratio D52/D51 between a depth D52 of groove for hydrodynamic bearing 52 and a depth D51 of groove for hydrodynamic bearing 51 and hydrodynamic force acting on impeller 10 while impeller 10 is located at a steady rotation levitation position. As shown in FIG. 33, in a case where impeller 10 is located at a position proximate to dividing wall 6, high hydrodynamic force is generated by adding groove for hydrodynamic bearing 52. As shown in FIG. 34, however, when impeller 10 is located at a steady rotation levitation position, hydrodynamic force lowers by adding groove for hydrodynamic bearing 52. Therefore, a depth and a width of groove for hydrodynamic bearing 52 should be determined such that lowering in hydrodynamic force or rigidity caused by addition of groove for hydrodynamic bearing 52 does not adversely affect pump performance. As shown in FIG. 34, as ratio D52/D51 is lower, lowering in hydrodynamic force at the steady rotation levitation position can be suppressed. Therefore, preferably, ratio D52/D51 is set to 1/5 or lower.

Figure 35:
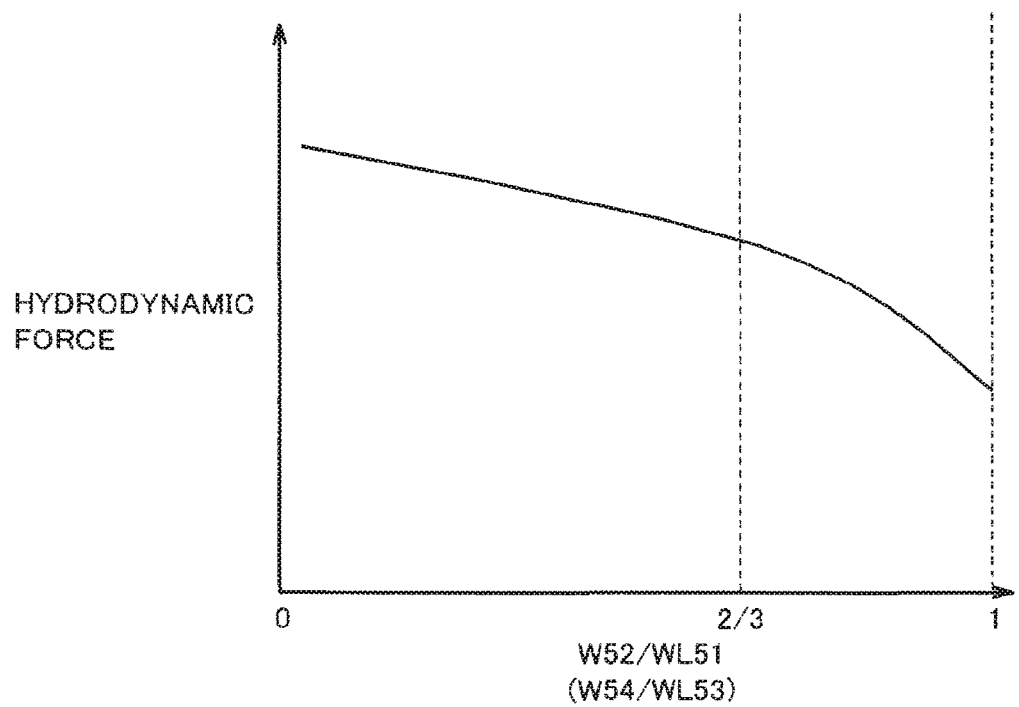
FIG. 35 is a diagram showing relation between a ratio between a width of groove for hydrodynamic bearing 52 and an interval between grooves for hydrodynamic bearing 51 (or a width of groove for hydrodynamic bearing 54 and an interval between grooves for hydrodynamic bearing 53) and hydrodynamic force.

FIG. 35 is a diagram showing relation between a ratio W52/WL51 between a width W52 of groove for hydrodynamic bearing 52 and an interval between grooves for hydrodynamic bearing 51 (a width of a land portion between grooves for hydrodynamic bearing 51) WL51 while impeller 10 is located at a steady levitation position and hydrodynamic force acting on impeller 10. As shown in FIG. 35, as ratio W52/WL51 is lower, lowering in hydrodynamic force at the steady rotation levitation position can be suppressed. Therefore, preferably, ratio W52/WL51 is set to 2/3 or lower.

As with the plurality of grooves for hydrodynamic bearing 51 and the plurality of grooves for hydrodynamic bearing 52, as shown in FIG. 29, the plurality of grooves for hydrodynamic bearing 53 and the plurality of grooves for hydrodynamic bearing 54 are each formed with a size corresponding to shroud 11 of impeller 10. Each of grooves for hydrodynamic bearing 53, 54 has one end on the edge (circumference) of the circular portion slightly distant from the center of the inner wall of blood chamber 7, and extends spirally (in other words, in a curved manner) toward the portion near the outer edge of the inner wall of blood chamber 7 such that grooves for hydrodynamic bearing 53, 54 gradually increase in width. The plurality of grooves for hydrodynamic bearing 53 have substantially the same shape and they are arranged at substantially regular intervals. Groove for hydrodynamic bearing 53 is a concave portion and it preferably has a depth of about 0.005 to 0.4 mm. It is preferable that about 6 to 36 grooves for hydrodynamic bearing 53 be provided. In FIG. 29, ten grooves for hydrodynamic bearing 53 are equiangularly arranged with respect to the central axis of impeller 10.

The plurality of grooves for hydrodynamic bearing 54 have substantially the same shape and they are arranged at regular angular intervals in the direction of rotation of impeller 10. Groove for hydrodynamic bearing 54 is a concave portion and it preferably has a depth of about 0.005 to 0.3 mm. It is preferable that about 6 to 36 grooves for hydrodynamic bearing 54 be provided.

As description of grooves for hydrodynamic bearing 51, 52 has been given with reference to FIG. 30, groove for hydrodynamic bearing 54 is shallower than groove for hydrodynamic bearing 53. Groove for hydrodynamic bearing 54 has a depth preferably not greater than one fifth as great as a depth of groove for hydrodynamic bearing 53. In addition, groove for hydrodynamic bearing 54 has a width preferably not greater than two thirds as great as an interval between two grooves for hydrodynamic bearing 53. Further, the number of grooves for hydrodynamic bearing 54 is preferably equal to or smaller than the number of grooves for hydrodynamic bearing 53.

In FIG. 29, ten grooves for hydrodynamic bearing 53 and ten grooves for hydrodynamic bearing 54 are arranged at regular angular intervals with respect to the central axis of impeller 10. Since each of grooves for hydrodynamic bearing 53, 54 has a so-called inward spiral groove shape, clockwise rotation of impeller 10 causes increase in fluid pressure from an outer diameter portion toward an inner diameter portion of grooves for hydrodynamic bearing 53, 54. As a result, repulsion force is generated between impeller 10 and the inner wall of blood chamber 7 and it acts as hydrodynamic force.

As description of grooves for hydrodynamic bearing 51, 52 has been given with reference to FIGS. 31 to 33, groove for hydrodynamic bearing 53 generates hydrodynamic force higher than that generated by groove for hydrodynamic bearing 54 when a distance between impeller 10 and the inner wall of blood chamber 7 is long. Meanwhile, groove for hydrodynamic bearing 54 generates hydrodynamic force higher than that generated by groove for hydrodynamic bearing 53 when a distance between impeller 10 and the inner wall of blood chamber 7 is short. Therefore, in the second embodiment, since both of grooves for hydrodynamic bearing 53, 54 are provided, high hydrodynamic force can be obtained in both cases of activation for rotation and steady rotation.

In this manner, owing to the hydrodynamic bearing effect produced between impeller 10 and grooves for hydrodynamic bearing 53, 54, impeller 10 moves away from the inner wall of blood chamber 7 and rotates without contacting. Accordingly, impeller 10 is smoothly activated to rotate and a blood flow path is secured between impeller 10 and the inner wall of blood chamber 7, thus preventing occurrence of blood accumulation therebetween and the resultant thrombus. Further, in a normal state, grooves for hydrodynamic bearing 53, 54 perform a stirring function between impeller 10 and the inner wall of blood chamber 7, thus preventing occurrence of partial blood accumulation therebetween. In addition, when pump unit 1 is subjected to external impact or when the hydrodynamic force by grooves for hydrodynamic bearing 51, 52 becomes excessive, impeller 10 can be prevented from being in close contact with the inner wall of blood chamber 7. The hydrodynamic force generated by grooves for hydrodynamic bearing 51, 52 may be different from the hydrodynamic force generated by grooves for hydrodynamic bearing 53, 54.

Instead of providing grooves for hydrodynamic bearing 53, 54 in the inner wall of blood chamber 7, grooves for hydrodynamic bearing 53, 54 may be provided in a surface of shroud 11 of impeller 10.

It is preferable that a corner portion of each of grooves for hydrodynamic bearing 53, 54 be rounded to have R of at least 0.05 mm. As a result, occurrence of hemolysis can further be reduced.

In addition, as description of grooves for hydrodynamic bearing 51, 52 has been given with reference to FIGS. 34 and 35, a ratio D54/D53 between a depth D54 of groove for hydrodynamic bearing 54 and a depth D53 of groove for hydrodynamic bearing 53 is set to 1/5 or lower. Moreover, a ratio W54/WL53 between a width W54 of groove for hydrodynamic bearing 54 and an interval between grooves for hydrodynamic bearing 53 (a width of a land portion between grooves for hydrodynamic bearing 53) WL53 is set to 2/3 or lower.

Further, it is preferable that impeller 10 rotate in a state where a gap between shroud 12 of impeller 10 and dividing wall 6 is substantially equal to a gap between shroud 11 of impeller 10 and the inner wall of blood chamber 7. If one of the gaps becomes narrower due to serious disturbance such as fluid force acting on impeller 10, it is preferable that grooves for hydrodynamic bearing 51, 52 and 53, 54 have different shapes so that hydrodynamic force generated by the grooves for hydrodynamic bearing on the narrower side becomes higher than the hydrodynamic force generated by the other grooves for hydrodynamic bearing to make the gaps substantially equal to each other.

While each of grooves for hydrodynamic bearing 51 to 54 has the inward spiral groove shape in FIGS. 28 and 29, grooves for hydrodynamic bearing 51 to 54 having another shape may be used. Nevertheless, for blood circulation, it is preferable to employ grooves for hydrodynamic bearing 51 to 54 having the inward spiral groove shape that allows a smooth flow of blood.

Third Embodiment

Figure 36:
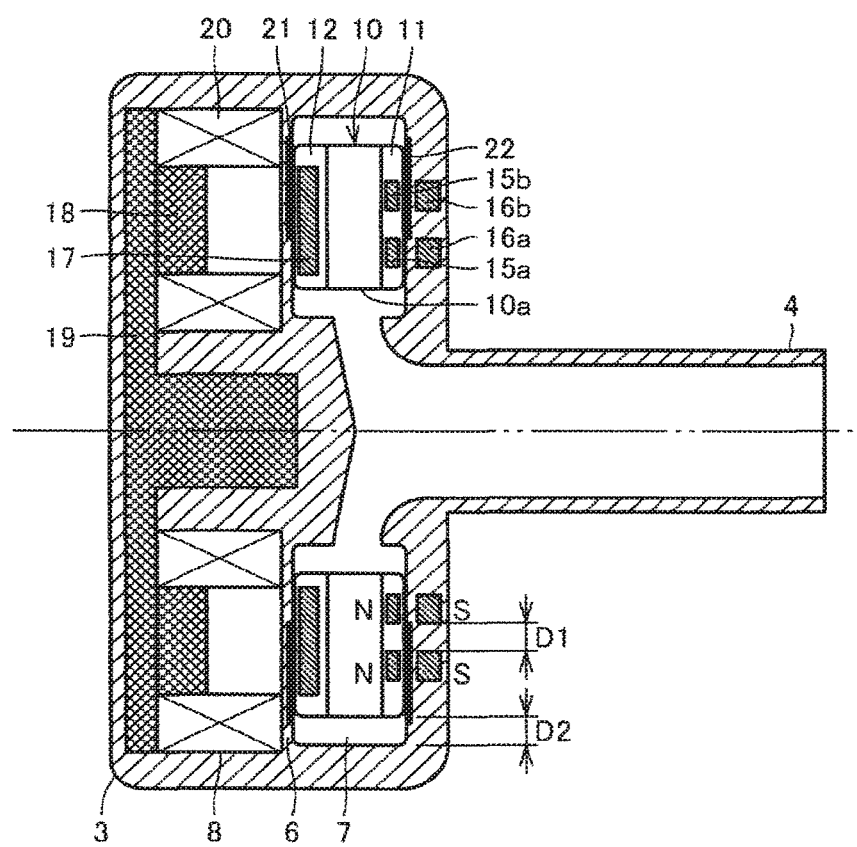
FIG. 36 is a diagram showing grooves for hydrodynamic bearing of a centrifugal blood pump apparatus according to a third embodiment of the present invention.

FIG. 36 is a diagram showing a substantial part of a centrifugal blood pump apparatus according to a third embodiment of the present invention, which is compared to FIG. 3. Referring to FIG. 36, in the third embodiment, permanent magnet 15 is radially divided into two permanent magnets 15a, 15b, and permanent magnet 16 is radially divided into two permanent magnets 16a, 16b. That is, permanent magnets 15a, 15b are embedded in shroud 11, and permanent magnets 16a, 16b for attracting permanent magnets 15a, 15b, respectively, are embedded in the inner wall of blood chamber 7 facing shroud 11. Permanent magnets 15a, 15b, 16a, 16b are provided to attract (in other words, bias) impeller 10 to the side opposite to motor chamber 8, that is, toward blood inlet port 4.

Figure 37:
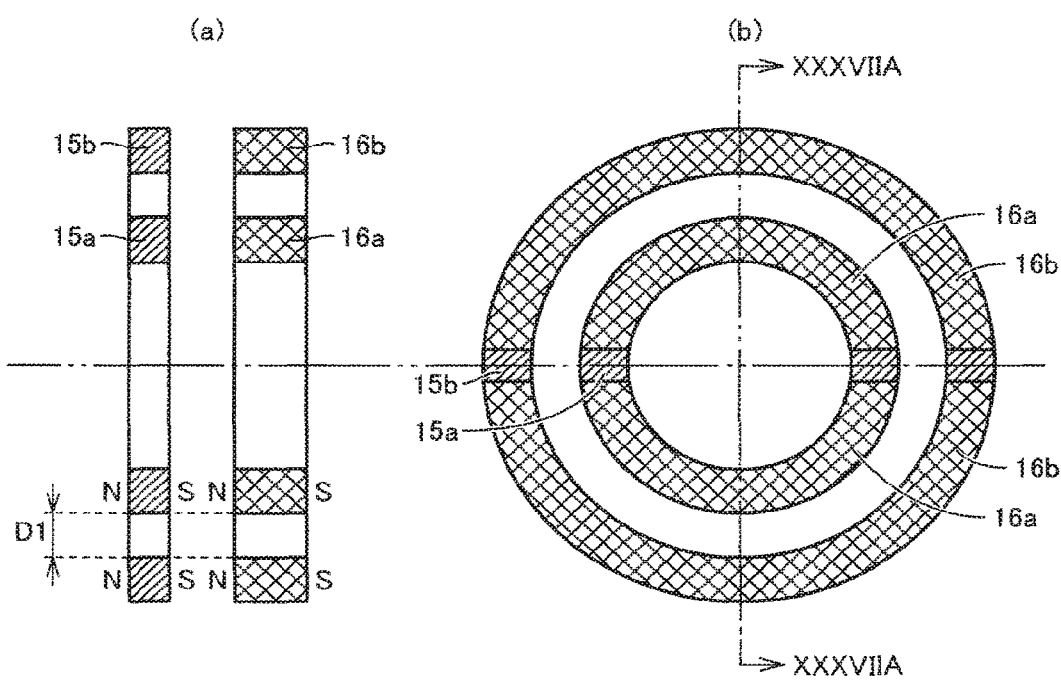
FIG. 37 is a diagram showing a configuration of a permanent magnet shown in FIG. 36.

FIGS. 37 (a) and (b) are diagrams showing configurations of permanent magnets 15a, 15b, 16a, 16b, and FIG. 37 (a) is a cross-sectional view along the line XXXVIIA-XXXVIIA in FIG. 37 (b). As shown in FIGS. 37 (a) and (b), each of permanent magnets 15a, 15b is formed in an annular ring shape, and an outer diameter of permanent magnet 15a is smaller than an inner diameter of permanent magnet 15b. Permanent magnets 15a, 15b are coaxially provided, with center points of both permanent magnets 15a, 15b being arranged on a rotation center line of impeller 10. Permanent magnets 15a, 15b have the N-poles toward the same direction.

On the other hand, each of permanent magnets 16a, 16b is formed in an arc shape, and two permanent magnets 16a and two permanent magnets 16b are arranged in the rotation direction of impeller 10. An outer diameter and an inner diameter of two permanent magnets 16a arranged in an annular ring shape are equal to the outer diameter and the inner diameter of permanent magnet 15a. An outer diameter and an inner diameter of two permanent magnets 16b arranged in an annular ring shape are equal to the outer diameter and the inner diameter of permanent magnet 15b. Permanent magnets 16a, 16b have the N-poles toward the same direction. The S-poles of permanent magnets 15a, 15b face the N-poles of permanent magnets 16a, 16b, respectively.

As shown in FIG. 36, an interval between permanent magnets 15a and 15b (i.e., an interval between permanent magnets 16a and 16b) D1 is set to be larger than a distance D2 which is half the radially movable distance of impeller 10 (i.e., a distance which is the difference between an inner diameter of blood chamber 7 and an outer diameter of impeller 10) (D1>D2). This is because, if D1<D2 is satisfied and when impeller 10 moves to a radial maximum position, permanent magnets 15a and 16b, and permanent magnets 15b and 16a interfere with each other, respectively, causing restoring force for restoring impeller 10 to the central position of the pump to be unstable.

Since the two pairs of permanent magnets 15a, 16a and permanent magnets 15b, 16b are provided in the radial direction of impeller 10 in this manner, radial supporting rigidity for impeller 10 can be made higher than in an example where only one pair of permanent magnets is provided in the radial direction of impeller 10.

Instead of providing permanent magnets 15a, 15b and permanent magnets 16a, 16b in shroud 11 and in the inner wall of blood chamber 7, respectively, a permanent magnet may be provided in one of shroud 11 and the inner wall of blood chamber 7, and a magnetic element may be provided in the other. Either a soft magnetic element or a hard magnetic element may be used as the magnetic element.

While the surfaces facing each other of permanent magnets 15a and 16a have the same size and the surfaces facing each other of permanent magnets 15b and 16b have the same size in FIG. 36, it is preferable that the surfaces facing each other of permanent magnets 15a and 16a have different sizes and the surfaces facing each other of permanent magnets 15b and 16b have different sizes in order to prevent lowering in rigidity for impeller 10 resulting from the attractive force between permanent magnets 15a, 15b and permanent magnets 16a, 16b. By making the surfaces facing each other of permanent magnets 15a, 15b and permanent magnets 16a, 16b have different sizes, the amount of variation in attractive force which varies with a distance between the magnets, that is, the negative rigidity, can be minimized, thereby preventing lowering in supporting rigidity for impeller 10.

Moreover, while each of permanent magnets 15a, 15b is formed in an annular ring shape and each of permanent magnets 16a, 16b is formed in an arc shape, with two permanent magnets 16a and two permanent magnets 16b being arranged at regular angular intervals in the rotation direction of impeller 10 in FIGS. 37 (a) and (b), conversely, each of permanent magnets 16a, 16b may be formed in an annular ring shape and each of permanent magnets 15a, 15b may be formed in an arc shape, with two permanent magnets 15a and two permanent magnets 15b being arranged at regular angular intervals in the rotation direction of impeller 10. Alternatively, each of permanent magnets 15a, 15b or each of permanent magnets 16a, 16b may be formed in a shorter arc shape, and a plurality of them may be arranged at regular angular intervals in the rotation direction of impeller 10.

Fourth Embodiment

Figure 38:
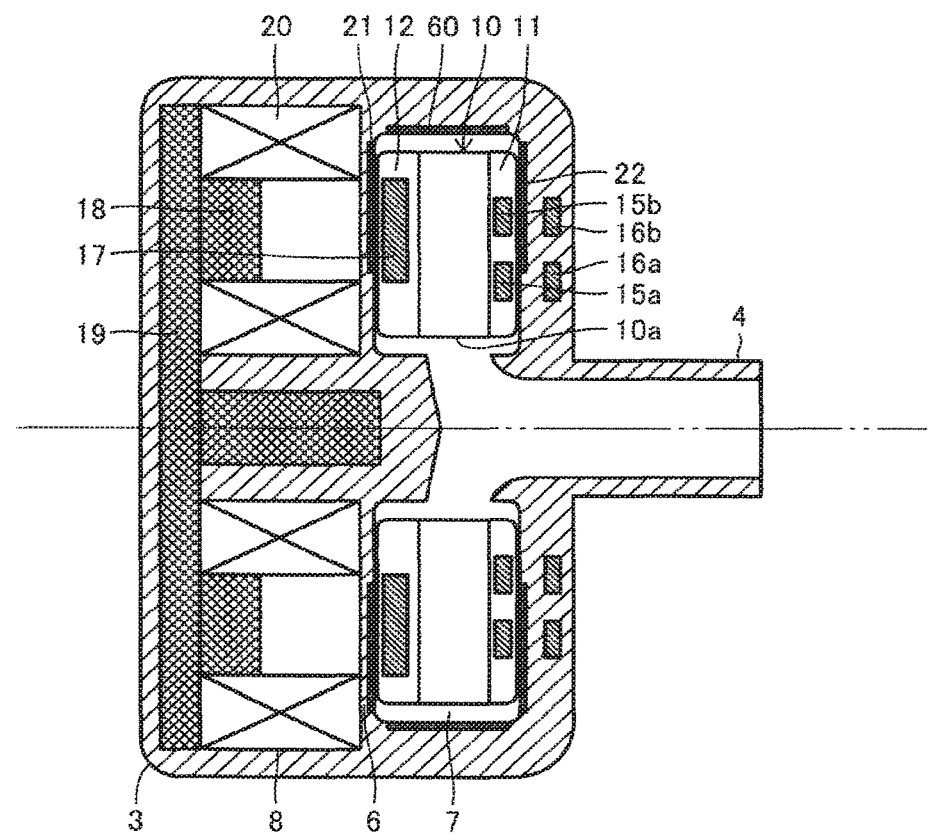
FIG. 38 is a cross-sectional view showing a structure of a centrifugal blood pump apparatus according to a fourth embodiment of the present invention.

FIG. 38 is a cross-sectional view showing a substantial part of a centrifugal blood pump apparatus according to a fourth embodiment of the present invention, which is compared to FIG. 36. In FIG. 38, this centrifugal blood pump apparatus is different from the centrifugal blood pump apparatus shown in FIG. 36 in that a groove for hydrodynamic bearing 60 is formed in an inner circumferential surface of blood chamber 7 facing an outer circumferential surface of impeller 10. Groove for hydrodynamic bearing 60 generates hydrodynamic force for the outer circumferential surface of impeller 10, to prevent the outer circumferential surface of impeller 10 from making contact with the inner circumferential surface of blood chamber 7.

Figure 39:
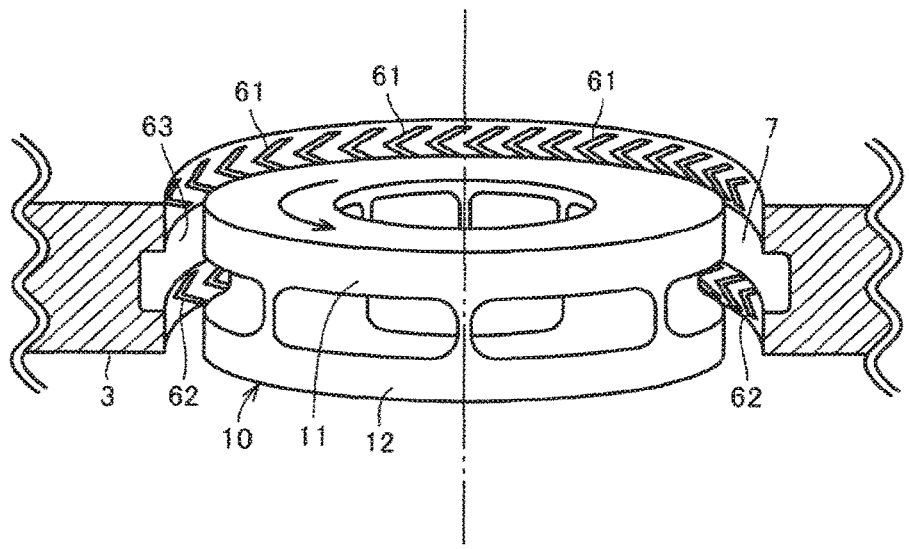
FIG. 39 is a diagram illustrating a structure of the grooves for hydrodynamic bearing shown in FIG. 36.

FIG. 39 is a diagram illustrating a specific structure of groove for hydrodynamic bearing 60. In FIG. 39, in an area of the inner circumferential surface of blood chamber 7 facing an outer circumferential surface of shroud 11, V-shaped grooves for hydrodynamic bearing 61 are formed at a prescribed pitch in the rotation direction of impeller 10. V-shaped groove for hydrodynamic bearing 61 has a tip (acute angle portion) toward the rotation direction of impeller 10. Likewise, in an area of the inner circumferential surface of blood chamber 7 facing an outer circumferential surface of shroud 12, V-shaped grooves for hydrodynamic bearing 62 are formed at a prescribed pitch in the rotation direction of impeller 10. V-shaped groove for hydrodynamic bearing 62 has a tip (acute angle portion) toward the rotation direction of impeller 10. In an area of the inner circumferential surface of blood chamber 7 facing a gap between shrouds 11 and 12, a groove 63 having a prescribed depth is formed in a ring shape. Rotation of impeller 10 in a direction of an arrow causes increase in fluid pressure toward the tip portions of grooves for hydrodynamic bearing 61, 62. As a result, repulsion force is generated between impeller 10 and the inner circumferential surface of blood chamber 7 and it acts as hydrodynamic force.

Figure 40:
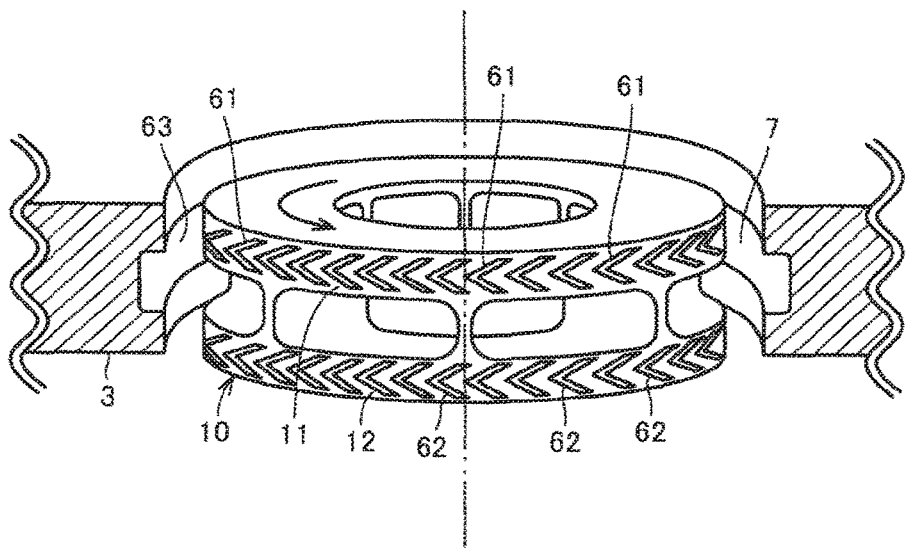
FIG. 40 is a diagram showing a modification of the fourth embodiment.

FIG. 40 is a diagram showing a modification of the fourth embodiment, which is compared to FIG. 39. Referring to FIG. 40, in this modification, grooves for hydrodynamic bearing 61, 62 are formed in the outer circumferential surfaces of shrouds 11, 12, respectively, instead of being formed in the inner circumferential surface of blood chamber 7. Each of grooves for hydrodynamic bearing 61, 62 has a tip toward a direction opposite to the rotation direction of impeller 10. Rotation of impeller 10 in a direction of an arrow causes increase in fluid pressure toward the tip portions of grooves for hydrodynamic bearing 61, 62. As a result, repulsion force is generated between impeller 10 and the inner circumferential surface of blood chamber 7 and it acts as hydrodynamic force.

Figure 41:
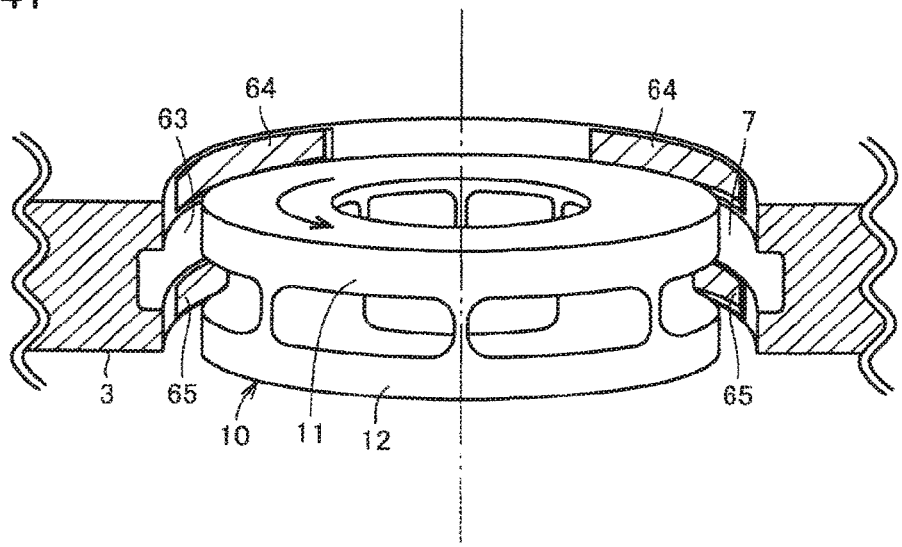
FIG. 41 is a diagram showing another modification of the fourth embodiment.

FIG. 41 is a diagram showing another modification of the fourth embodiment, which is compared to FIG. 39. Referring to FIG. 41, in this modification, grooves for hydrodynamic bearing 61, 62 are replaced with grooves for hydrodynamic bearing 64, 65, respectively. Each of grooves for hydrodynamic bearing 64, 65 is formed in a strip shape, and extends in the rotation direction of impeller 10. Each of grooves for hydrodynamic bearing 64, 65 has a depth that gradually decreases toward the rotation direction of impeller 10. In this modification as well, rotation of impeller 10 in a direction of an arrow causes increase in fluid pressure toward the tip portions of grooves for hydrodynamic bearing 64, 65. As a result, repulsion force is generated between impeller 10 and the inner circumferential surface of blood chamber 7 and it acts as hydrodynamic force.

Figure 42:
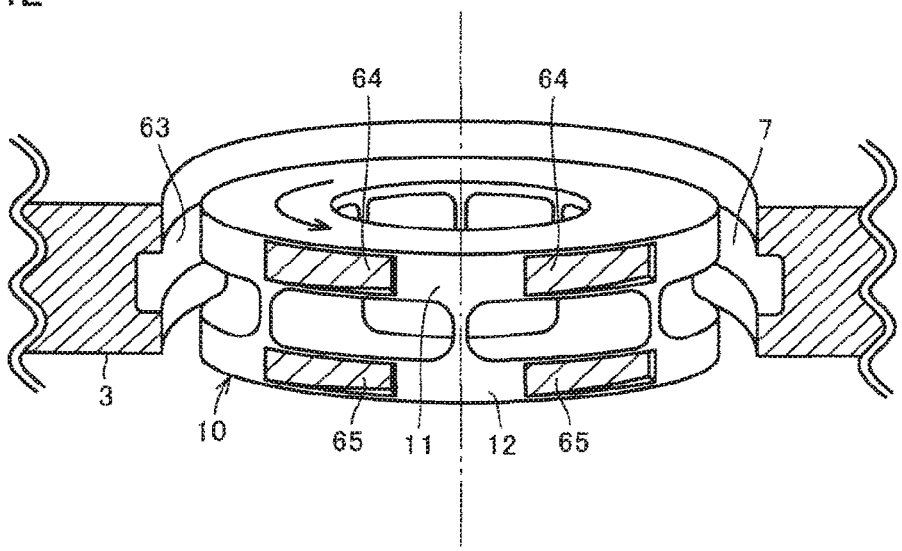
FIG. 42 is a diagram showing yet another modification of the fourth embodiment.

FIG. 42 is a diagram showing yet another modification of the fourth embodiment, which is compared to FIG. 41. Referring to FIG. 41, in this modification, grooves for hydrodynamic bearing 64, 65 are formed in the outer circumferential surfaces of shrouds 11, 12, respectively, instead of being formed in the inner circumferential surface of blood chamber 7. Each of grooves for hydrodynamic bearing 64, 65 has a depth that gradually decreases toward a direction opposite to the rotation direction of impeller 10. In this modification as well, rotation of impeller 10 in a direction of an arrow causes increase in fluid pressure toward the tip portions of grooves for hydrodynamic bearing 64, 65. As a result, repulsion force is generated between impeller 10 and the inner circumferential surface of blood chamber 7 and it acts as hydrodynamic force.

Figure 43:
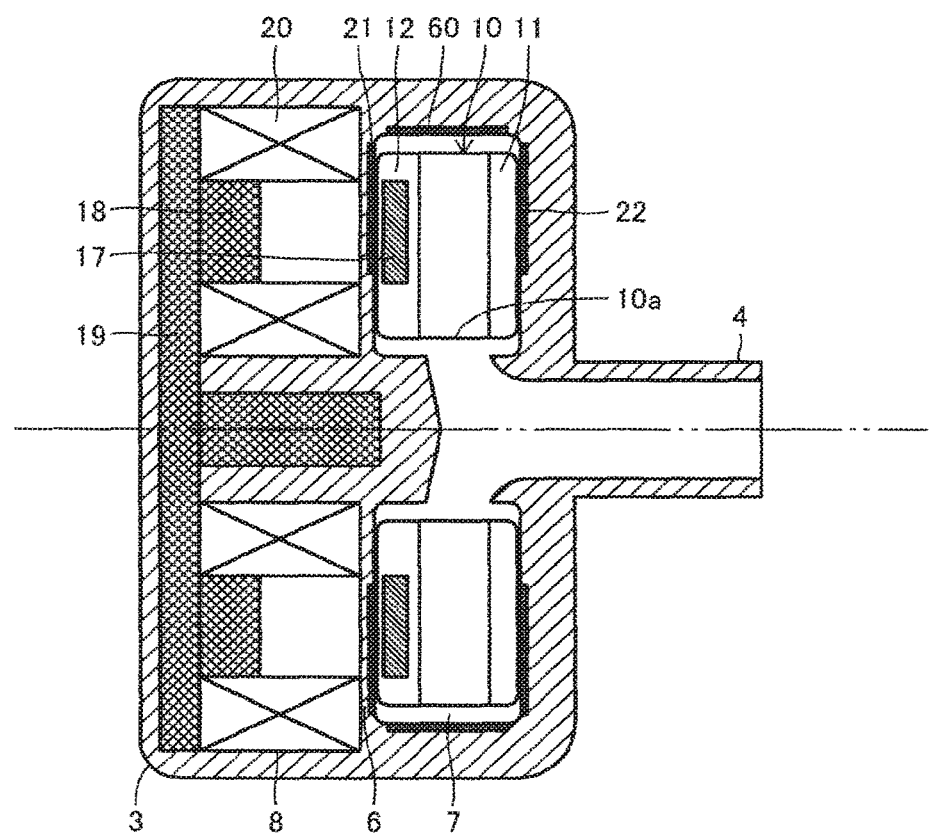
FIG. 43 is a diagram showing yet another modification of the fourth embodiment.

FIG. 43 is a diagram showing yet another modification of the fourth embodiment, which is compared to FIG. 38. Referring to FIG. 43, in this modification, permanent magnets 15a, 15b, 16a, 16b have been removed. This structure is possible by making magnetic elements 18 shorter than coils 20 so that the attractive force between permanent magnets 17 and magnetic elements 18 becomes smaller than hydrodynamic force F3 during rated rotation substantially in the center of the movable range of impeller 10 in blood chamber 7. During rotation of impeller 10, force which is the sum of hydrodynamic force F4 during rated rotation generated by grooves for hydrodynamic bearing 22 and attractive force F2 between magnetic elements 18 and permanent magnets 17 (F2+F4) and hydrodynamic force F3 during rated rotation generated by grooves for hydrodynamic bearing 21 are set to be balanced with each other substantially in the center of the movable range of impeller 10 in blood chamber 7.

Figure 44:
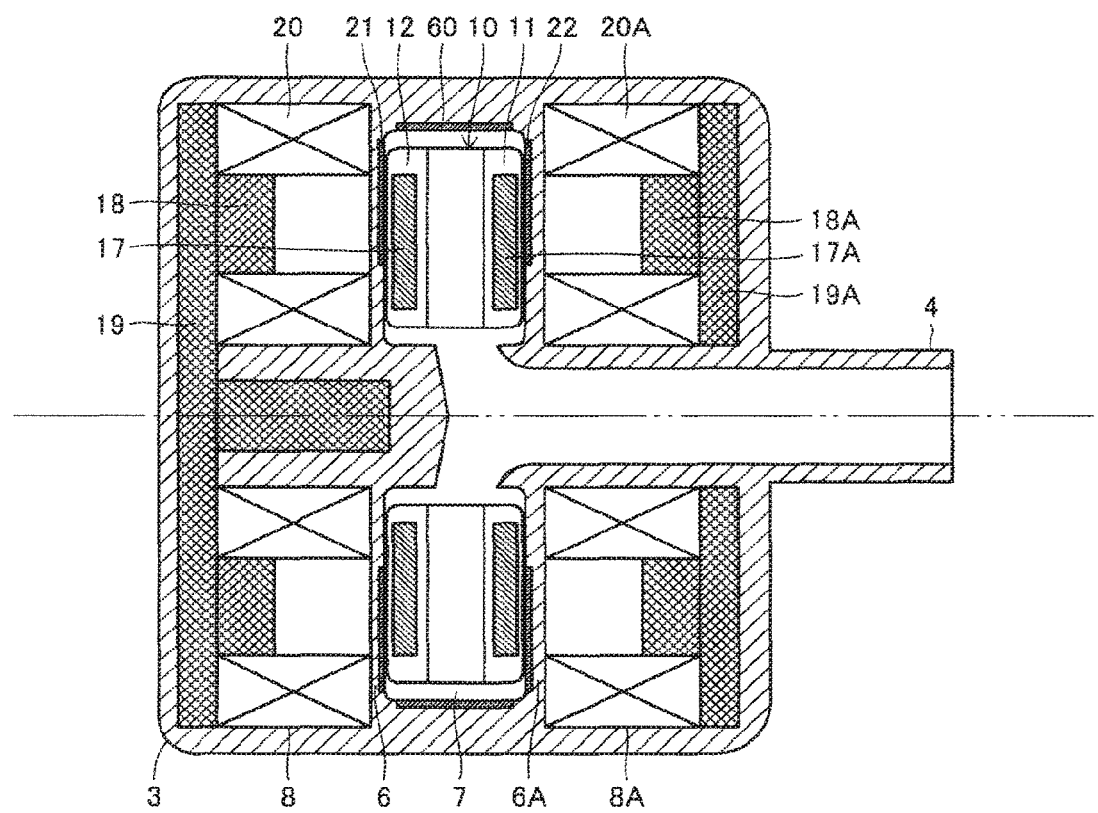
FIG. 44 is a diagram showing yet another modification of the fourth embodiment.

FIG. 44 is a diagram showing yet another modification of the fourth embodiment, which is compared to FIG. 43. Referring to FIG. 43, in this modification, a plurality of permanent magnets 17A are provided in shroud 11 as well, and a motor chamber 8A is provided on the shroud 11 side as well. Motor chamber 8A and blood chamber 7 are partitioned from each other by a dividing wall 6A. A plurality of magnetic elements 18A are provided in motor chamber 8A to face the plurality of permanent magnets 17A. A coil 20A is wound around each magnetic element 18A, which is joined to a disc-shaped magnetic element 19A. In the direction of the central axis of impeller 10, magnetic element 18A is shorter than coil 20A. During rotation of impeller 10, first attractive force between the plurality of permanent magnets 17 and the plurality of magnetic elements 18 and second attractive force between the plurality of permanent magnets 17A and the plurality of magnetic elements 18B are set to be balanced with each other substantially in the center of the movable range of impeller 10 in blood chamber 7.

It should be understood that the embodiments disclosed herein are illustrative and non-restrictive in every respect. The scope of the present invention is defined by the teens of the claims, rather than the description above, and is intended to include any modifications within the scope and meaning equivalent to the terms of the claims.

REFERENCE SIGNS LIST 1 pump unit; 2 housing; 3 body portion; 4 blood inlet port; 5 blood outlet port; 6, 6A dividing wall; 7 blood chamber; 8, 8A motor chamber; 10 impeller; 10a through hole; 11, 12 shroud; 13 vane; 14 blood passage; 15 to 17, 15a, 15b, 16a, 16b, 42 permanent magnet; 18, 18A, 19, 19A, 36 to 39, 41 magnetic element; 18a, 19a magnetic steel plate; 20, 20A coil; 21, 22, 51, 52, 60 to 62, 64, 65 groove for hydrodynamic bearing; 25 controller; 26 motor control circuit; 27, 30, 31 power amplifier; 32 switch; 40 notch; 63 groove.

What is claimed is:

1. A centrifugal pump apparatus including a housing having first and second chambers partitioned from each other by a dividing wall, an impeller rotatably provided in said first chamber along said dividing wall, for delivering fluid by centrifugal force during rotation, and a drive unit provided in said second chamber for driving said impeller to rotate, comprising:
a first magnetic element provided in one surface of said impeller;
a second magnetic element provided in an inner wall of said first chamber facing the one surface of said impeller, for attracting said first magnetic element; and
a plurality of third magnetic elements provided in an other surface of said impeller, arranged in a direction of rotation of said impeller, and attracted by said drive unit, wherein:
said drive unit includes
a plurality of coils provided to face said plurality of third magnetic elements, for generating a rotating magnetic field,
a plurality of fourth magnetic elements provided in correspondence with said plurality of coils respectively and each inserted in the corresponding coil,
each said fourth magnetic element is shorter than the corresponding coil in a direction of a central axis of said impeller,
during rotation of said impeller, a first attractive force between said first and second magnetic elements and a second attractive force between said plurality of third magnetic elements and said plurality of fourth magnetic elements are balanced with each other substantially in a center of a movable range of said impeller in said first chamber,
a first groove for hydrodynamic bearing is formed in one surface of said impeller or in the inner wall of said first chamber facing the one surface,
a second groove for hydrodynamic bearing is formed in the other surface of said impeller or in said dividing wall facing the other surface, and
each said fourth magnetic element includes a strip-shaped magnetic steel plate wound a plurality of times around a center line.

2. The centrifugal pump apparatus according to claim 1, wherein
said drive unit further includes a disc-shaped fifth magnetic element,
said plurality of coils are provided between said dividing wall and said fifth magnetic element, and
said plurality of fourth magnetic elements are joined to said fifth magnetic element.

3. The centrifugal pump apparatus according to claim 1, wherein each said fourth magnetic element is formed in a cylindrical shape.

4. The centrifugal pump apparatus according to claim 1, wherein each said fourth magnetic element is made of pure iron, soft iron, or ferrosilicon.

5. The centrifugal pump apparatus according to claim 1, wherein each said fourth magnetic element is made of powders of pure iron, soft iron, or ferrosilicon.

6. The centrifugal pump apparatus according to claim 1, wherein
a third groove for hydrodynamic bearing is formed in an outer circumferential surface of said impeller or in an inner circumferential surface of said first chamber facing the outer circumferential surface.

7. The centrifugal pump apparatus according to claim 1, wherein said fluid is blood, and said centrifugal pump apparatus is used for circulating said blood.

8. A centrifugal pump apparatus including a housing having first and second chambers partitioned from each other by a dividing wall, an impeller rotatably provided in said first chamber along said dividing wall, for delivering fluid by centrifugal force during rotation, and a drive unit provided in said second chamber for driving said impeller to rotate, comprising a plurality of first magnetic elements provided in said impeller, arranged in a direction of rotation of said impeller, and attracted by said drive unit, wherein said drive unit includes a plurality of coils provided to face said plurality of first magnetic elements, for generating a rotating magnetic field, a plurality of second magnetic elements provided in correspondence with said plurality of coils respectively and each inserted in the corresponding coil, each said second magnetic element is shorter than the corresponding coil in a direction of a central axis of said impeller, a first groove for hydrodynamic bearing is formed in one surface of said impeller or in an inner wall of said first chamber facing the one surface, and a second groove for hydrodynamic bearing is formed in an other surface of said impeller or in said dividing wall facing the other surface, during rotation of said impeller, a force which is the sum of a first hydrodynamic force during rated rotation generated by said first groove for hydrodynamic bearing and an attractive force between said plurality of first magnetic elements and said plurality of second magnetic elements, and a second hydrodynamic force during rated rotation generated by said second groove for hydrodynamic bearing are balanced with each other substantially in a center of a movable range of said impeller in said first chamber, and each said second magnetic element includes a strip-shaped magnetic steel plate wound a plurality of times around a center line.

9. The centrifugal pump apparatus according to claim 8, wherein said drive unit further includes a disc-shaped third magnetic element, said plurality of coils are provided between said dividing wall and said third magnetic element, and said plurality of second magnetic elements are joined to said third magnetic element.

10. The centrifugal pump apparatus according to claim 8, wherein a third groove for hydrodynamic bearing is formed in an outer circumferential surface of said impeller or in an inner circumferential surface of said first chamber facing the outer circumferential surface.

11. The centrifugal pump apparatus according to claim 8, wherein said fluid is blood, and said centrifugal pump apparatus is used for circulating said blood.

12. A centrifugal pump apparatus including a housing having first and second dividing walls and a fluid chamber therebetween, an impeller rotatably provided in said fluid chamber along said first and second dividing walls, for delivering fluid by centrifugal force during rotation, and first and second drive units provided outside said fluid chamber, for driving said impeller to rotate, respectively, comprising a plurality of first magnetic elements provided in said impeller, arranged in a direction of rotation of said impeller, and attracted by said first and second drive units, wherein each of said first and second drive units includes a plurality of coils provided to face said plurality of first magnetic elements, for generating a rotating magnetic field, a plurality of second magnetic elements provided in correspondence with said plurality of coils respectively and each inserted in the corresponding coil, each said second magnetic element is shorter than the corresponding coil in a direction of a central axis of said impeller, during rotation of said impeller, a first attractive force between said plurality of first magnetic elements and said plurality of second magnetic elements of said first drive unit and a second attractive force between said plurality of first magnetic elements and said plurality of second magnetic elements of said second drive unit are balanced with each other substantially in a center of a movable range of said impeller in said fluid chamber, a first groove for hydrodynamic bearing is formed in one surface of said impeller or in said first dividing wall facing the one surface, and a second groove for hydrodynamic bearing is formed in an other surface of said impeller or in said second dividing wall facing the other surface, and each said second magnetic element includes a strip-shaped magnetic steel plate wound a plurality of times around a center line.

13. The centrifugal pump apparatus according to claim 12, wherein each of said first and second drive units further includes a disc-shaped third magnetic element, said plurality of coils of said first drive unit are provided between said first dividing wall and said third magnetic element of said first drive unit, said plurality of coils of said second drive unit are provided between said second dividing wall and said third magnetic element of said second drive unit, and in each of said first and second drive units, said plurality of second magnetic elements are joined to said third magnetic element.

14. The centrifugal pump apparatus according to claim 12, wherein a third groove for hydrodynamic bearing is formed in an outer circumferential surface of said impeller or in an inner circumferential surface of said fluid chamber facing the outer circumferential surface.

15. The centrifugal pump apparatus according to claim 12, wherein said fluid is blood, and said centrifugal pump apparatus is used for circulating said blood.

* * * * *